US012767675B2

(12) United States Patent
Bodennec et al.

(10) Patent No.: US 12,767,675 B2
(45) Date of Patent: Oct. 20, 2026

(54) STRUCTURED MOLECULAR VECTORS FOR ANTI-INFLAMMATORY COMPOUNDS AND USES THEREOF

(71) Applicants: UNIVERSITE CLAUDE BERNARD LYON 1, Villeurbanne (FR); CENTRE NATIONAL DE LA RECHERCHE SCIENTIFIQUE, Paris (FR); INSTITUT NATIONAL DE LA SANTE ET DE LA RECHERCHE MEDICALE, Paris (FR); UNIVERSITE JEAN MONNET SAINT ETIENNE, Saint Etienne (FR)

(72) Inventors: Jacques Bodennec, Les Avenieres (FR); Amor Belmeguenaï, Vaulx en Velin (FR); Selena Bodennec, Les Avenieres (FR); Laurent Bezin, La Chappelle sous Brancion (FR); Béatrice Georges, Meyzieu (FR); Victor Blot, Lyons (FR)

(73) Assignees: Universite Claude Bernard Lyon 1, Villeurbanne (FR); Centre National de la Recherche Scientifique, Paris (FR); Institut National de la Sante et de la Recherche Medicale, Paris (FR); Universite Jean Monnet Saint Etienne, Saint Etienne (FR)

( * ) Notice: Subject to any disclaimer, the term of this patent is extended or adjusted under 35 U.S.C. 154(b) by 1058 days.

(21) Appl. No.: 17/432,510

(22) PCT Filed: Feb. 21, 2020

(86) PCT No.: PCT/EP2020/054662

§ 371 (c)(1),
(2) Date: Aug. 20, 2021

(87) PCT Pub. No.: WO2020/169822

PCT Pub. Date: Aug. 27, 2020

(65) Prior Publication Data

US 2022/0162239 A1 May 26, 2022

(30) Foreign Application Priority Data

Feb. 21, 2019 (EP) .................................... 19305212
Oct. 23, 2019 (EP) .................................... 19306376

(51) Int. Cl.
*C07F 9/40* (2006.01)
*A61P 25/08* (2006.01)
*C07F 9/38* (2006.01)

(52) U.S. Cl.
CPC ............ *C07F 9/4009* (2013.01); *A61P 25/08* (2018.01); *C07F 9/3817* (2013.01)

(58) Field of Classification Search
CPC ........ C07F 9/4009; C07F 9/3817; C07F 9/09; A61P 25/08; A61P 1/00; A61P 25/28; A61P 29/00; A23L 29/04; A23L 33/12; A61K 31/661; A61K 31/662; A61K 31/685; A61K 31/688; A61K 31/131
USPC .......................................................... 514/547
See application file for complete search history.

(56) References Cited

U.S. PATENT DOCUMENTS

| | | | | |
|---|---|---|---|---|
| 2,993,067 | A | 7/1961 | Magerlein et al. | |
| 10,933,037 | B2 * | 3/2021 | Levin | A61P 3/04 |
| 2001/0037032 | A1 | 11/2001 | Strelchenok | |
| 2005/0130937 | A1 * | 6/2005 | Ben Dror | A23D 7/013 426/601 |
| 2006/0193905 | A1 | 8/2006 | Ehringer et al. | |
| 2007/0099868 | A1 * | 5/2007 | Harats | A61P 29/00 536/53 |
| 2010/0240616 | A1 * | 9/2010 | Holmeide | C07C 69/24 554/170 |
| 2015/0216883 | A1 | 8/2015 | Daniels | |

FOREIGN PATENT DOCUMENTS

| | | |
|---|---|---|
| CN | 105622925 | 9/2017 |
| EP | 0 821 068 | 1/1998 |
| EP | 3 135 297 | 3/2017 |
| JP | 2012180311 | 9/2012 |
| WO | WO 97/39004 | 10/1997 |

(Continued)

OTHER PUBLICATIONS

Park et al. Journal of Neuroinflammation , 2016, 13:284, "N-Docosahexaenoylethanolamine ameliorates LPS-induced neuroinflammation via cAMP/PKAdependent signaling". (Year: 2016).*

Sonti et al. Chemistry and Physics of Lipids 210 (2018) 90-97, https://doi.org/10.1016/j.chemphyslip.2017.11.002 , "N-Docosahexaenoylethanolamine (synaptamide): Carbon-14 radiolabeling and metabolic studies" (Year: 2018).*

Lynch Prostaglandins & other Lipid Mediators 64 (2001) 33-45; Structure activity relationships of lysophospholipid mediators (Year: 2001).*

Aksenov et al. Doklady Natsional'noi Akademii Nauk Belarusi (2001), 45(2), 63-66, (Year: 2001).*

Elliott et al. Med. Chem. Commun., 2012, 3, 735, https://doi.org/10.1039/C2MD20079A, The use of phosphate bioisosteres in medicinal chemistry and chemical biology. (Year: 2012).*

(Continued)

*Primary Examiner* — Jared Barsky
*Assistant Examiner* — Liyuan Mou
(74) *Attorney, Agent, or Firm* — Amster, Rothstein & Ebenstein LLP

(57) ABSTRACT

The present invention relates to structured molecular vectors of formula (I), compounds of formula (II) and pharmaceutical compositions comprising such compounds. The invention also relates to such pharmaceutical compositions for use for preventing and/or treating a disease chosen among an inflammatory disease or a disease associated with a cognitive disorder. The invention further relates to such pharmaceutical compositions for use for preventing cognitive decline or restoring cognitive functions altered in brain injuries and/or in traumatic brain injuries and/or in a neuroinflammatory disease, and/or in a neurodegenerative disease.

3 Claims, 24 Drawing Sheets

Figure 1:
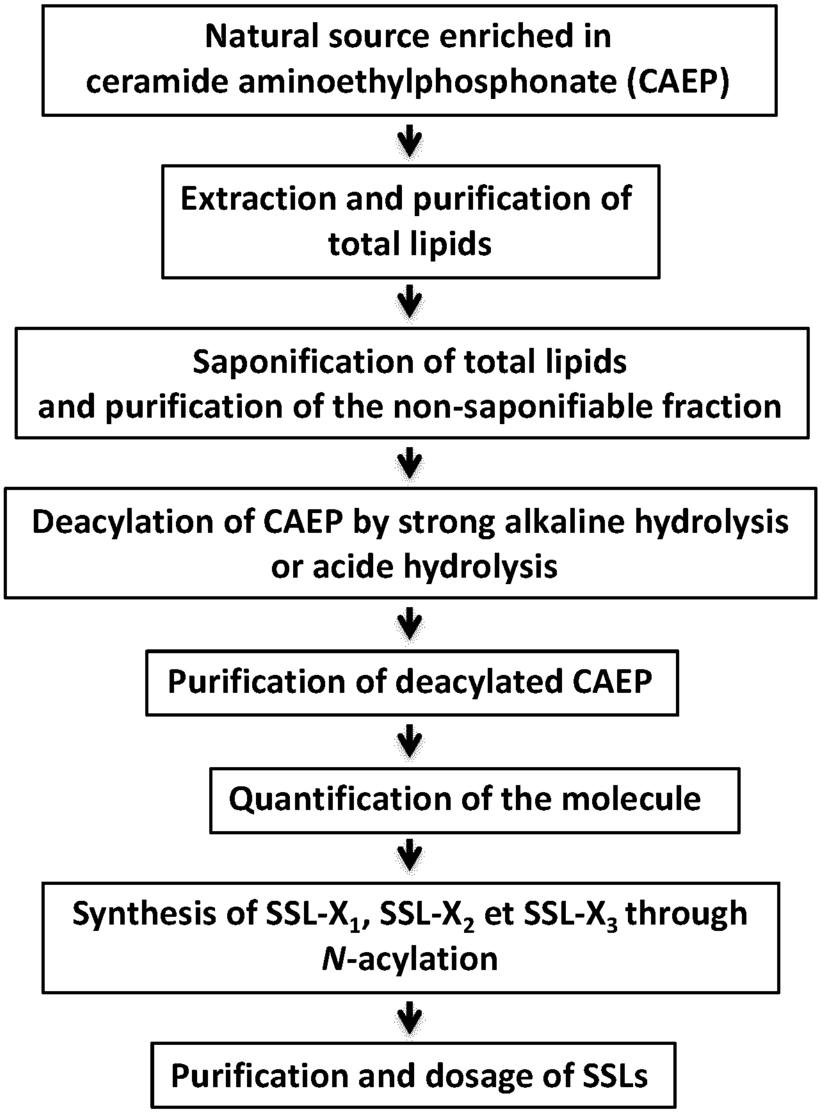

Specification includes a Sequence Listing.

(56) References Cited

FOREIGN PATENT DOCUMENTS

| | | | | |
|---|---|---|---|---|
| WO | WO-9739004 A1 * | 10/1997 | ........... A23K 20/105 |
| WO | WO 00/09139 | 2/2000 | |
| WO | WO-0204467 A1 * | 1/2002 | ........... A61K 31/661 |
| WO | WO-0229001 A2 * | 4/2002 | .............. C07F 9/091 |
| WO | WO-2005115150 A2 * | 12/2005 | .............. C07F 9/091 |
| WO | WO 2012/054528 | 4/2012 | |
| WO | WO 2012/170791 | 12/2012 | |
| WO | WO 2013/158302 | 10/2013 | |
| WO | WO 2014/197880 | 12/2014 | |
| WO | WO 2018/071679 | 4/2018 | |
| WO | WO 2018/162671 | 9/2018 | |
| WO | WO 2019/026230 | 9/2020 | |

OTHER PUBLICATIONS

Lacombe et al Molecular Aspects of Medicine 64 (2018), p. 109-134. https://doi.org/10.1016/j.mam.2017.12.004 Brain docosahexaenoic acid uptake and metabolism. (Year: 2018).*
Tsuboi et al. Inflammation and Regeneration (2018) 38:28, https://doi.org/10.1186/s41232-018-0086-5 Endocannabinoids and related N-acylethanolamines: biological activities and metabolism (Year: 2018).*
Database Registry [Online] Chemical Abstracts Service, Accession No. 419566-81-7, May 21, 2002, p. 1, XP-002798830, Abstract.
Database Caplus [Online] Chemical Abstracts Service, Accession No. 2001:601422, 2001, p. 1, XP-002798831, Abstract.
Written Opinion in International Application No. PCT/EP2020/054662, Jul. 9, 2020, pp. 1-15.
Chintalapati, M. et al. "In Vitro and in Vivo Anti-angiogenic Activities and Inhibition of Hormone-Dependent and -Independent Breast Cancer Cells by Ceramide Methylaminoethylphosphonate" *J. Agric. Food Chem.*, 2009, pp. 5201-5210, vol. 57, No. 12.
De Souza, L. M. et al. "Glyco- and sphingophosphonolipids from the medusa *Phyllorhiza punctata*: NMR and ESI-MS/MS fingerprints" *Chemistry and Physics of Lipids*, 2007, pp. 85-96, vol. 145.
Harokopakis, E. et al. "Conjugation of cholera toxin or its B subunit to liposomes for targeted delivery of antigens" *Journal of Immunological Methods*, 1995, pp. 31-42, vol. 185.
Laye, S. et al. "Anti-Inflammatory Effects of Omega-3 Fatty Acids in the Brain: Physiological Mechanisms and Relevance to Pharmacology" *Pharmacol Rev.*, Jan. 2018, pp. 12-38, vol. 70.
Nguyen, L. N. et al. "Mfsd2a is a transporter for the essential omega-3 fatty acid docosahexaenoic acid" Nature, May 22, 2014, pp. 503-506, vol. 509, supplemental pp. 1-12.
Oshida, K. et al. "Effects of Dietary Sphingomyelin on Central Nervous System Myelination in Developing Rats" Pediatric Research, 2003, pp. 589-593, vol. 53, No. 4.
Rosenthal, A. F. et al. "Inhibition of Phospholipase C by Phosphonate Analogs of Glycerophosphatides" *Biochimica Et Biophysica Acta*, 1968, pp. 226-237, vol. 164.
Sheskin, T. et al. "Structural Requirements for Binding of Anandamide-Type Compounds to the Brain Cannabinoid Receptor" *J. Med. Chem.*, 1997, pp. 659-667, vol. 40, No. 5.
Sinanoglou, V. J. et al. "Structural Analysis of Ceramide-Amino-Ethyl-Phosphonate in Edible Mediterranean Cephalopods" *Acta Alimentaria*, 2004, pp. 359-370, vol. 33, No. 4.
Database File Caplus, "Synthesis of amphiphilic polyunsaturated fatty acids derivatives as effectors of antitumor doxorubicin action" Accession No. 2009:1333855, 2009, p. 1, XP-002798186.
Database File Caplus, "Preparation of novel amides of polyunsaturated fatty acids with cysteamine-S-phosphate as cytotoxic agents" Accession No. 2002:51479, 2002, pp. 1-3, XP-002798187.
Database File Caplus, "Synthesis and biological evaluation of novel cytotoxic phospholipids for prostate cancer" Accession No. 2004:729849, 2004, p. 1, XP-002798188.
Database File Caplus, "Preparation of novel amides of polyunsaturated fatty acids with cysteamine-S-phosphate as cytotoxic agents" Accession No. 2002:51479, 2002, pp. 1-2, XP-002798189.
Database File Caplus, "Synthesis of micelle-forming phosphoethanolamides of unsaturated fatty acids" Accession No. 2001:601422, 2001, pp. 1-3, XP-002798190.
Database File Caplus, "Formation of N-(hexanoyl)ethanolamine, a novel phosphatidylethanolamine adduct, during the oxidation of erythrocyte membrane and low-density lipoprotein" Accession No. 2004:1154076, 2004, p. 1, XP-002798191.
Database File Caplus, "Molecular organization and stability of hydrated dispersions of headgroup-modified phosphatidylethanolamine analogs" Accession No. 1991:444615, 1991, p. 1, XP-002798192.
Database File Caplus, "Primary or secondary alcohol derivatives of phospholipids produced by the enzymic technique" Accession No. 1985:77260, 1985, pp. 1-2, XP-002798193.
Database File Caplus, "Synthesis of DL-phosphatidylpropanolamine. II. DL-2-O-(DL-Dipalmitoylglycerylphosphoryl)-1-aminoisopropanol" Accession No. 1972:71940, 1972, p. 1, XP-002798194.
Schandock, F. et al. "Macromolecular Antiviral Agents against Zika, Ebola, SARS, and Other Pathogenic Viruses" *Advanced Healthcare Materials*, 2017, pp. 1-14, vol. 6, No. 1700748.
Tellman, K.T. et al. "Polymers of sodium-N-undec-10-ene-1-oyl taurate and sodium-N-undec-10-ene-1-oyl aminoethyl-2-phosphonate as pseudostationary phases for electrokinetic chromatography" *Electrophoresis*, 1999, pp. 152-161, vol. 20.
CAS Registry No. 221638-61-5, Jan. 20, 2023, pp. 1-3.
Cioni, J. P. et al. "Cyanohydrin Phosphonate Natural Product from *Streptomyces regensis*" *Journal of Natural Products*, 2014, pp. 243-249, vol. 77.

* cited by examiner

STRUCTURED MOLECULAR VECTORS FOR ANTI-INFLAMMATORY COMPOUNDS AND USES THEREOF

CROSS-REFERENCE TO RELATED APPLICATION

This application is the U.S. national stage application of International Patent Application No. PCT/EP2020/054662, filed Feb. 21, 2020.

REFERENCE TO SEQUENCE LISTING

The Sequence Listing for this application is labeled "Seq-List.txt" which was created on Jul. 1, 2021 and is 3,540 bytes. The entire content of the sequence listing is incorporated herein by reference in its entirety.

FIELD OF THE INVENTION

The present invention relates to vector compounds of different biologically active compounds having, in particular, strong anti-inflammatory properties, enabling the restoration of the cognition and prevention of the cognitive decline and/or the decrease of seizures severity and frequency. It also relates to the use of such compounds in the treatment of neurological, psychiatric and peripheral types disorders, and particularly disorders having an inflammatory origin. The present invention also relates to ethanolamine, ethanolamine-phosphonate and ethanolamine-phosphate fatty acid derivatives and the use thereof in the same therapeutic and non-therapeutic applications.

BACKGROUND OF THE INVENTION

Considering their numerous virtues, omega-3 fatty acid type compounds represent an important market in the health domain. Indeed, these compounds are active in the prevention of numerous diseases, which have inflammation for a common denominator. Inflammation is a constitutive component of many diseases or disorders, such as articular, cardiovascular, as well as neurological disorders.

Omega-3 compounds currently found on the market are limited down to two families of the fatty acid vectors, which are the ethyl form and triglyceride form. On the pharmacological aspect, the ethyl form is relatively inefficient, partially due to its poor biodisponibility and its poor cerebral tropism. The triglyceride form, which is the most current vectorization form on the market today, also exhibits contradictory results in the terms of efficacy and cerebral tropism.

A new type of omega-3 fatty acid vector has thus appeared on the market. These glycerophospholipid type vectors have the advantage of a better cerebral accumulation when compared to ethyl- and triglyceride form vectors. However, these glycerophospholipids form vectors are generally obtained from the total extracts, like a total krill extract that is impure on the molecular level. In addition, the use of these glycerophospholipid forms obtained from krill extract, raises the questions of the environmental and sustainable development as they contribute to the scarcity of fishery resources.

The glycerophospholipid vectors of omega-3 fatty acids developed are, for instance, phosphatidylserine vectors. A further one is a vector that mimics lysophosphatidylcholine for a particular family of omega-3 fatty acids including docosahexaenoic acid or DHA (WO 2018/162617). Although glycerophospholipid based vectors have a better cerebral targeting than ethyl and triglyceride form-based vectors, they have the inconvenience of being monovalent vectors of fatty acids (ex: docosahexaenoic acid only), with short-term delivery only.

Thus, there is nowadays a strong need to develop new vector compounds that allow delivery of one or more active compounds, like fatty acids, in the acute (short term) and prolonged (long term) fashion, along the digestive tract, in order to provide effective treatments, not only in the cases of inflammation and epileptic seizures, but also in the preservation and/or restoration of cognitive functions associated or not with behavioral and/or psychoaffective disorders. Also, the development of fatty acid derivatives remains an important need in these applications.

SUMMARY OF THE INVENTION

The inventors have developed a new family of molecular vectors and new active compounds, especially ethanolamine, ethanolamine-phosphonate or ethanolamine-phosphate derivative of saturated or unsaturated fatty acids. The active compounds have strong anti-inflammatory activity, and can decrease seizure severity and frequency and/or restore or improve cognitive functions, which may be altered in neurological disorders with a significant inflammatory component. The new family of molecular vectors includes two subfamilies, namely SphingoSynaptoLipoxins (SSLs) and AminoGlyceroPhosphoSynaptoLipoxins (AGPSLs).

Accordingly, the present invention relates to a compound of formula (I):

(I)

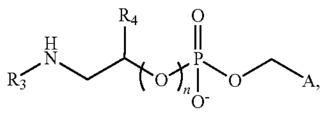

in which:

n is a whole number equal to 0 or 1;

A represents a radical chosen among:

a group of formula (A'):

(A')

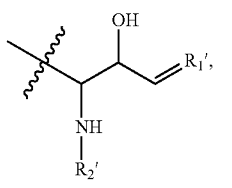

in which:

$R_{1'}$ represents a saturated or unsaturated $(C_1\text{-}C_{24})$alkyl chain optionally substituted by at least one group chosen among a hydroxyl and a halogen; and $R_{2'}$ represents a hydrogen, a saturated or unsaturated fatty acyl comprising from 2 to 30 carbon atoms, one of its oxygen derivatives, or a biologically active compound bound to the rest of the molecule by an acyl group; or a group of formula (A"):

(A")

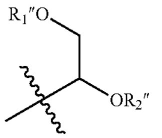

in which:

$R_{1''}$ represents a fatty acyl, preferably saturated, comprising from 2 to 30 carbon atoms; and $R_{2''}$ represents a hydrogen, a saturated or unsaturated fatty acyl comprising from 2 to 30 carbon atoms, one of its oxygen derivatives, or a biologically active compound bound to the rest of the molecule by an acyl group;

$R_3$ represents a hydrogen, a saturated or unsaturated fatty acyl comprising from 2 to 30 carbon atoms, one of its oxygen derivatives, or a biologically active compound bound to the rest of the molecule by an acyl group; and $R_4$ represents a hydrogen or a $(C_1\text{-}C_6)$alkyl group; and the hydrates, or the diastereoisomers, or the pharmacologically acceptable salts thereof.

In a particular embodiment, a compound of the invention has the formula (I'):

(I')

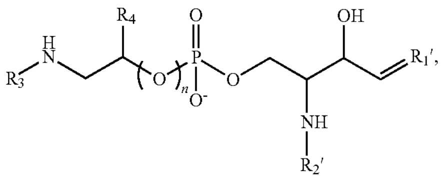

in which:

n is a whole number equal to 0 or 1;

$R_{1'}$ represents a saturated or unsaturated $(C_1\text{-}C_{24})$alkyl chain optionally substituted by at least one group chosen among a hydroxyl and a halogen;

$R_{2'}$ represents a hydrogen, a saturated or unsaturated fatty acyl comprising from 2 to 30 carbon atoms, one of its oxygen derivatives, or a biologically active compound bound to the rest of the molecule by an acyl group;

$R_3$ represents a hydrogen, a saturated or unsaturated fatty acyl comprising from 2 to 30 carbon atoms, one of its oxygen derivatives, or a biologically active compound bound to the rest of the molecule by an acyl group; and $R_4$ represents a hydrogen or a $(C_1\text{-}C_6)$alkyl group, preferably a methyl group.

In a further particular embodiment, a compound of the invention has the formula (I"):

(I")

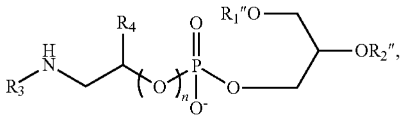

in which:

n is a whole number equal to 0 or 1;

$R_{1''}$ represents a fatty acyl, preferably saturated, comprising from 2 to 30 carbon atoms;

$R_{2''}$ represents a hydrogen, a saturated or unsaturated fatty acyl comprising from 2 to 30 carbon atoms, one of its oxygen derivatives, or a biologically active compound bound to the rest of the molecule by an acyl group;

$R_3$ represents a hydrogen, a saturated or unsaturated fatty acyl comprising from 2 to 30 carbon atoms, one of its oxygen derivatives, or a biologically active compound bound to the rest of the molecule by an acyl group; and $R_4$ represents a hydrogen or a $(C_1\text{-}C_6)$alkyl group, preferably a methyl group.

In a preferred embodiment, $R_3$ of formulae (I), (I'), and (I") is not a hydrogen.

In a preferred embodiment, $R_{2'}$, $R_{2''}$ and $R_3$ of formulae (I), (I'), and (I") are such that:

$R_{2'}$ and $R_{2''}$ represent independently:

a hydrogen, a saturated or unsaturated fatty acyl comprising from 2 to 30 carbon atoms selected in the group consisting of: acetic acid, propionic acid, butyric acid, valeric acid, caprylic acid, capric acid, lauric acid, myristic acid, palmitic acid, stearic acid, arachidic acid, behenic acid, lignoceric acid, myristoleic acid, palmitoleic acid, oleic acid, vaccenic acid, linoleic acid, alpha-linoleic acid, arachidonic acid, eicosapentaenoic acid, erucic acid, and docosahexaenoic acid, preferably docosahexaenoic acid, or an oxygen derivative of a saturated or unsaturated fatty acyl comprising from 2 to 30 carbon atoms chosen from resolvins, maresins, neuroprotectins and neuroprostanes; and $R_3$ represents:

a saturated or unsaturated fatty acyl comprising from 2 to 30 carbon atoms selected in the group consisting of: acetic acid, propionic acid, butyric acid, valeric acid, caprylic acid, capric acid, lauric acid, myristic acid, palmitic acid, stearic acid, arachidic acid, behenic acid, lignoceric acid, myristoleic acid, palmitoleic acid, oleic acid, vaccenic acid, linoleic acid, alpha-linoleic acid, arachidonic acid, eicosapentaenoic acid, erucic acid, and docosahexaenoic acid, preferably docosahexaenoic acid, or an oxygen derivative of a saturated or unsaturated fatty acyl comprising from 2 to 30 carbon atoms chosen from resolvins, maresins, neuroprotectins and neuroprostanes.

The present invention further relates to an ethanolamine, ethanolamine-phosphonate or ethanolamine-phosphate derivative of a saturated or unsaturated fatty acid comprising from 2 to 30 carbon atoms or one of its oxygen derivatives, which can be delivered by the vectors as disclosed herein.

Accordingly, the present invention also relates to a compound of formula (II):

$$R_5\text{—NH—}CH_2\text{—}CH(R_7)\text{—}O_{(n)}\text{—}R_6 \quad \text{(II)},$$

in which:

n is a whole number equal to 0 or 1;

$R_5$ represents a saturated or unsaturated fatty acyl comprising from 2 to 30 carbon atoms or one of its oxygen derivatives; and $R_6$ is a $—PO_3^{2-}$ group;

$R_7$ represents a hydrogen or a $(C_1\text{-}C_6)$alkyl group;

with the proviso that when n is equal to 1, then $R_5$ is not an arachidonic acid; and the hydrates, or the diastereoisomers, or the pharmacologically acceptable salts thereof.

In a preferred embodiment, a compound of formula (II) is such that:

n is a whole number equal to 0;

$R_5$ represents a saturated or unsaturated fatty acyl comprising from 2 to 30 carbon atoms, which is docosahexaenoic acid; and $R_7$ represents a hydrogen.

In a further preferred embodiment, $R_5$ represents:

a saturated or unsaturated fatty acyl comprising from 2 to 30 carbon atoms selected in the group consisting of: acetic acid, propionic acid, butyric acid, valeric acid, caprylic acid, capric acid, lauric acid, myristic acid, palmitic acid, stearic acid, arachidic acid, behenic acid, lignoceric acid, myristoleic acid, palmitoleic acid, oleic acid, vaccenic acid, linoleic acid, alpha-linoleic acid, arachidonic acid, eicosapentaenoic acid, erucic acid, and docosahexaenoic acid, preferably capric acid, eicosapentaenoic acid, and docosahexaenoic acid, or an oxygen derivative of a saturated or unsaturated fatty acyl comprising from 2 to 30 carbon atoms chosen from resolvins, maresins, neuroprotectins, and neuroprostanes.

A further object of the invention is a compound of formula (I), (I'), (I") or (II), for use as a medicine.

A further object of the invention is a use of a compound of formula (I), (I'), (I") or (II) as a food supplement.

The present invention further relates to a pharmaceutical composition comprising at least one compound of formula (I), (I'), (I") or (II), and an acceptable pharmaceutical excipient.

A particular embodiment of the invention is a pharmaceutical composition as disclosed herein for use for preventing and/or treating a disease chosen among an inflammatory disease or a disease associated with a cognitive disorder. Preferably, the inflammatory disease is an inflammatory disease of the central nervous system, an inflammatory disease of the digestive tract, an inflammatory joint disease, or an inflammatory disease of the retina.

A further particular embodiment of the invention is a pharmaceutical composition as disclosed herein for use for preventing and/or treating a disease selected in the group consisting of epilepsy, traumatic brain injury, Alzheimer's disease, Parkinson's disease, Multiple Sclerosis, Crohn's Disease, Bowel's Syndrome, Dementia, and Huntington's Disease.

A further particular embodiment of the invention is a pharmaceutical composition as disclosed herein for use for preventing cognitive decline or restoring cognitive functions altered in brain injuries or damages, and/or in traumatic brain injuries, and/or in a neuroinflammatory disease and/or in a neurodegenerative disease.

Another object of the invention is a pharmaceutical composition comprising an acceptable pharmaceutical excipient and a compound of formula (II'):

$$R_{5'}\text{—NH—}CH_2\text{—}CH(R_{7'})\text{—}O_{(n)}\text{—}R_{6'} \quad \text{(II)},$$

wherein:

n is a whole number equal to 1;

$R_{5'}$ represents a saturated or unsaturated fatty acyl comprising from 2 to 30 carbon atoms or one of its oxygen derivatives;

$R_{6'}$ is a hydrogen; and $R_{7'}$ represents a hydrogen or a $(C_1\text{-}C_6)$alkyl group; and the hydrates, or the diastereoisomers, or the pharmacologically acceptable salts thereof; for use for preventing and/or treating a disease associated with a cognitive or a disease selected in the group consisting of epilepsy, traumatic brain injury, Alzheimer's disease, Parkinson's disease, Multiple Sclerosis, Crohn's Disease, Bowel's Syndrome, Dementia, and Huntington's Disease.

Another object of the invention is a pharmaceutical composition comprising an acceptable pharmaceutical excipient and a compound of formula (II') as above defined, for use for preventing cognitive decline or restoring cognitive functions altered in brain injuries and/or in traumatic brain injuries and/or in a neuroinflammatory disease, and/or in a neurodegenerative disease.

In a preferred embodiment, $R_{5'}$ represents a saturated or unsaturated fatty acyl comprising from 2 to 30 carbon atoms selected in the group consisting of: acetic acid, propionic acid, butyric acid, valeric acid, caprylic acid, capric acid, lauric acid, myristic acid, palmitic acid, stearic acid, arachidic acid, behenic acid, lignoceric acid, myristoleic acid, palmitoleic acid, oleic acid, vaccenic acid, linoleic acid, alpha-linoleic acid, arachidonic acid, eicosapentaenoic acid, erucic acid, and docosahexaenoic acid, preferably capric acid, eicosapentaenoic acid, and docosahexaenoic acid, or an oxygen derivative of a saturated or unsaturated fatty acyl comprising from 2 to 30 carbon atoms chosen from resolvins, maresins, neuroprotectins, and neuroprostanes.

According to a preferred embodiment, the pharmaceutical compositions as disclosed herein are administered by oral route.

LEGEND OF THE FIGURES

FIG. 1: General procedure for the preparation of SSL-Xs compounds

Figure 2:
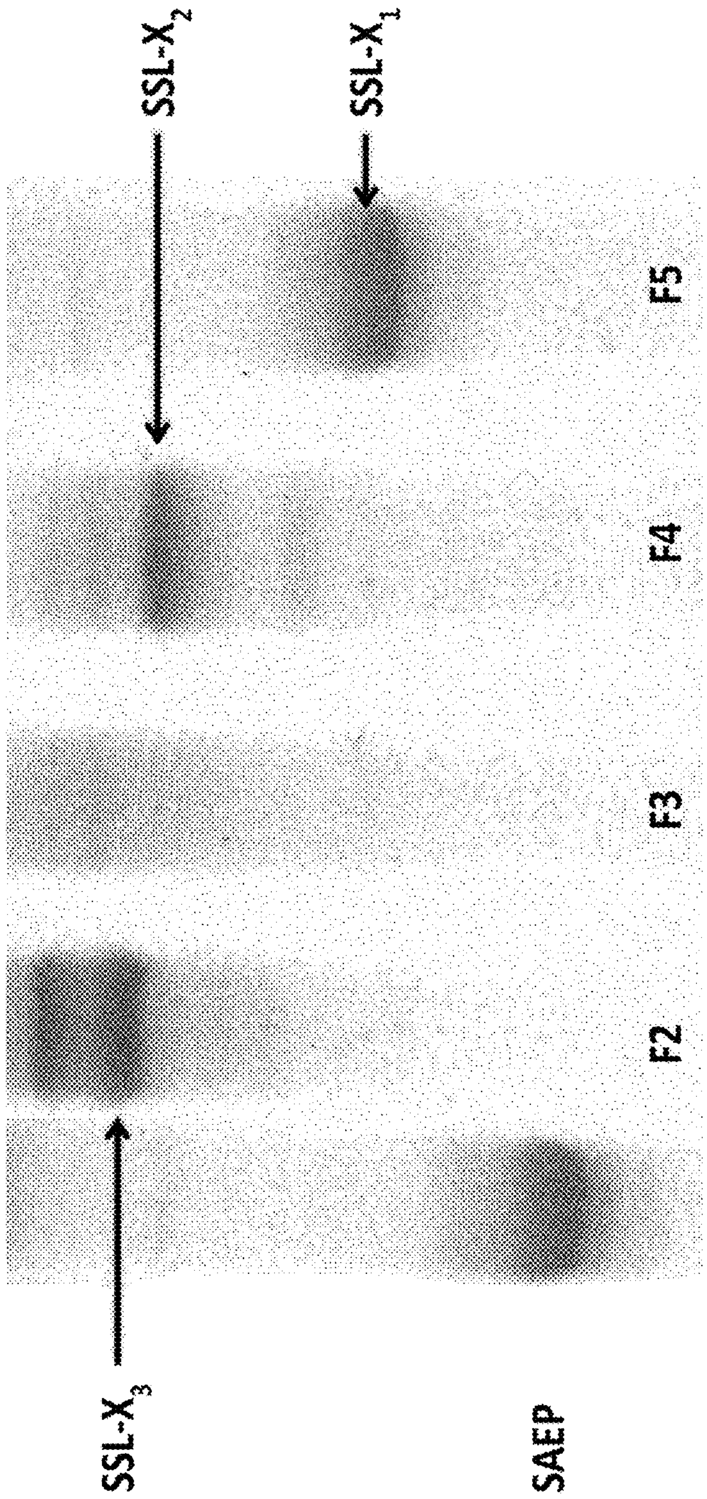

FIG. 2: Separation of SSL-X1, SSL-X2 and SSL-X3 on an aminopropyl (LC-NH2) column.

Figure 3:
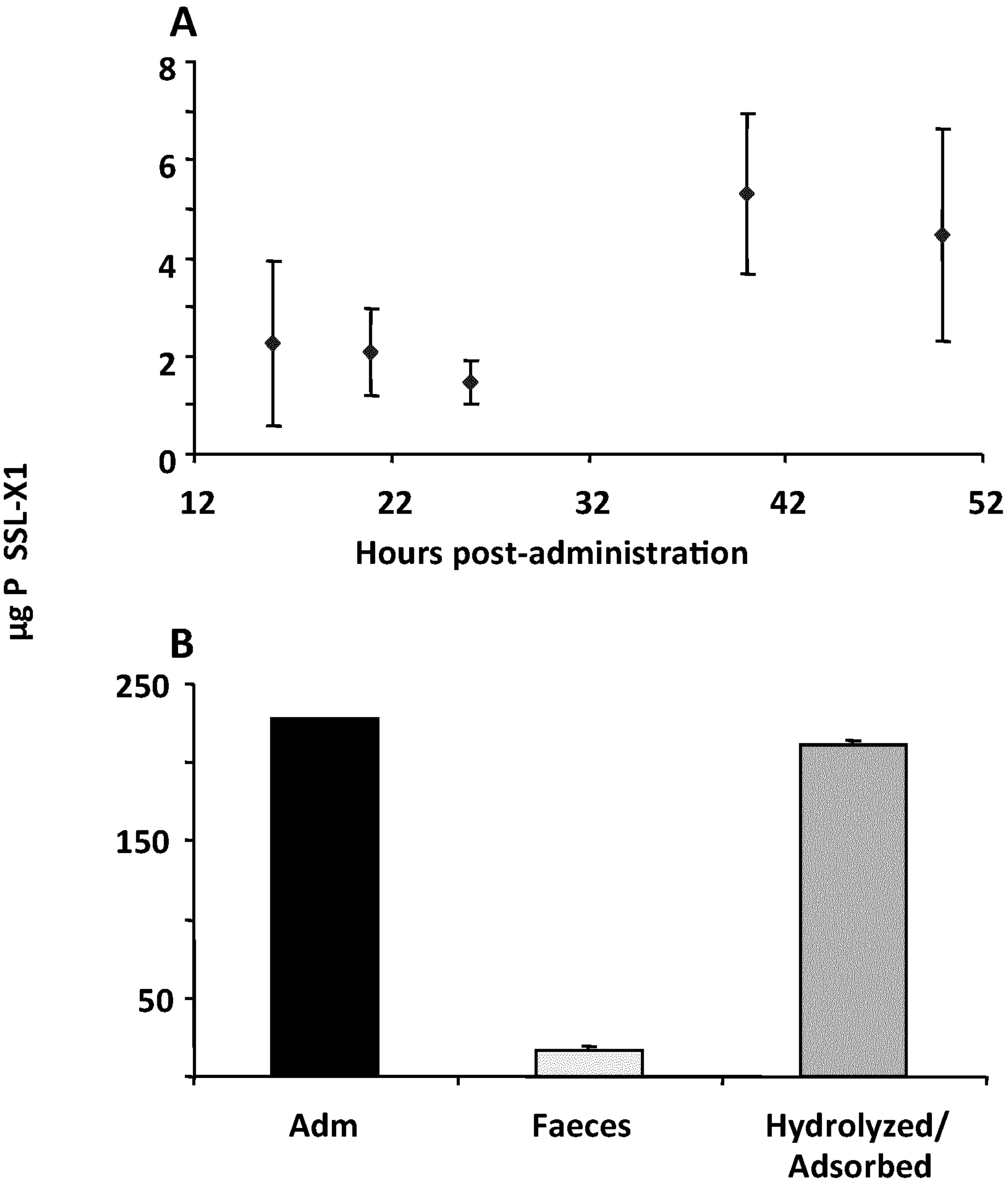

FIG. 3: Hydrolysis of SSL-X1 in the digestive tract.

Each animal was given per os 227 µg of SSL-X1 and faeces were collected after 16, 21, 26, 40, and 50 hours. A: Amount of SSL-X1 measured in the faeces at the different time points.

B: administered quantities of molecule (Adm), total quantity measured in faeces at different time points (Faeces), and hydrolyzed/adsorbed quantity (hydrolyzed/adsorbed). These quantities expressed in µg of phosphorus (P) in SSL-X1 were calculated with the presumption that quantity of SSL-X1 (hydrolyzed/adsorbed) corresponds to the administered quantity minus measured quantity accumulated in the total of faeces. Results are the average standard deviation of 5 independent experiments.

Figure 4:
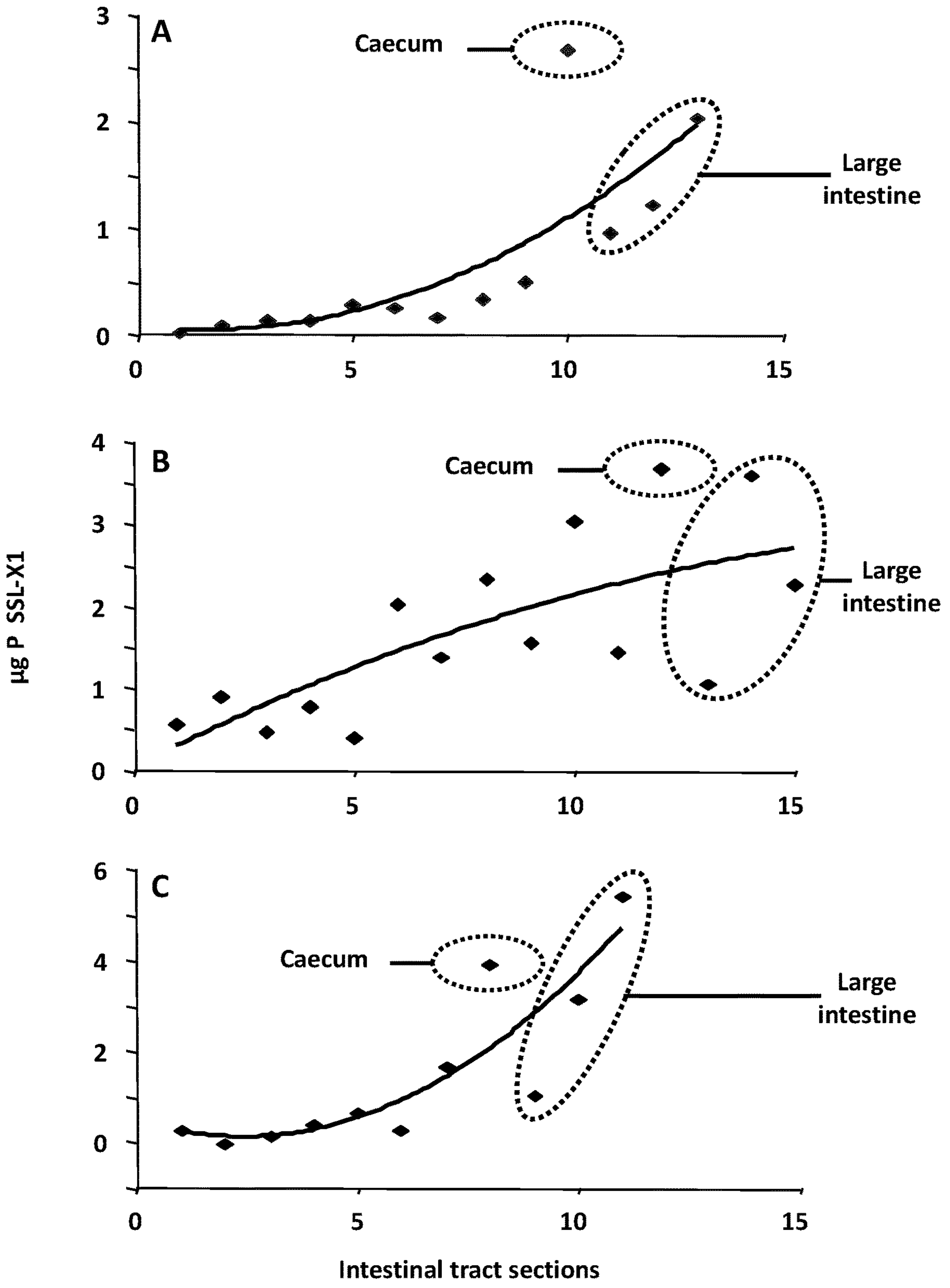

FIG. 4: Time dependent distribution of SSL-X1 along the intestinal tract of treated rats Each animal was given per os 227 µg of SSL-X1. Rats were sacrificed 5 hours (panel A), 8 hours (panel B) and 36 hours (panel C) after administration of the molecule. The intestinal tract was removed and sectioned every ~10 cm. The content of each section is collected and the lipids extracted as described and purified. The amount of SSL-X1 in each lipid extract is determined by phosphorus determination.

Figure 5:
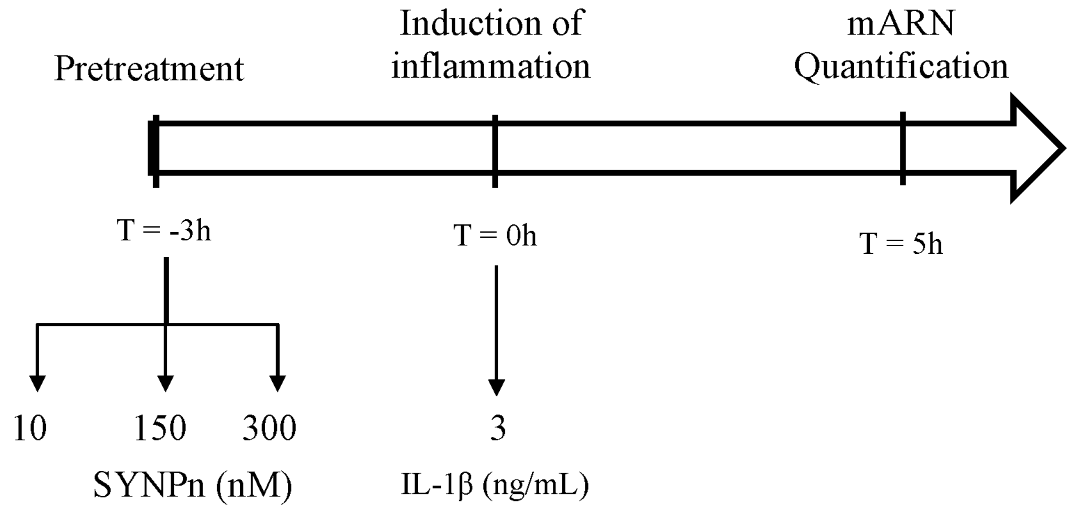

FIG. 5: Protocol to test the effect of synaptamide phosphonate on the expression of inflammation markers in human microglia activated by IL-1β.

Figure 6:
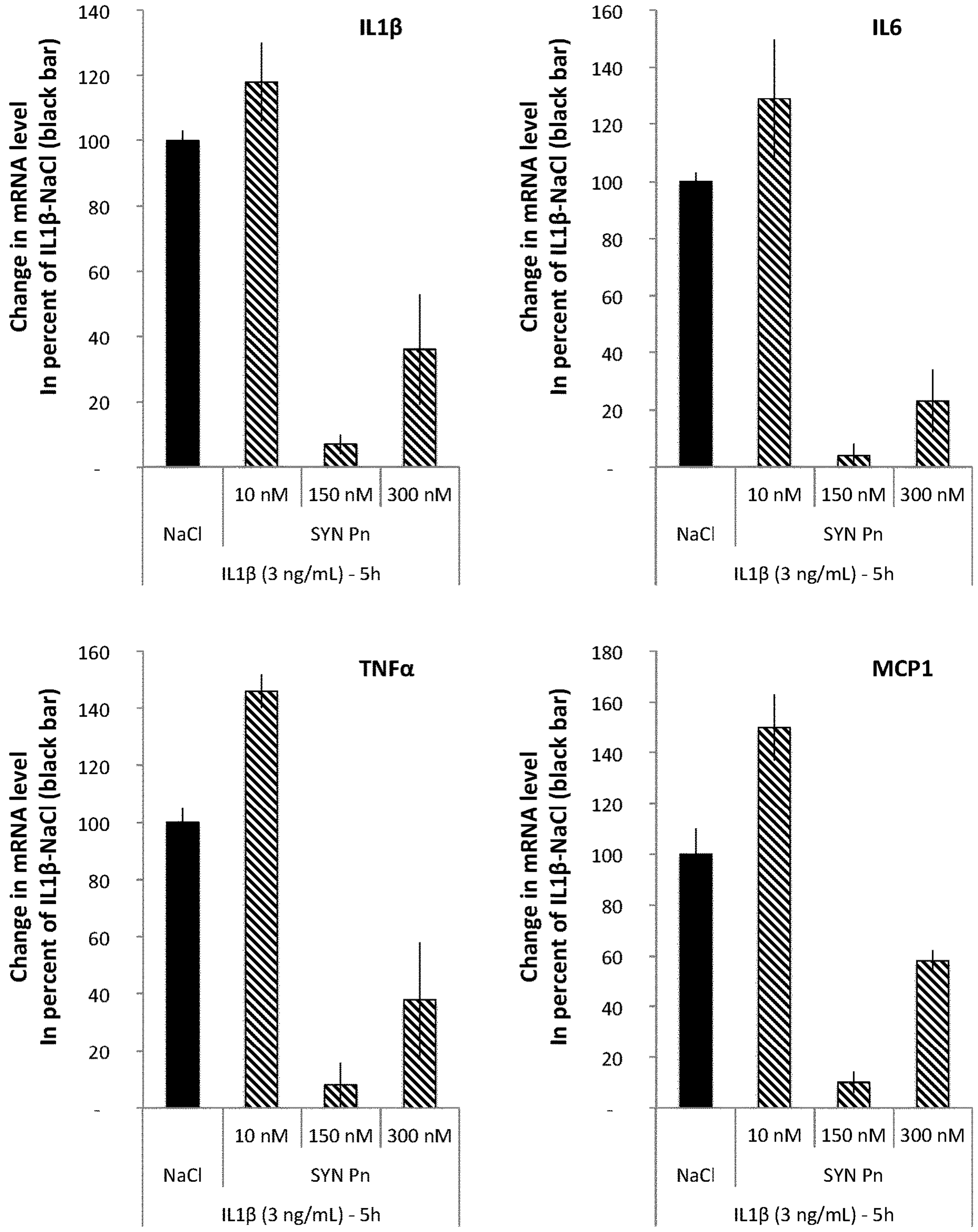

FIG. 6: Synaptamide phosphonate (SYN Pn) reduces the IL-1β-mediated induction of pro-inflammatory markers in immortalized human microglial cells. IHM microglial cells were treated 3 hours before exposure to IL-1β by SYN Pn at different concentrations as shown in the Figure. RNAs from inflammation markers were extracted 5 hours after IL-1β-treatment and quantified by RT-qPCR. The results are expressed as % of (IL-1β-NaCl) ±SEM (n=3).

Figure 7:
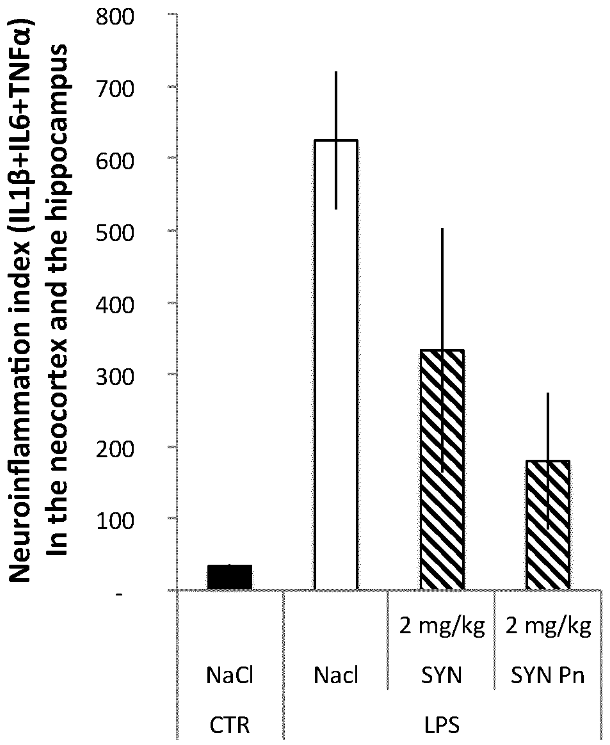

FIG. 7: In vivo effect of Synaptamide and Synaptamide Phosphonate on LPS-induced neuroinflammation in rats. LPS was injected into 21-day-old pups. One minute after LPS injection, the animals received Synaptamide (SYN) or synaptamide phosphonate (SYN Pn) at a dose of 2 mg/Kg synaptamide equivalent. The rats were sacrificed 6 hours after the injection of LPS and the hippocampus and the neocortex were collected. The expression levels of the inflammation marker transcripts were determined by RT-qPCR. IL1β: Interleukin 1 beta; IL6: interleukin 6; TNFα: TNF alpha. Neuroinflammation index (IN) determined from data obtained in the hippocampus and neocortex. CTR: control rats. The results are expressed as mean±SEM (n=5).

Figure 8:
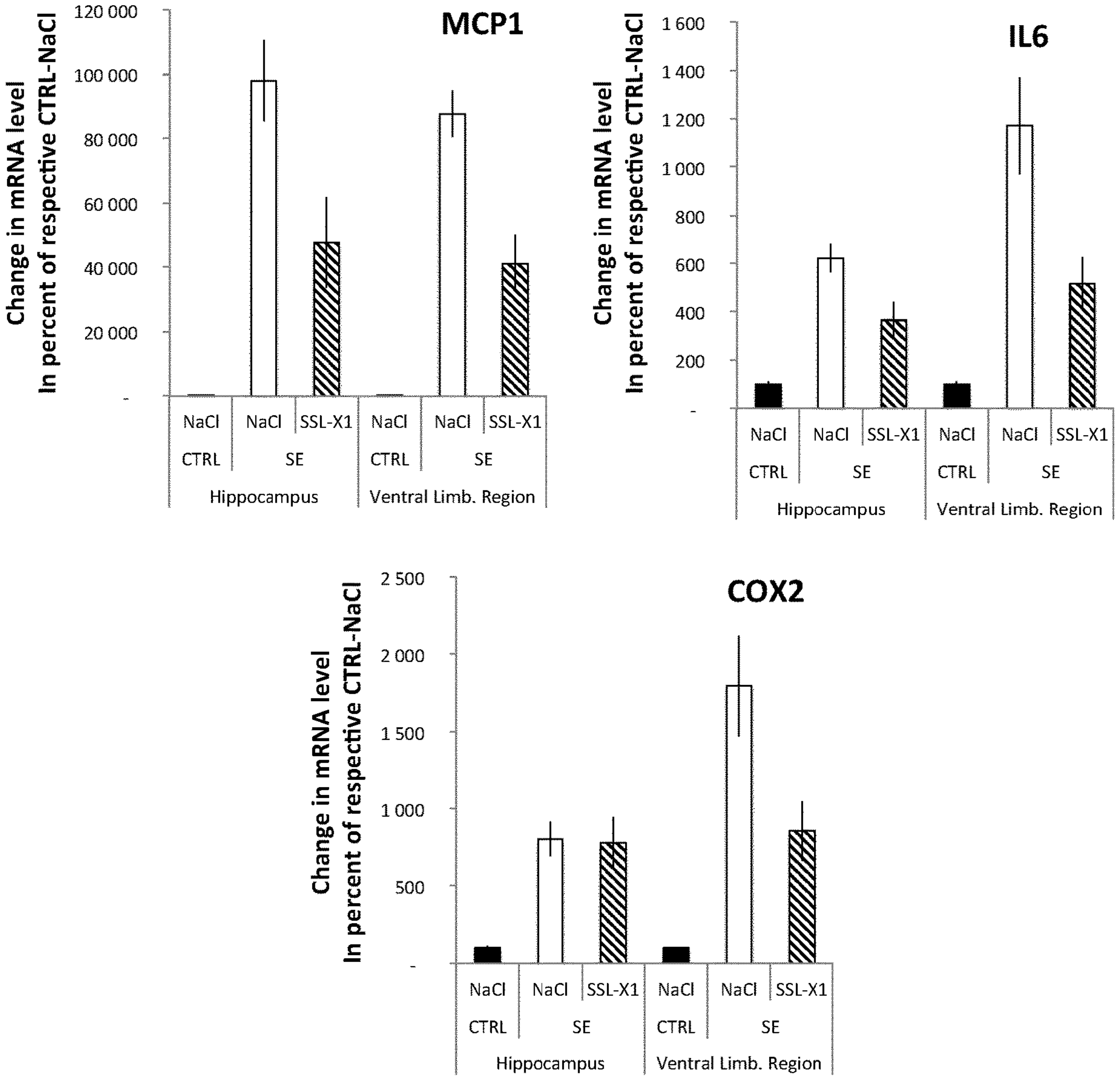

FIG. 8: Effect of the SSL-X1 vector on SE-induced neuroinflammation in rats. 21 day-old rats were subjected to SE. The SSL-X1 vector was administered per os 1 hour after the onset of SE. Brain structures of interest (hippocampus and ventral limbic area) were collected 24 hours after SE. The mRNA levels of interleukin 6 (IL6), cyclooxygenase 2 (COX2) and chemokine MCP1 (MCP1) were determined by RT-qPCR. CTRL: Controls administered with NaCl; SE-NaCl: group of rats subjected to SE and administered with NaCl; SE-SSL-X1: group of rats subjected to SE and administered with the vector SSL-X1; HI: hippocampus; VLR: ventral limbic region. The results are expressed as the mean±SEM (n=7-10).

Figure 9:
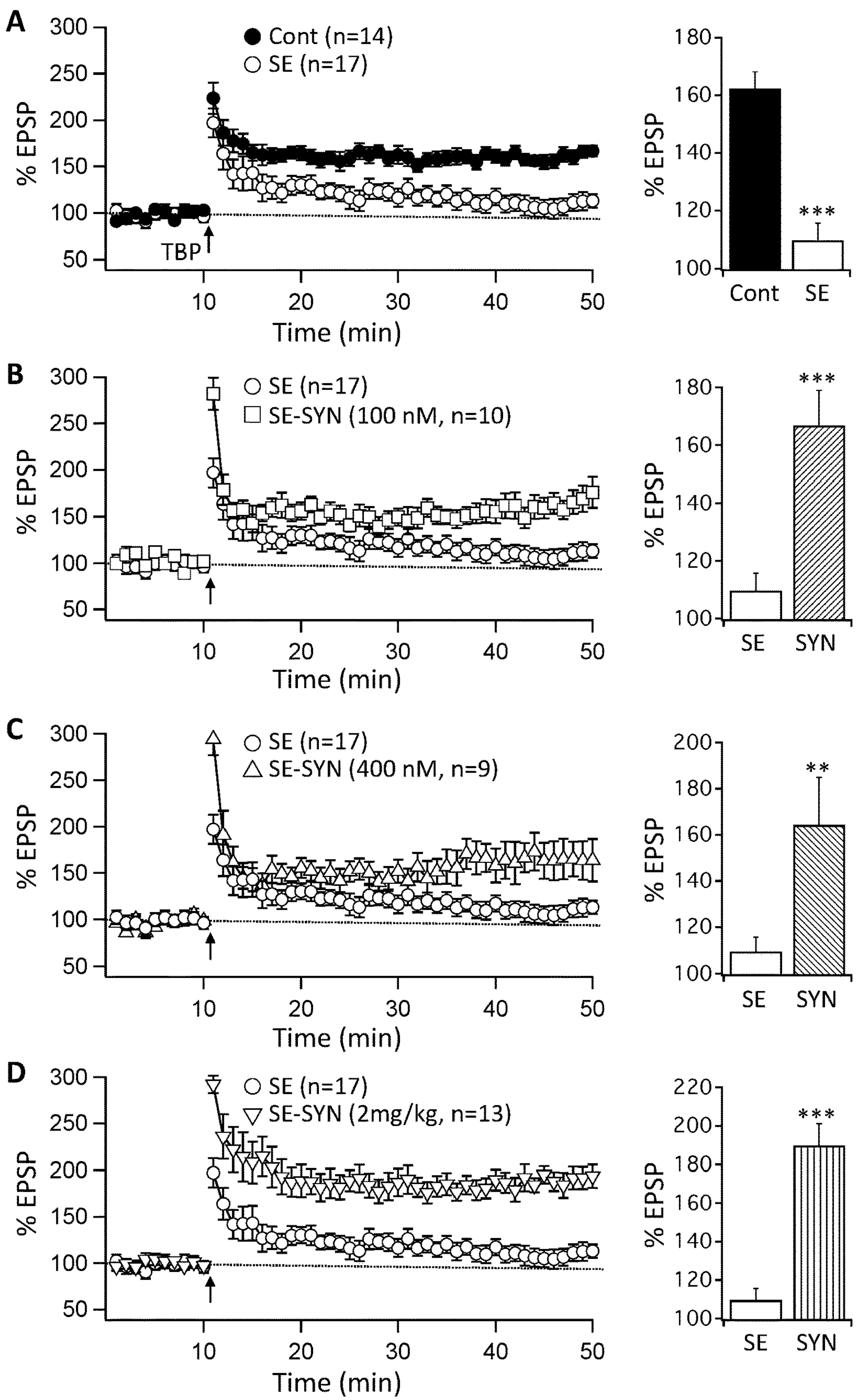
Figure 9:
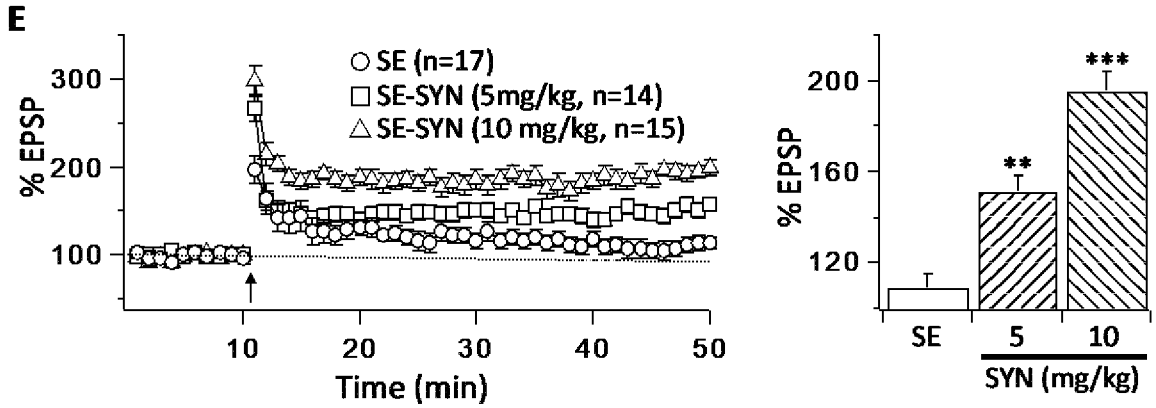

FIG. 9: Hippocampal LTP is attenuated 1 to 2 weeks following Pilo-SE and rescued by synaptamide. FIG. 9A: Summary time course (left) of excitatory postsynaptic potentials (EPSPs) amplitudes before and after Long-Term Potentiation (LTP) induction by Theta Burst Pairing protocol stimulation (TBP, indicated by arrow) in hippocampal slices from healthy rats (Cont) and animals subjected to Pilo-SE (SE). FIGS. 9B-C: LTP induction (left) in hippocampal slices from rats subjected to Pilo-SE and perfused either with Synaptamide-free Artificial CerebroSpinal fluid (ACSF) (SE) or Synaptamide (SE-SYN) at 100 nM (B) and 400 nM (C). FIG. 9D: LTP induction (left) in hippocampal slices from rats subjected to Pilo-SE and injected either with NaCl (SE) or synaptamide (SE-SYN, 2 mg/kg; i.p). FIG. 9E: LTP induction (left) in hippocampal slices from rats subjected to Pilo-SE and injected (i.p) either with NaCl (SE) or synaptamide (SE-SYN) at 2 or 10 mg/kg. Synaptamide was administered 1 h after cessation of SE, and then each day during 6 days. Control groups received saline solution only. In this and all subsequent figures, summary data are presented as mean±SEM, numbers between brackets indicate the number of cells and histograms (right) show the mean amplitude (±SEM) of EPSPs measured during the last 5 minutes of recording in each condition. *p<0.05, p<0.01, *p<0.001.

Figure 10:
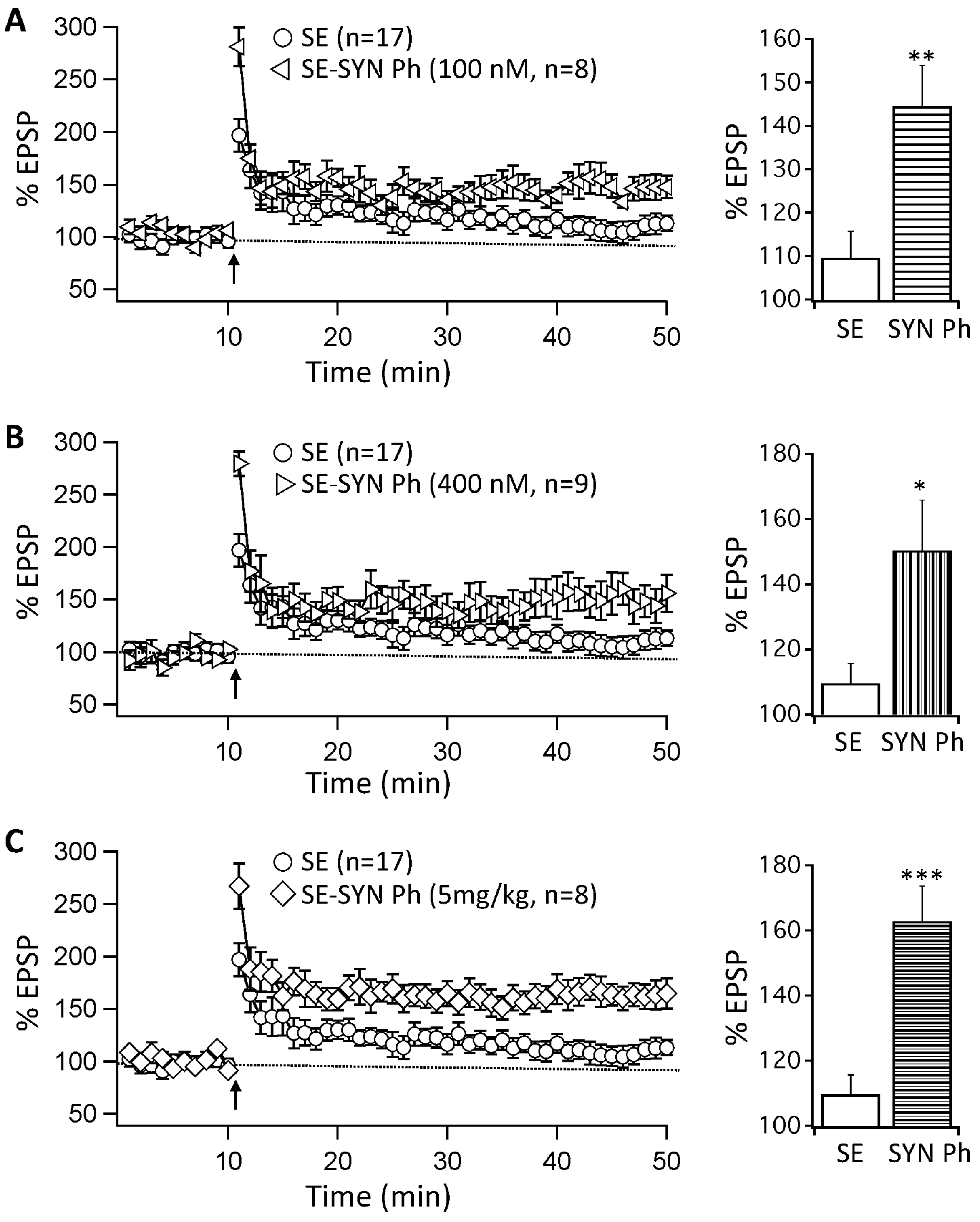
Figure 10:
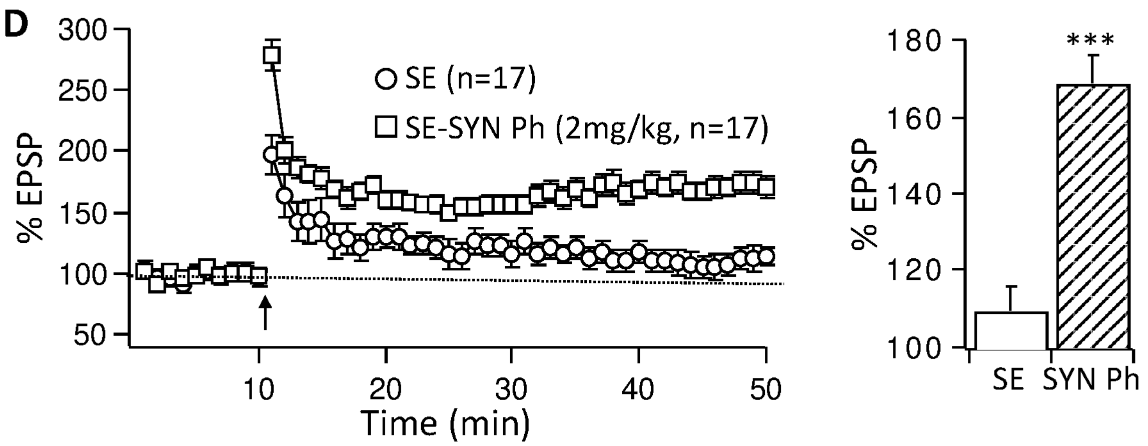

FIG. 10: Hippocampal LTP is rescued by synaptamide phosphate 1 to 2 weeks following Pilo-SE FIG. 10A-B: LTP induction in hippocampal slices from rats subjected to Pilo-SE and perfused either with Synaptamide phosphate-free ACSF (SE) or Synaptamide phosphate (SE-SYN Ph) at 100 nM (A) and 400 nM (B). FIG. 10C: LTP induction in hippocampal slices from rats subjected to Pilo-SE and injected either with NaCl (SE) or synaptamide phosphate (SE-SYN Ph, 5 mg/kg; i.p). FIG. 10D: LTP induction (left) in hippocampal slices from rats subjected to Pilo-SE and injected (i.p) either with NaCl (SE) or synaptamide phosphate (SE-SYNPh) at 2 mg/kg. Synaptamide phosphate was administered 1 h after cessation of SE, and then each day during 6 days. Control groups received saline solution only. *p<0.05, p<0.01, *p<0.001.

Figure 11:
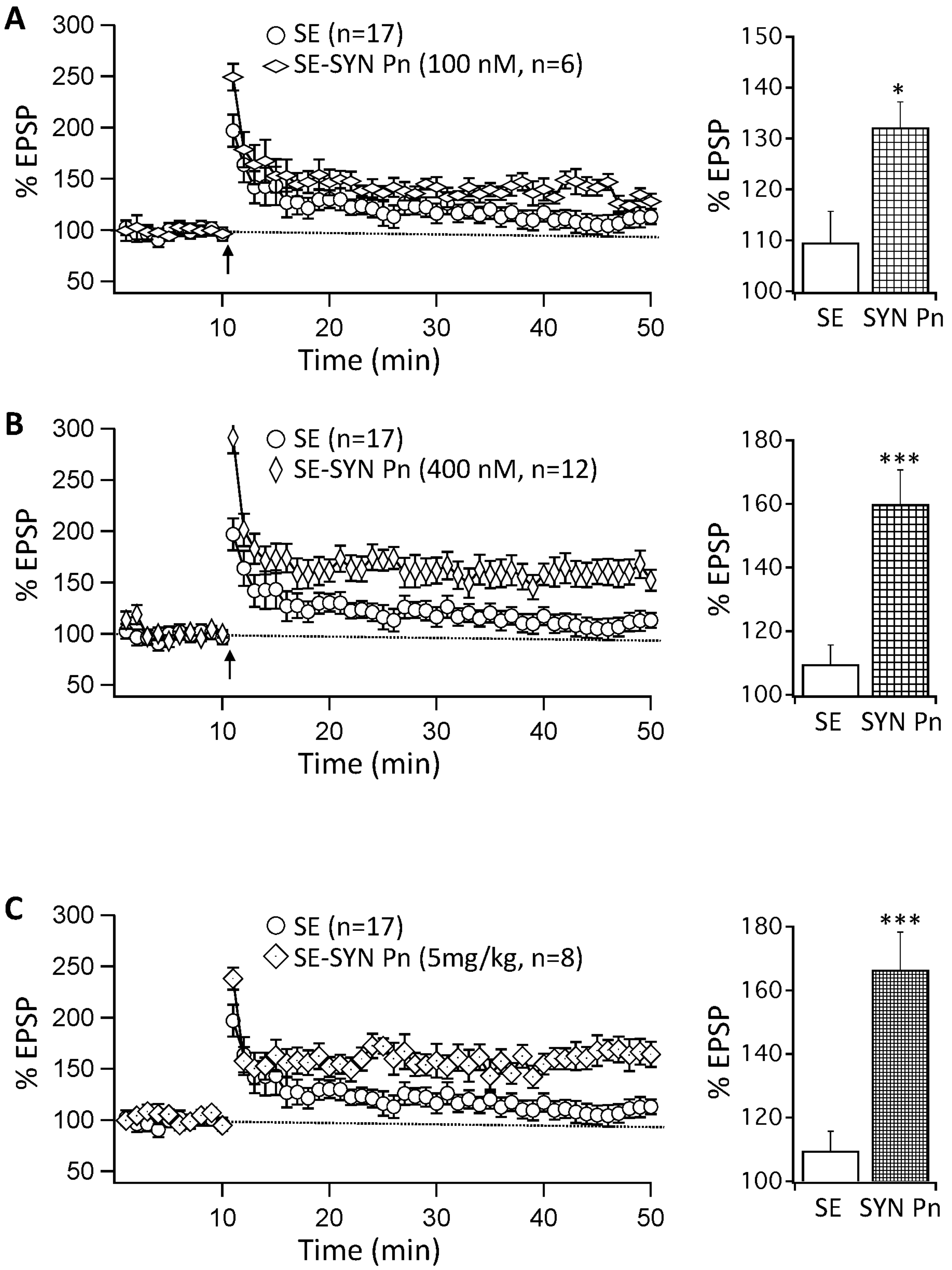
Figure 11:
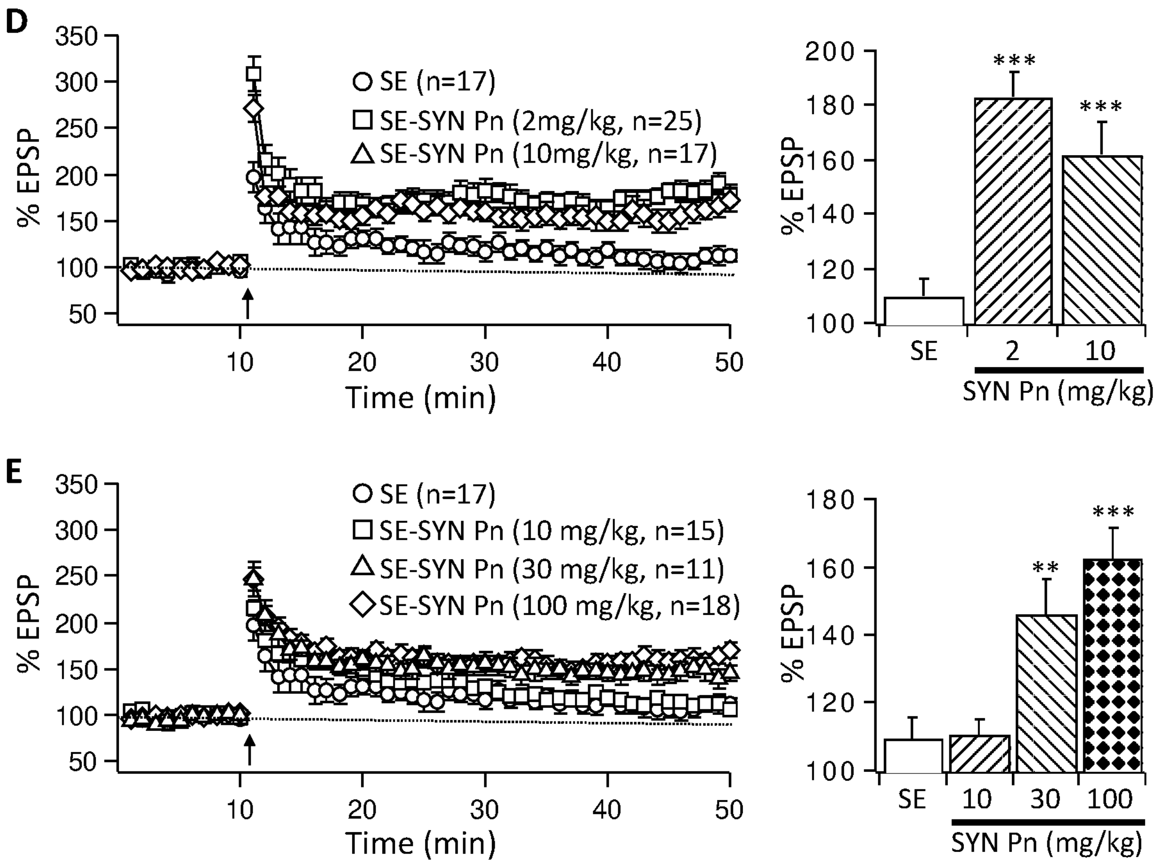

FIG. 11: Hippocampal LTP is rescued by synaptamide phosphonate 1 to 2 weeks following Pilo-SE. FIG. 11A-B: LTP induction in hippocampal slices from rats subjected to Pilo-SE and perfused either with Synaptamide phosphonate-free ACSF (SE) or Synaptamide phosphonate (SE-SYN Pn) at 100 nM (A) and 400 nM (B). FIG. 11C: LTP induction in hippocampal slices from rats subjected to Pilo-SE and injected either with NaCl (SE) or synaptamide phosphonate (SE-SYN Pn, 5 mg/kg; i.p). FIG. 11D: LTP induction (left) in hippocampal slices from rats subjected to Pilo-SE and injected (i.p.) either with NaCl (SE) or synaptamide phosphonate (SE-SYN Pn) at 2 or 10 mg/kg. FIG. 11E: LTP induction in hippocampal slices from rats subjected to Pilo-SE and treated (per os) with synaptamide phosphonate (SE-SYN Pn) at 10, 30 and 100 mg/kg. Synaptamide phosphonate was administered 1 h after cessation of SE, and then each day during 6 days. Control groups received saline solution only. *p<0.05, p<0.01, *p<0.001.

Figure 12:
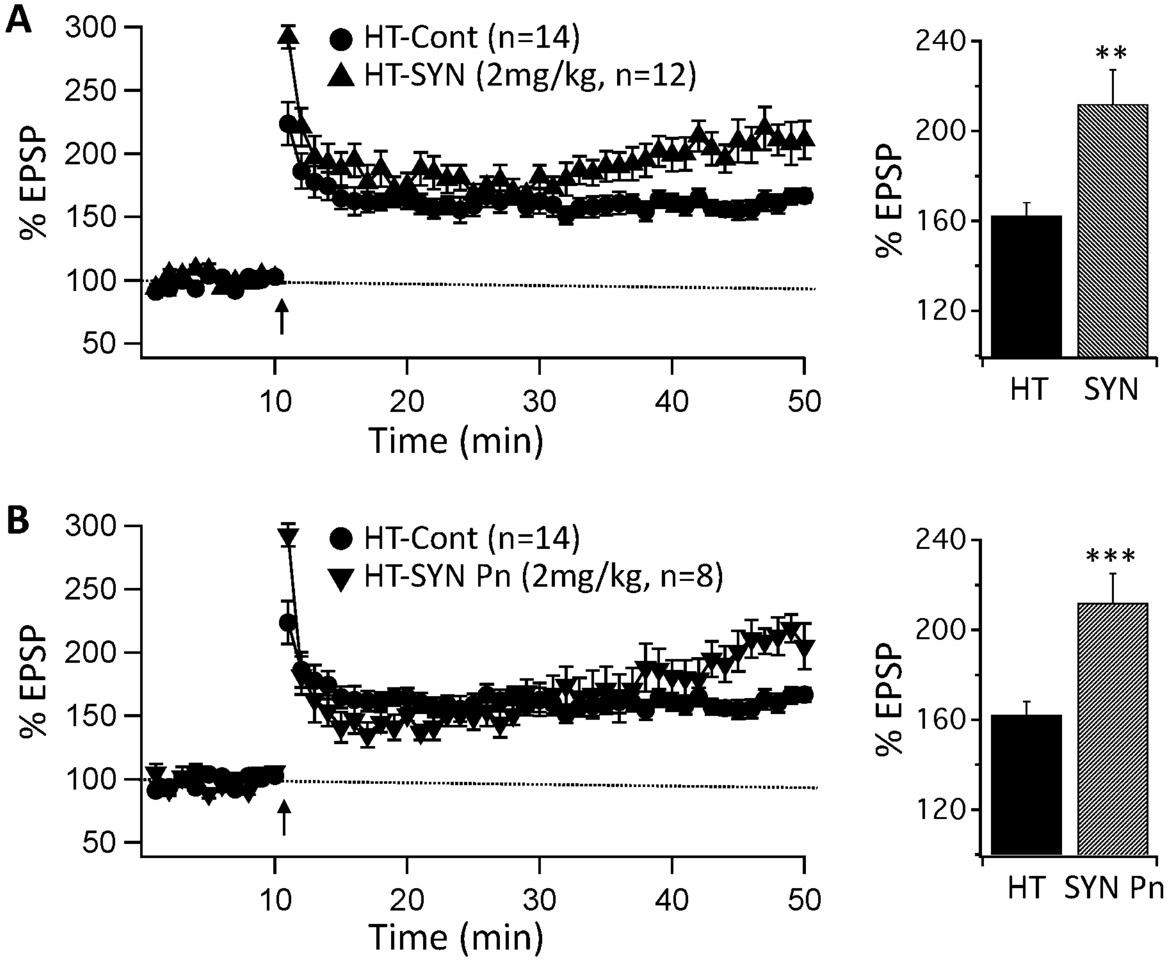

FIG. 12: Synaptamide or synaptamide phosphonate-treatment improves hippocampal LTP in healthy rats. FIG. 12A: LTP induction in hippocampal slices from healthy rats injected either with NaCl (HT) or synaptamide (HT-SYN, 2 mg/kg; i.p). FIG. 12B: LTP induction in hippocampal slices from healthy rats injected either with NaCl (HT) or synaptamide phosphonate (HT-SYN Pn, 2 mg/kg; i.p). Synaptamide or Synaptamide phosphonate were administered each day during 7 days (P21-P27). Control groups received saline solution only. *p<0.05, p<0.01, *p<0.001.

FIG. 13: Effect of SYN-PN administered i.p. at 5, 10 and 50 mg/kg on seizure severity in fully kindled rats. FIG. 13A: total population of rats, n=15. FIGS. 13B-D: rats whose decrease in seizure severity was observed for the first time in response to 5 (13B), 10 (13C) or 50 (13D) mg/kg SYN-PN. Results are expressed as the mean±sem.*, p<0.05; **, p<0.01; * * *, p<0.001; level of significance of the decrease compared to DO, post hoc Fisher LSD test following one-way analysis of variance with repeated measures.

Figure 14:
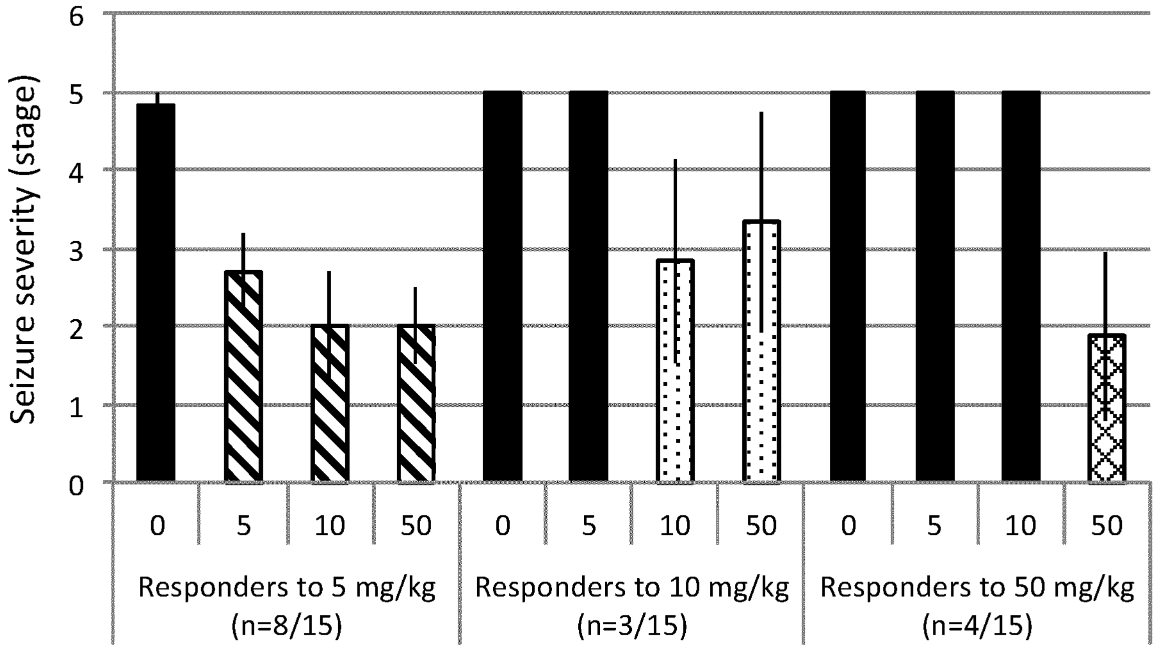

FIG. 14: Effect of SYN-PN on seizure severity observed in rats responding to 5, 10 and 50 mg/kg. Results are expressed as the mean±sem.

Figure 15:
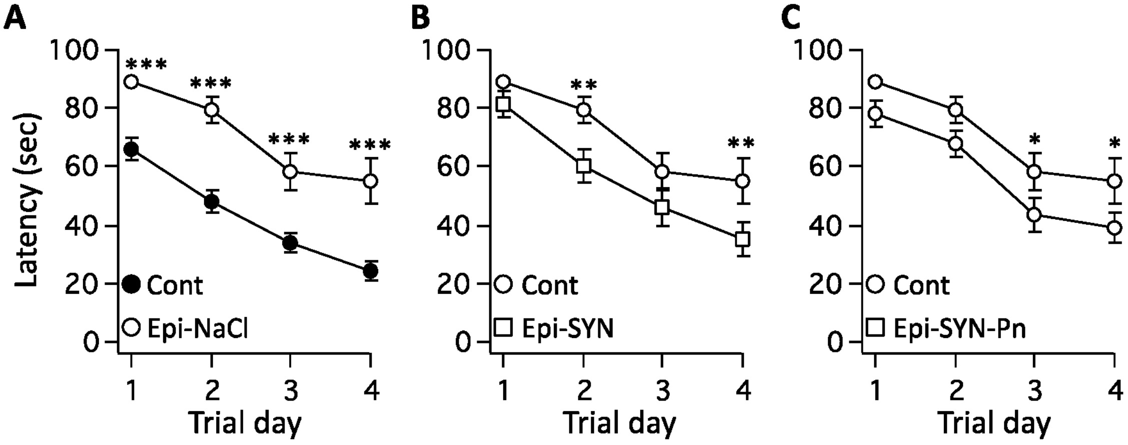

FIG. 15: Treatment with synaptamide or synaptamide phosphonate significantly increased the learning abilities of epileptic rats. FIG. 15A: Graph showing impaired spatial learning in epileptic (Epi, n=14) rats evaluated as increased time needed to locate the platform during the MMW experiment compared to control rats (Cont, n=15).

FIG. 15B-C: Graphs showing improved spatial learning in epileptic rats injected during the first week post-SE with synaptamide (B, Epi-SYN, n=14) or synaptamide phosphonate (C, Epi-SYN-PN, n=14) evaluated as decreased time needed to locate the platform during the MWM experiment. Numbers between brackets indicate the number of rats. Results represent the mean±SEM. *p<0.05, p<0.01, *p<0.001.

Figure 16:
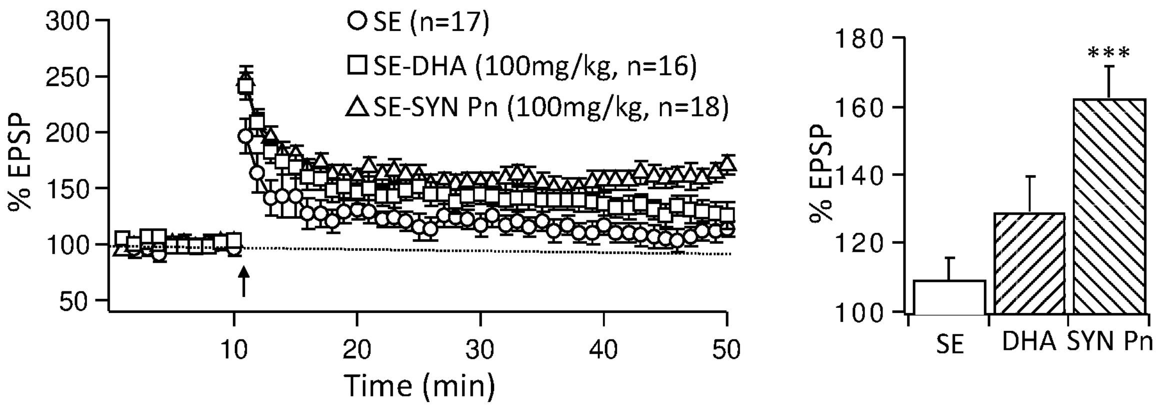

FIG. 16: Oral administration of docosahexaenoic acid at 100 mg/kg dose not prevent hippocampal LTP impairment following SE. LTP induction (left) in hippocampal slices from rats subjected to Pilo-SE and treated (per os) either with synaptamide phosphonate (SE-SYN Pn; 100 mg/kg) or docosahexaenoic acid (SE-DHA; 100 mg/kg). Synaptamide phosphonate or docosahexaenoic acid have been administered 1 h after cessation of SE, then each day during 6 days then once every other day for 2 weeks. *p<0.05, p<0.01, *p<0.001.

Figure 17:
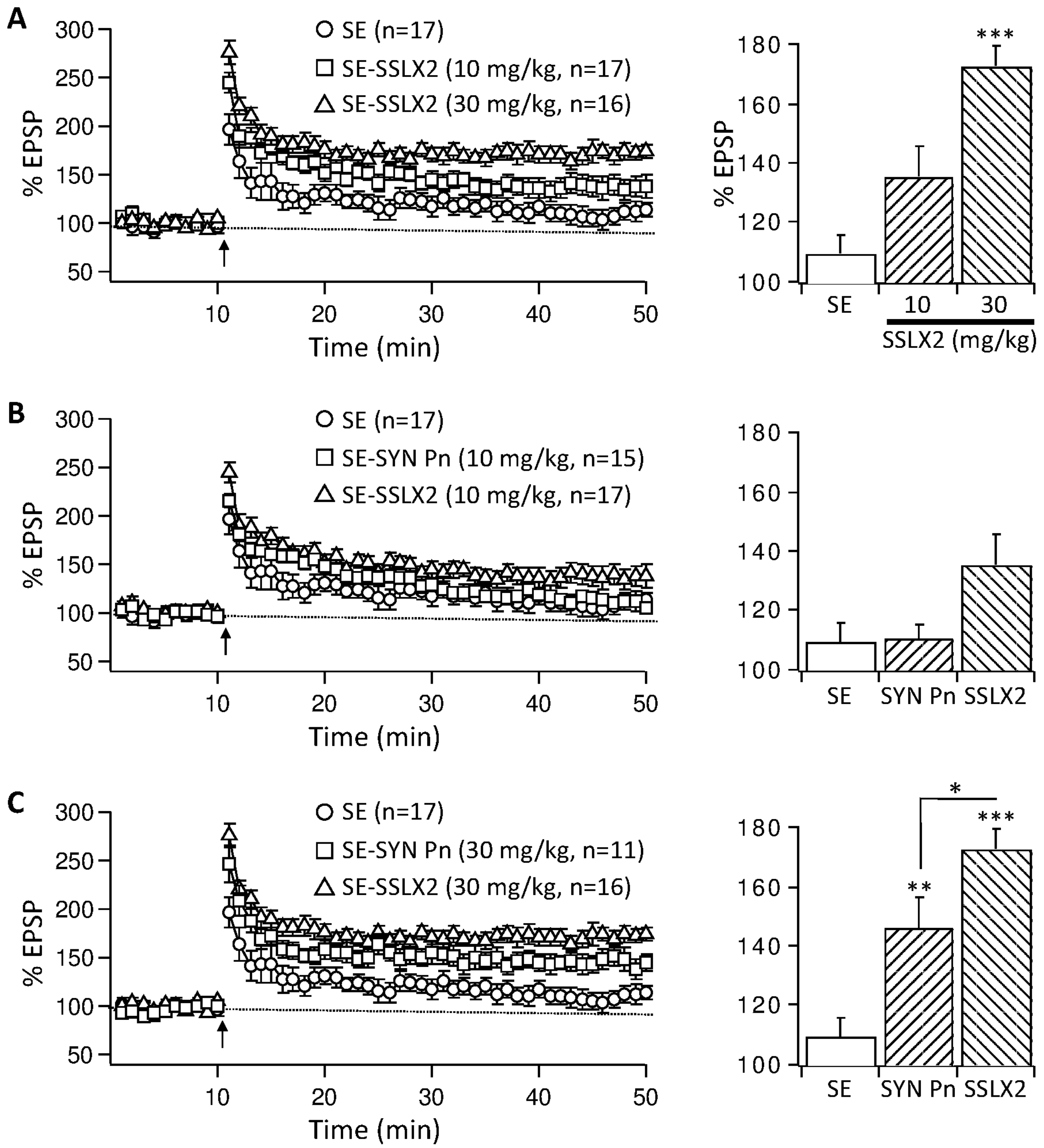

FIG. 17: Oral administration of SSLX2 prevents hippocampal LTP impairment following SE. FIG. 17A-C: LTP induction (left) in hippocampal slices from rats subjected to Pilo-SE (SE) and treated (per os) either with synaptamide phosphonate (SE-SYN Pn) or SSLX2 (SE-SSLX2) at 10 (A-B) and 30 mg/kg (A and C). Synaptamide phosphonate and SSLX2 have been administered 1 h after cessation of SE, then each day during 6 days then once every other day for 2 weeks. *p<0.05, p<0.01, *p<0.001.

Figure 18:
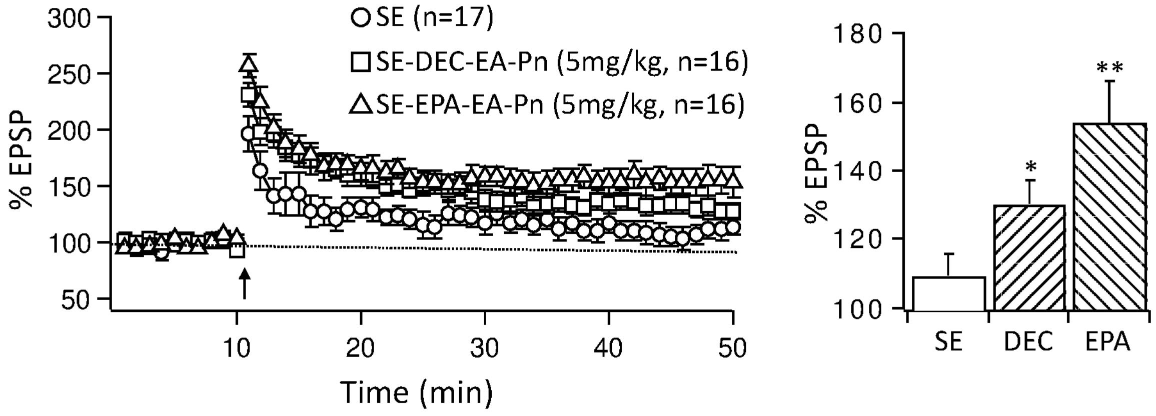

FIG. 18: Intraperitoneal injection of eicosapentaenoic acid ethanolamine phosphonate and decanoic acid ethanolamine phosphonate prevent hippocampal LTP impairment following SE. LTP induction (left) in hippocampal slices from rats subjected to Pilo-SE (SE) and injected (i.p.) either with decanoic acid ethanolamine phosphonate (SE-DEC-EA-Pn; 5 mg/kg) or eicosapentaenoic acid ethanolamine phosphonate (SE-EPA-EA-Pn; 5 mg/kg). Decanoic acid ethanolamine phosphonate or eicosapentaenoic acid ethanolamine phosphonate have been administered 1 h after cessation of SE, then each day during 6 days then once every other day for 2 weeks. *p<0.05, p<0.01, *p<0.001.

Figure 19:
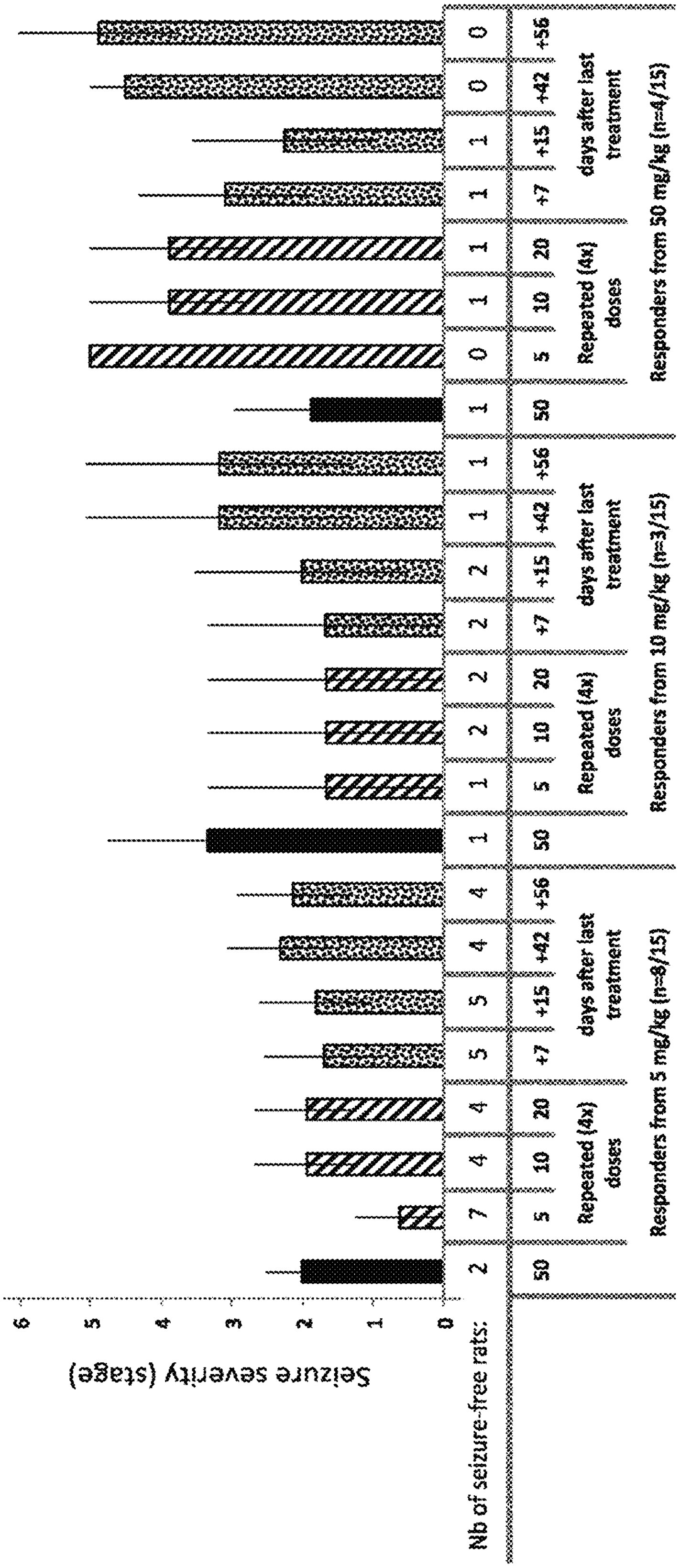

FIG. 19: Sustained anti-seizure effect of Synaptamide Phosphonate after stopping treatment in fully amygdala-kindled rats. All fully-kindled rats (15) showed decreased seizure severity from 5 mg/kg Synaptamide Phosphonate (n=8/15), from 10 mg/kg (n=3/15) or from 50 mg/kg (n=4/15). Plain bars indicate seizure severity observed after acute dose of 50 mg/kg in the 3 subgroups of rats. Hatched bars indicate seizure severity following 4 daily doses of 5, 10 or 20 mg/kg of Synaptamide Phosphonate. Dotted bars show the long-lasting effect observed on seizure severity after stopping Synaptamide Phosphonate treatment. Under the x-axis is indicated the number of seizure-free rats for each condition. Results are expressed as the mean±SEM of the whole subgroup population (n=8, n=3, or n=4).

Figure 20:
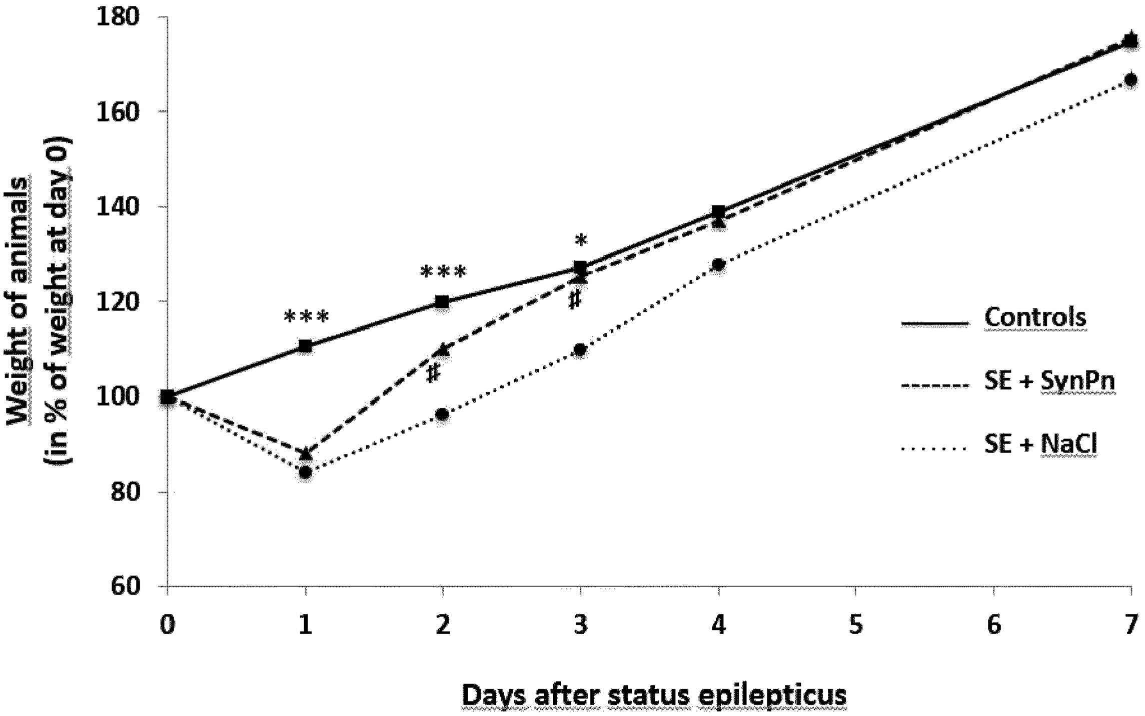

FIG. 20: Synaptamide Phosphonate facilitates the recovery of weight loss in rats after SE. Rats were subjected to pilocarpine-induced status epilepticus at day 0) and were administered (10 mg/Kg, i.p) Synaptamide phosphonate (SynPn) every day for 7 days. The weight of animals was daily measured. Results are expressed as the percentage of weight of animals (10-15 animals/group) at day 0. Statistical differences between Controls/SE+NaCl (*: p<0.05, ***: p<0.001) and between SE+NaCl/SE+SynPn (#: p<0.05).

Figure 21:
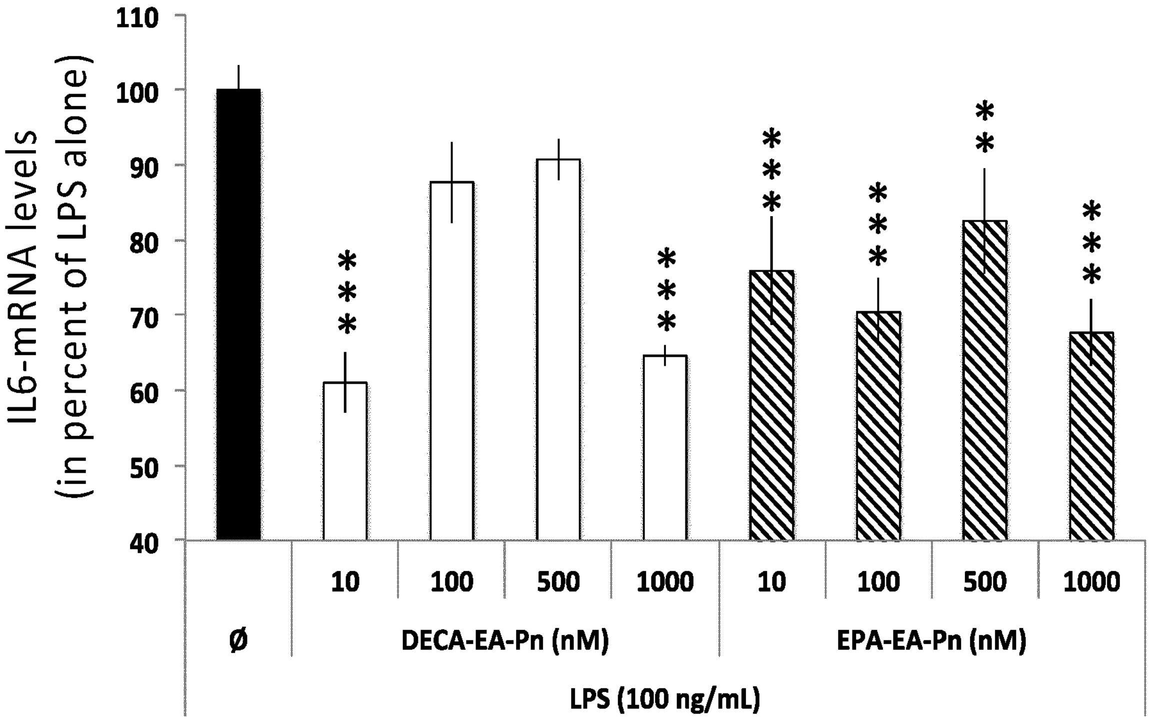

FIG. 21: DECA-EA-Pn and EPA-EA-Pn reduce the induction of pro-inflammatory cytokine IL6-mRNA level in NR8383 cell line in response to LPS treatment. Rat macrophage NR8383 cells were stimulated by LPS (100 ng/mL) and treated with DECA-EA-Pn and EPA-EA-Pn at the indicated concentrations (10, 100, 500 and 1,000 nM) within <2 min after LPS. Cells were collected 5 hours later, which is the time of the apparent peak of TL6-mRNA level induction after LPS. IL-6 mRNA level was quantified by RT-qPCR. Results are expressed as the mean percentage ±SEM (n=3) of the level measured in cells treated with LPS alone (compared to LPS alone: *: p<0.05; : p<0.01; *: p<0.001).

Figure 22:
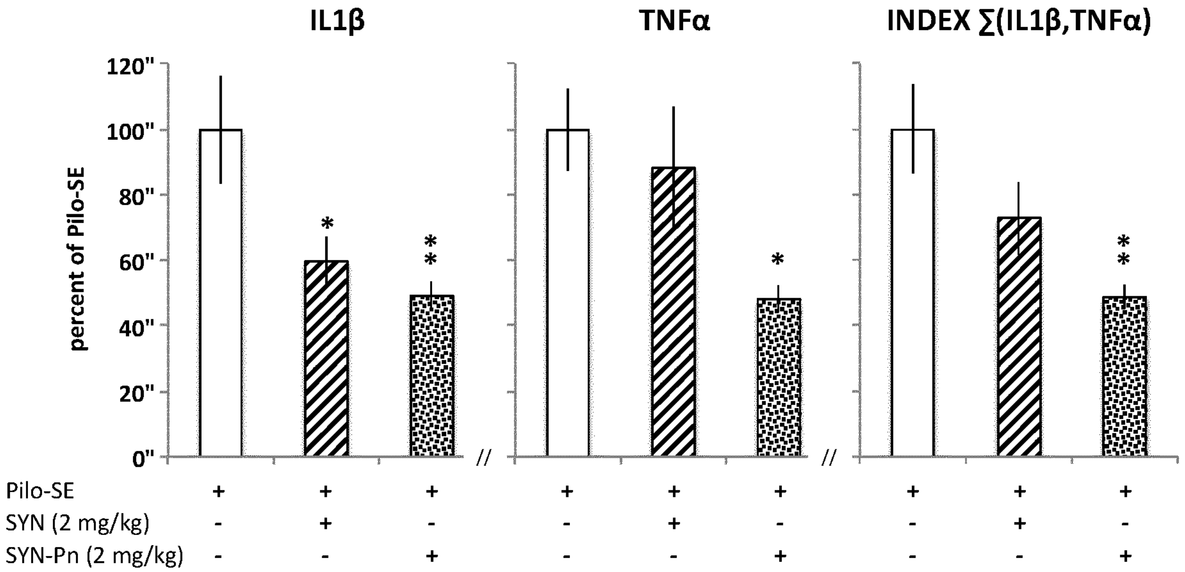

FIG. 22: Effect of SYN-Pn and SYN on the resolution of inflammation in the rat hippocampus following status epilepticus. Juveline (day 42 of age) male Sprague-Dawley rats were subjected to pilocarpine-induced status epilepticus (Pilo-SE), and treated with SYN (2 mg/kg; n=7) or SYN-Pn (2 mg/kg; n=7) 2 h after the onset of SE. Non-treated rats received NaCl (n=5) instead of SYN or SYN-Pn. Brains were collected 9 h post-SE, at the peak of the inflammatory response. The hippocampus was microdissected and mRNA levels quantified by RT-qPCR. Data illustrate variations for IL1β and TNFα mRNAs, and for the index integrating both IL1β and TNFα. Results are expressed as the mean percentage ±SEM of the value measured in rats subjected to Pilo-SE and treated with NaCl (compared to Pilo-SE alone: *: p<0.05; **: p<0.01; ANOVA 1 followed by post hoc Tukey HSD test).

DETAILED DESCRIPTION

As demonstrated by the inventors in the following examples, the present invention provides a new family of vectors having an important structural plasticity, allowing thereby to deliver biologically active compounds, such as long chain fatty acids omega-3 type. These vectors exhibit a particular kinetics of absorption and a particular intestinal localization of absorption. They can deliver fatty acids and their metabolic derivatives, having different structures, and target several different molecular targets. More particularly, the inventors have demonstrated that metabolic derivatives resulting from the hydrolysis of the compounds of formula (I) of the invention could inhibit key molecular inflammatory markers, and could prevent cognitive decline or deficits and/or rescue or restore the cognitive functions in brain injuries, traumatic brain injuries and/or in a neuroinflammatory disease, and/or in a neurodegenerative disease.

According to the invention, the terms below have the following definitions: The term "alkyl chain" refers to one saturated or unsaturated hydrocarbon chain, linear or branched, comprising at least two carbon atoms, and having more particularly from 10 to 24, from 12 to 18, from 12 to 16, carbon atoms, and preferably 14 carbon atoms.

The term "alkyl" refers to a saturated or unsaturated, linear or branched aliphatic group. The term "($C_1$-$C_6$)alkyl" refers to an alkyl group having from 1 to 6 carbon atoms, preferably 1, 2, 3, 4, 5, or 6 carbon atoms. In a preferred embodiment, the term "$C_1$-$C_6$)alkyl" is a methyl, ethyl, propyl, isopropyl, butyl, isobutyl, tert-butyl, pentyl, or an hexyl.

The term "fatty acyl" refers to one alkyl chain as above defined having, particularly from 2 to 30 carbon atoms, which is functionalized by an acyl group. The term "fatty acyl" also includes the corresponding carboxylic acids in which the hydroxyl group of the carboxylic acid has been removed. Examples of fatty acyls or corresponding carboxylic acids are, for instance, acetic acid, propionic acid, butyric acid, valeric acid, caprylic acid, capric acid, lauric acid, myristic acid, palmitic acid, stearic acid, arachidic acid, behenic acid, lignoceric acid, myristoleic acid, palmitoleic acid, oleic acid, vaccenic acid, linoleic acid, alpha-linoleic acid, arachidonic acid, eicosapentaenoic acid, erucic acid, and docosahexaenoic acid. A preferred "fatty acyl" or the corresponding carboxylic acid thereof is capric acid, eicosapentaenoic acid, or docosahexaenoic acid (DHA), more preferably docosahexaenoic acid (DHA).

The term "oxygen derivatives" of one fatty acyl refers to one fatty acyl as above defined substituted by at least one hydroxyl group (—OH). As a non-limiting examples of oxygen derivatives of fatty acyl, resolvins, maresins, neuroprotectins and neuroprostanes may be cited.

The term "halogen" corresponds to one atom of fluorine, chlorine, bromine or iodine.

The term "hydrate" corresponds to a compound in a hydrate form. In a particular embodiment, the term "hydrate" includes semi-hydrates, monohydrates and polyhydrates.

The expression "substituted by at least" means that the radical is substituted by one or several groups of the list.

The "pharmacologically acceptable salts" refer to the salts of the compounds of the invention of formulae (I), (I'), (I''), (II), and (II') having the required biological activity. The "pharmaceutically salts" include inorganic as well as organic acid salts. Representative examples of suitable inorganic acids include hydrochloric, hydrobromic, hydroiodic, phosphoric, and the like. Representative examples of suitable organic acids include formic, acetic, trichloroacetic, trifluoroacetic, propionic, benzoic, cinnamic, citric, fumaric, maleic, methanesulfonic and the like. Further examples of pharmaceutically inorganic or organic acid addition salts include the pharmaceutically salts listed in J. Pharm. Sci. 1977, 66, 2, and in Handbook of Pharmaceutical Salts: Properties, Selection, and Use edited by P. Heinrich Stahl and Camille G. Wermuth 2002. The "pharmaceutically salts" also include inorganic as well as organic base salts. Representative examples of suitable inorganic bases include sodium or potassium salt, an alkaline earth metal salt, such as a calcium or magnesium salt, or an ammonium salt. Representative examples of suitable salts with an organic base include for instance a salt with methylamine, dimethylamine, trimethylamine, piperidine, morpholine or tris-(2-hydroxyethyl)amine.

Compounds of Formula (I)

The present invention thus relates to a compound of formula (I):

(I)

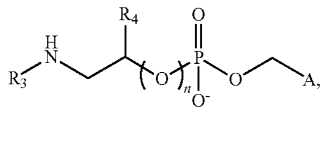

in which:

n is a whole number equal to 0 or 1;

A represents a radical chosen among:

a group of formula (A'):

(A')

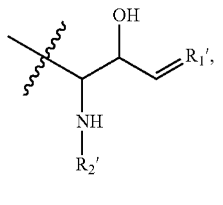

in which:

$R_{1'}$ represents a saturated or unsaturated $(C_1-C_{24})$alkyl chain optionally substituted by at least one group chosen among a hydroxyl and a halogen; and $R_{2'}$ represents a hydrogen, a saturated or unsaturated fatty acyl comprising from 2 to 30 carbon atoms, one of its oxygen derivatives, or a biologically active compound bound to the rest of the molecule by an acyl group; or a group of formula (A''):

(A'')

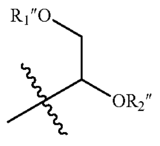

in which:

$R_{1''}$ represents a fatty acyl, preferably saturated, comprising from 2 to 30 carbon atoms; and $R_{2''}$ represents a hydrogen, a saturated or unsaturated fatty acyl comprising from 2 to 30 carbon atoms, one of its oxygen derivatives, or a biologically active compound bound to the rest of the molecule by an acyl group;

$R_3$ represents a hydrogen, a saturated or unsaturated fatty acyl comprising from 2 to 30 carbon atoms, one of its oxygen derivatives, or a biologically active compound bound to the rest of the molecule by an acyl group; and $R_4$ represents a hydrogen or a $(C_1-C_6)$alkyl group;

and the hydrates, or the diastereoisomers, and or the pharmacologically acceptable salts thereof.

In a preferred embodiment, $R_3$ is not a hydrogen.

Preferably, the present invention thus relates to a compound of formula (I):

(I)

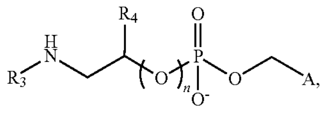

in which:

n is a whole number equal to 0 or 1;

A represents a radical chosen among:

a group of formula (A'):

(A')

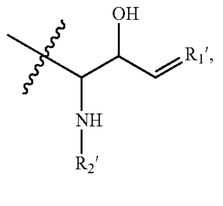

in which:

$R_{1'}$ represents a saturated or unsaturated $(C_1-C_{24})$alkyl chain optionally substituted by at least one group chosen among a hydroxyl and a halogen; and $R_{2'}$ represents a hydrogen, a saturated or unsaturated fatty acyl comprising from 2 to 30 carbon atoms, one of its oxygen derivatives, or a biologically active compound bound to the rest of the molecule by an acyl group; or a group of formula (A"):

(A")

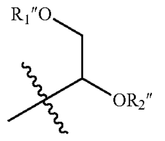

in which:

$R_{1''}$ represents a fatty acyl, preferably saturated, comprising from 2 to 30 carbon atoms; and $R_{2''}$ represents a hydrogen, a saturated or unsaturated fatty acyl comprising from 2 to 30 carbon atoms, one of its oxygen derivatives, or a biologically active compound bound to the rest of the molecule by an acyl group;

$R_3$ represents a saturated or unsaturated fatty acyl comprising from 2 to 30 carbon atoms, one of its oxygen derivatives, or a biologically active compound bound to the rest of the molecule by an acyl group; and $R_4$ represents a hydrogen or a $(C_1-C_6)$alkyl group;

and the hydrates, or the diastereoisomers, and or the pharmacologically acceptable salts thereof.

According to a particular embodiment of the invention, a compound of formula (I), (I'), or (I") is such that $R_{2'}$, $R_{2''}$ and $R_3$ represent independently:

a hydrogen, a saturated or unsaturated fatty acyl comprising from 2 to 30 carbon atoms selected in the group consisting of: acetic acid, propionic acid, butyric acid, valeric acid, caprylic acid, capric acid, lauric acid, myristic acid, palmitic acid, stearic acid, arachidic acid, behenic acid, lignoceric acid, myristoleic acid, palmitoleic acid, oleic acid, vaccenic acid, linoleic acid, alpha-linoleic acid, arachidonic acid, eicosapentaenoic acid, erucic acid, and docosahexaenoic acid, preferably docosahexaenoic acid, or an oxygen derivative of a saturated or unsaturated fatty acyl comprising from 2 to 30 carbon atoms chosen from resolvins, maresins, neuroprotectins and neuroprostanes.

According to another particular embodiment, a compound of formula (I), (I'), or (I") is such that:

$R_{2'}$ and $R_{2''}$ represent independently:

a hydrogen, a saturated or unsaturated fatty acyl comprising from 2 to 30 carbon atoms selected in the group consisting of: acetic acid, propionic acid, butyric acid, valeric acid, caprylic acid, capric acid, lauric acid, myristic acid, palmitic acid, stearic acid, arachidic acid, behenic acid, lignoceric acid, myristoleic acid, palmitoleic acid, oleic acid, vaccenic acid, linoleic acid, alpha-linoleic acid, arachidonic acid, eicosapentaenoic acid, erucic acid, and docosahexaenoic acid, preferably docosahexaenoic acid, or an oxygen derivative of a saturated or unsaturated fatty acyl comprising from 2 to 30 carbon atoms chosen from resolvins, maresins, neuroprotectins and neuroprostanes; and $R_3$ represents:

a saturated or unsaturated fatty acyl comprising from 2 to 30 carbon atoms selected in the group consisting of: acetic acid, propionic acid, butyric acid, valeric acid, caprylic acid, capric acid, lauric acid, myristic acid, palmitic acid, stearic acid, arachidic acid, behenic acid, lignoceric acid, myristoleic acid, palmitoleic acid, oleic acid, vaccenic acid, linoleic acid, alpha-linoleic acid, arachidonic acid, eicosapentaenoic acid, erucic acid, and docosahexaenoic acid, preferably docosahexaenoic acid, or an oxygen derivative of a saturated or unsaturated fatty acyl comprising from 2 to 30 carbon atoms chosen from resolvins, maresins, neuroprotectins and neuroprostanes.

According to a further particular embodiment of the invention, a compound of formula (I), (I'), or (I") is such that $R_{2'}$, $R_{2''}$ and $R_3$ represent a biologically active compound bound to the rest of the molecule by an acyl group.

As used herein, the term "biologically active compound" includes all compounds and all molecules having a biological activity, and more specifically, a therapeutic activity. For instance, a biologically active compound is an anti-inflammatory compound, a neuroleptic, an antipsychotic, and an anti-epileptic compound, etc. According to a particular embodiment, the biologically active compound is a fatty acyl or one of its oxygenated derivatives as described above.

According to this particular embodiment, the biologically active compound is bound to the rest of the molecule by one acyl group (—C═O). Preferably, the biologically active compound is naturally or chemically functionalized by a carbonyl or a carboxyl group in order to form an amide bond (—NH—CO) between the vector and the biologically active compound.

Preferably, the biologically active compound functionalized by a carbonyl or a carboxyl group, forms an amide bond with the amine group of the vector.

According to the invention, the compound of formula (I) is such that $R_4$ represents a hydrogen atom or a $(C_1-C_6)$alkyl group. Preferably, $R_4$ represents a hydrogen atom or a methyl group, and more preferably a hydrogen.

The compounds of formula (I) as above defined, can be classified in two sub-families, the SphingoSynaptoLipoxins (SSLs) of formula (I') and the AminoGlyceroPhosphoSynaptoLipoxins (AGPSL) of formula (I") according to the chemical structure of the radical (A).

SphingoSynaptoLipoxins (SSLs)

SSLs correspond to compounds of formula (I) as above defined, in which A represents a group of formula (A'):

(A')

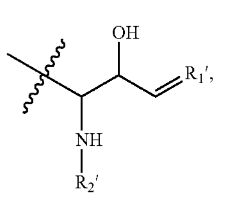

in which:

$R_{1'}$ represents a saturated or unsaturated $(C_1-C_{24})$alkyl chain optionally substituted by at least one group chosen among a hydroxyl and a halogen; and $R_{2'}$ represents a hydrogen, a saturated or unsaturated fatty acyl comprising from 2 to 30 carbon atoms, one of its oxygen derivatives, or a biologically active compound bound to the rest of the molecule by an acyl group.

A particular embodiment of the invention thus relates to a SSL compound of formula (I'):

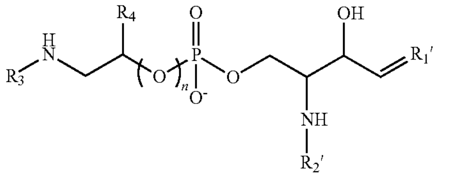

(I')

in which:

n is a whole number equal to 0 or 1;

$R_{1'}$ represents a saturated or unsaturated ($C_1$-$C_{24}$)alkyl chain optionally substituted by at least one group chosen among a hydroxyl and a halogen;

$R_{2'}$ represents a hydrogen, a saturated or unsaturated fatty acyl comprising from 2 to 30 carbon atoms, one of its oxygen derivatives, or a biologically active compound bound to the rest of the molecule by an acyl group;

$R_3$ represents a hydrogen, a saturated or unsaturated fatty acyl comprising from 2 to 30 carbon atoms, one of its oxygen derivatives, or a biologically active compound bound to the rest of the molecule by an acyl group; preferably a saturated or unsaturated fatty acyl comprising from 2 to 30 carbon atoms, one of its oxygen derivatives, or a biologically active compound bound to the rest of the molecule by an acyl group; and $R_4$ represents a hydrogen or a ($C_1$-$C_6$)alkyl group, preferably a methyl group.

According to a preferred embodiment, $R_{1'}$ represents a saturated or unsaturated alkyl chain comprising from 10 to 20, 12 to 18 carbon atoms, with the preference 12 to 16 carbon atoms, and even more preferably 14 carbon atoms, said chain is optionally substituted by at least one group chosen among a hydroxyl and a halogen. According to an even more preferred embodiment, $R_{1'}$ represents a saturated alkyl chain comprising 14 carbon atoms, i.e. a tetradecanyl chain.

According to a further preferred embodiment, $R_{2'}$ and $R_3$ represent independently a hydrogen or docosahexaenoic acid.

According to a further preferred embodiment, $R_4$ represents a hydrogen.

According to a particular embodiment, a compound of formula (I') is such that n is a whole number equal to 0. According to this embodiment in which n is 0, the compounds of formula (I') comprise a phosphonate bond (C-P) that allows attachment of the $R_3$—NH—$CH_2$—CH($R_4$)— group to phosphorus. These compounds of formula (I') with n equal to 0 correspond to the compounds SSL-X as disclosed herein.

A preferred compound of the invention is a compound of formula (I') SSL-$X_1$ in which:

n is a whole number equal to 0;

$R_{1'}$ represents a tetradecanyl group;

$R_{2'}$ represents docosahexaenoic acid;

$R_3$ represents a hydrogen; and $R_4$ represents a hydrogen.

A preferred compound of the invention is a compound of formula (I') SSL-X 2 in which:

n is a whole number equal to 0;

$R_1$ represents a tetradecanyl group;

$R_{2'}$ represents a hydrogen;

$R_3$ represents docosahexaenoic acid; and $R_4$ represents a hydrogen.

A preferred compound of the invention is a compound of formula (I') SSL-X3 in which:

n is a whole number equal to 0;

$R_{1'}$ represents a tetradecanyl group;

$R_{2'}$ represents docosahexaenoic acid;

$R_3$ represents docosahexaenoic acid; and $R_4$ represents one hydrogen.

The compounds SSL-X of the formula (I') can be prepared by a bio-based approach and/or by a total chemical synthesis approach. A general procedure for preparing SSLs compounds of formula (I') is illustrated in FIG. 1.

In the context of a bio-based approach, ceramide aminoethylphosphonate (CAEP) is extracted and purified from marine mollusks, such as mussel Mytilus galloprovincialis which is an abundant and not costly organism compared to other marine mollusks. To achieve this, total lipids are extracted and purified according to the Folch method (Folch J., Lees M. and Stanley G. H. S.; (1957); A simple method for the isolation and purification of total lipids from animal tissues). J. Biol. Chem. 226, 497-509), and then saponified. After the purification of the unsaponifiable fraction, the CAEP is deacylated either by a strong alkaline hydrolysis or by acid hydrolysis. Deacylated CAEP is afterwards purified, and dosed, and put in reaction with a defined quantity of docosahexaenoic acid to obtain the compounds SSL-X1, SSL-X2 and SSL-X3 by N-acylation.

In the context of a total chemical synthesis approach, a first step is an acetylation of the hydroxyl groups of the commercially available sphingomyelin, using for instance acetic anhydride to obtain O-acetylated sphingomyelin. A second step is a hydrolyze of O-acetylated sphingomyelin with a non-specific type C phospholipase (*Clostridium perfringens*) to obtain O-acetylated ceramide, which is then purified. A third step is a phosphonylation of O-acetylated ceramide with monochlorinated 2-phthalimidophosphonic acid to obtain O-acetyl-ceramide-(2-phthalimidoethyl)-phosphonate. A fourth step is a hydrazinolysis of O-acetyl-ceramide-(2-phthalimidoethyl)-phosphonate to obtain O-acetylated sphingosylphophonoethanolamine, which is then purified. Then, the O-acetylated sphingosylphophonoethanolamine reacts with an amount of DHA to provide by N-acylation followed by 0-deacylation the compounds SSL-X1, SSL-X2, and SSLX3.

According to a further particular embodiment, a compound of formula (I') is such that n is a whole number equal to 1. According to this embodiment in which n is 1, the compounds of formula (I') comprise an ester-phosphorus bond (0-P), that allows attachment of the $R_3$-NH—$CH_2$—CH($R_4$)—O— group to phosphorus. These compounds of formula (I') with n equal to 1 correspond to the compounds SSL-Y as disclosed herein.

A preferred compound of the invention is a compound of formula (I') SSL-$Y_1$ in which:

n is a whole number equal to 1;

$R_{1'}$ represents a tetradecanyl group;

$R_{2'}$ represents docosahexaenoic acid;

$R_3$ represents a hydrogen; and $R_4$ represents a hydrogen

A preferred compound of the invention is a compound of formula (I') SSL-$Y_2$ in which:

n is a whole number equal to 1;

$R_{1'}$ represents a tetradecanyl group;

$R_{2'}$ represents a hydrogen;

$R_3$ represents docosahexaenoic acid; and $R_4$ represents one hydrogen.

A preferred compound of the invention is a compound of formula (I') SSL-$Y_3$ in which:

n is a whole number equal to 1;

$R_{1'}$ represents a tetradecanyl group;

$R_{2'}$ represents docosahexaenoic acid;

$R_3$ represents docosahexaenoic acid; and $R_4$ represents a hydrogen.

The compounds SSL-Y1, SSL-Y2 and SSL-Y3 can be synthesized by a total chemical synthesis approach according to a process including the deacylation, purification, dosage and N-acylation steps of the process illustrated in FIG. 1, starting from ceramide phosphorylethanolamine (CPEA) as a commercial starting material.

AminoGlyceroPhosphoSynaptoLipoxins (AGPSLs)

AGPSLs correspond to compounds of formula (I) as defined above, in which A represents a group of formula (A"):

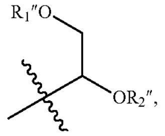

(A")

in which:

$R_{1''}$ represents a fatty acyl, preferably saturated, comprising from 2 to 30 carbon atoms;

$R_{2''}$ represents a hydrogen, a saturated or unsaturated fatty acyl comprising from 2 to 30 carbon atoms, one of its oxygen derivatives, or a biologically active compound bound to the rest of the molecule by an acyl group;

A further particular embodiment of the invention thus relates to an AGPSL compound of formula (I"):

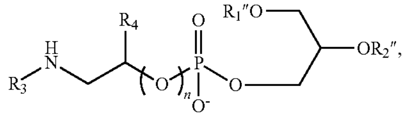

(I")

in which:

n is a whole number equal to 0 or 1;

$R_{1''}$ represents a fatty acyl, preferably saturated, comprising from 2 to 30 carbon atoms;

$R_{2''}$ represents a hydrogen, a saturated or unsaturated fatty acyl comprising from 2 to 30 carbon atoms, one of its oxygen derivatives, or a biologically active compound bound to the rest of the molecule by an acyl group;

$R_3$ represents a hydrogen, a saturated or unsaturated fatty acyl comprising from 2 to 30 carbon atoms, one of its oxygen derivatives, or a biologically active compound bound to the rest of the molecule by an acyl group, preferably, a saturated or unsaturated fatty acyl comprising from 2 to 30 carbon atoms, one of its oxygen derivatives, or a biologically active compound bound to the rest of the molecule by an acyl group; and $R_4$ represents a hydrogen or a ($C_1$-$C_6$)alkyl group, preferably a methyl group.

According to a preferred embodiment, $R_{1''}$ represents a fatty acyl, preferably saturated, comprising 12 to 20 carbon atoms, 12 to 18 carbon atoms, preferably 12 to 16 carbon atoms, and more preferably 16 carbon atoms. According to an even more preferred embodiment, $R_{1''}$ represents palmitic acid.

According to a further preferred embodiment, $R_{2''}$ and $R_3$ represent independently a hydrogen or docosahexaenoic acid.

According to a further preferred embodiment, $R_4$ represents a hydrogen.

According to a particular embodiment, a compound of formula (I") is such that n is a whole number equal to 0. According to this embodiment in which n is 0, the compounds of formula (I') comprise a phosphonate bond (C-P) that allows attachment of the $R_3$—NH—$CH_2$—CH($R_4$)— group to the phosphorus. These compounds of formula (I") with n equal to 0 correspond to the compounds AGPSL-X as disclosed herein.

A preferred compound of the invention is a compound of formula (I") AGPSL-$X_1$ in which:

n is a whole number equal to 0;

$R_{1''}$ represents palmitic acid;

$R_{2''}$ represents docosahexaenoic acid;

$R_3$ represents a hydrogen; and $R_4$ represents a hydrogen.

A preferred compound of the invention is a compound of formula (I") AGPSL-$X_2$ in which:

n is a whole number equal to 0;

$R_{1''}$ represents palmitic acid;

$R_{2''}$ represents a hydrogen;

$R_3$ represents docosahexaenoic acid; and $R_4$ represents a hydrogen.

A preferred compound of the invention is a compound of formula (I") AGPSL-$X_3$ in which:

n is a whole number equal to 0;

$R_{1''}$ represents palmitic acid;

$R_{2''}$ represents docosahexaenoic acid;

$R_3$ represents docosahexaenoic acid; and $R_4$ represents one hydrogen.

The AGPSL-Xs can be prepared by a total chemical synthesis approach. In this context, a first step is a phosphonylation of the commercially available diacylglycerol using 2-monochlorinated phthalimidophosphonic acid to obtain diacylglycerol-(2-phthalimidoethyl)-phosphonate. A second step is an hydrazinolysis of diacylglycerol-(2-phthalimidoethyl) phosphonate to obtain glycerophosphonoethanolamine, which is then purified.

Glycerophosphonoethanolamine then reacts with an amount of DHA to provide, by N-acylation, the compound AGPSL-$X_2$. AGPSL-$X_1$ is obtained by deacylation of glycerophosphonoethanolamine with a phospholipase A2, and by re-O-acylation in presence of DHA. AGPSL-$X_3$ is obtained by deacylation in the sn-2 position of glycerol of AGPSL-X1 and re-O-acylation in presence of DHA.

According to a further particular embodiment, a compound of formula (I") is such that n is a whole number equal to one. According to this embodiment in which n is 1, the compounds of formula (I") comprise an ester-phosphorus bond (O-P), that allows attachment of the $R_3$—NH—$CH_2$—CH($R_4$)—O— group to phosphorus. These compounds of formula (I") with n equal to 1 correspond to the compounds AGPSL-Y as disclosed herein.

A preferred compound of the invention is a compound of formula (I") AGPSL-$Y_1$ in which:

n is a whole number equal to 1;

$R_{1''}$ represents palmitic acid;

$R_{2''}$ represents docosahexaenoic acid;

$R_3$ represents a hydrogen; and $R_4$ represents a hydrogen.

A preferred compound of the invention is a compound of formula (I") AGPSL-$Y_2$ in which:

n is a whole number equal to 1;

$R_{1''}$ represents palmitic acid;

$R_{2''}$ represents a hydrogen;

$R_3$ represents docosahexaenoic acid; and $R_4$ represents a hydrogen.

A preferred compound of the invention is a compound of formula (I") AGPSL-$Y_3$ in which:

n is a whole number equal to 1;

$R_{1''}$ represents palmitic acid;

$R_{2''}$ represents docosahexaenoic acid;

$R_3$ represents docosahexaenoic acid; and $R_4$ represents a hydrogen.

The AGPSL-Ys can be prepared by a total chemical synthesis approach starting from the commercially available phospatidylethanolamine. AGPSL-$Y_1$ is obtained by deacylation of phospatidylethanolamine in sn-2 position of glycerol by a phospholipase A2 and by a re-O— acylation in the presence of DHA. AGPSL-$Y_2$ is obtained by deacylation of phospatidylethanolamine in sn-2 position of glycerol by a phospholipase A2 and by N-acylation in presence of DHA. AGPSL-$Y_3$ is obtained by deacylation of phospatidylethanolamine in sn-2 position of glycerol by a phospholipase A2 and by N-acylation and O-acylation in presence of docosahexaenoic acid.

Compounds of Formula (II)

The present invention further relates to a compound of formula (II):

$$R_5—NH—CH_2—CH(R_7)—O_{(n)}—R_6 \quad \text{(II)},$$

wherein:

n is a whole number equal to 0 or 1;

$R_5$ represents a saturated or unsaturated fatty acyl comprising from 2 to 30 carbon atoms or one of its oxygen derivatives; and $R_6$ is a —$PO_3^{2-}$ group;

$R_7$ represents a hydrogen or a ($C_1$-$C_6$)alkyl group;

with the proviso that when n is equal to 1, then $R_5$ is not an arachidonic acid; and the hydrates, or the diastereoisomers, or the pharmacologically acceptable salts thereof.

According to a particular embodiment of the invention, a compound of formula (II) is such that $R_5$ represents:

a saturated or unsaturated fatty acyl comprising from 2 to 30 carbon atoms selected in the group consisting of: acetic acid, propionic acid, butyric acid, valeric acid, caprylic acid, capric acid, lauric acid, myristic acid, palmitic acid, stearic acid, arachidic acid, behenic acid, lignoceric acid, myristoleic acid, palmitoleic acid, oleic acid, vaccenic acid, linoleic acid, alpha-linoleic acid, arachidonic acid, eicosapentaenoic acid, erucic acid, and docosahexaenoic acid, preferably capric acid, eicosapentaenoic acid, and docosahexaenoic acid, or an oxygen derivative of a saturated or unsaturated fatty acyl comprising from 2 to 30 carbon atoms chosen from resolvins, maresins, neuroprotectins, and neuroprostanes.

In a preferred embodiment of the invention, a compound of formula (II) is such that $R_5$ represents a saturated or unsaturated fatty acyl comprising from 2 to 30 carbon atoms, which is docosahexaenoic acid.

According to the invention, the compound of formula (II) is such that $R_7$ represents a hydrogen or a ($C_1$-$C_6$)alkyl group. Preferably, $R_7$ represents a hydrogen atom or a methyl group, and more preferably a hydrogen.

The compounds of formula (II) as above defined can be classified in two sub-families, the ethanolamine-phosphonate derivatives of fatty acid and the ethanolamine-phosphate derivatives of fatty acid according to the whole number n.

Ethanolamine-Phosphonate Derivatives

In a particular embodiment, the compounds of formula (II) are such that n is equal to 0. Such particular compounds may be called herein "ethanolamine-phosphonate derivatives of fatty acid".

According to this particular embodiment, the compounds of formula (II) can also be represented by the following formula (IIA), $$R_5—NH—CH_2—CH(R_7)—PO_3^{2-} \quad \text{(IIA)},$$

in which $R_5$, and $R_7$ are such as above defined.

In a preferred embodiment, the compounds of formula (IIA) are such that $R_5$ represents a saturated or unsaturated fatty acyl comprising from 2 to 30 carbon atoms chosen among capric acid, eicosapentaenoic acid, and docosahexaenoic acid.

In a further preferred embodiment, the compounds of formula (IIA) are such that $R_7$ represents a hydrogen.

In a more preferred embodiment, a compound of formula (IIA) is such that $R_5$ represents capric acid, eicosapentaenoic acid, or docosahexaenoic acid, and $R_7$ represents a hydrogen.

In an even more preferred embodiment, a compound of formula (IIA) is such that $R_5$ represents docosahexaenoic acid and $R_7$ represents a hydrogen.

Ethanolamine-Phosphate Derivatives

In a particular embodiment, the compounds of formula (II) are such that n is equal to 1. Such particular compounds may be called herein "ethanolamine-phosphate derivatives of fatty acid".

According to this particular embodiment, the compounds of formula (II) can also be represented by the following formula (IIB), $$R_5—NH—CH_2—CH(R_7)—O—PO_3^{2-} \quad \text{(IIB)},$$

in which $R_5$, and $R_7$ are such as above defined with the proviso that $R_5$ is not an arachidonic acid.

In a further particular embodiment, the compounds of formula (IIB) are such that $R_5$ represents a saturated or unsaturated fatty acyl comprising from 2 to 30 carbon atoms chosen among a saturated or unsaturated fatty acyl comprising from 2 to 30 carbon atoms selected in the group consisting of: acetic acid, propionic acid, butyric acid, valeric acid, caprylic acid, capric acid, lauric acid, myristic acid, palmitic acid, stearic acid, arachidic acid, behenic acid, lignoceric acid, myristoleic acid, palmitoleic acid, oleic acid, vaccenic acid, linoleic acid, alpha-linoleic acid, eicosapentaenoic acid, erucic acid, and docosahexaenoic acid, preferably capric acid, eicosapentaenoic acid, and docosahexaenoic acid.

In a preferred embodiment, the compounds of formula (IIB) are such that $R_5$ represents a saturated or unsaturated fatty acyl comprising from 2 to 30 carbon atoms chosen among capric acid, eicosapentaenoic acid, and docosahexaenoic acid.

In a further preferred embodiment, the compounds of formula (IIB) are such that $R_7$ represents a hydrogen.

In a more preferred embodiment, a compound of formula (IIB) is such that $R_5$ represents capric acid, eicosapentaenoic acid, or docosahexaenoic acid, and $R_7$ represents a hydrogen.

In an even more preferred embodiment, a compound of formula (IIB) is such that $R_5$ represents docosahexaenoic acid and $R_7$ represents a hydrogen.

Ethanolamine Derivatives

It is further disclosed herein a compound of formula (II'):

$$R_{5'}—NH—CH_2—CH(R_{7'})—O_{(n)}—R_{6'} \quad (II),$$

wherein:

n is a whole number equal to 1;

$R_{5'}$ represents a saturated or unsaturated fatty acyl comprising from 2 to 30 carbon atoms or one of its oxygen derivatives;

$R_{6'}$ is a hydrogen; and $R_{7'}$ represents a hydrogen or a ($C_1$-$C_6$)alkyl group; and the hydrates, or the diastereoisomers, or the pharmacologically acceptable salts thereof.

Such particular compounds may be called herein "ethanolamine derivatives of fatty acid".

The compounds of formula (II) can also be represented by the following formula (IIC), $$R_5—NH—CH_2—CH(R_7)—OH \quad (IIC),$$

in which $R_5$, and $R_7$ are such as above defined.

In a preferred embodiment, the compounds of formula (IIC) are such that $R_5$ represents a saturated or unsaturated fatty acyl comprising from 2 to 30 carbon atoms chosen among capric acid, eicosapentaenoic acid, and docosahexaenoic acid.

In a further preferred embodiment, the compounds of formula (IIC) are such that $R_7$ represents a hydrogen.

In a more preferred embodiment, a compound of formula (IIC) is such that $R_5$ represents capric acid, eicosapentaenoic acid, or docosahexaenoic acid, and $R_7$ represents a hydrogen.

In an even more preferred embodiment, a compound of formula (IIC) is such that $R_5$ represents docosahexaenoic acid and $R_7$ represents a hydrogen.

Applications

The compounds according to the invention of formula (I), including compounds of formulae (I') and (I"), and of formula (II), including compounds of formulae (IIA) and (IIB), as above disclosed can be used as a drug or a medicine. The compounds according to the invention of formula (I), including compounds of formulae (I') and (I"), and of formula (II), including compounds of formulae (IIA) and (IIB) can be used in the prevention and/or treatment of an inflammatory disease. The compounds according to the invention of formula (I), including compounds of formulae (I') and (I"), of formula (II), including compounds of formulae (IIA) and (IIB), and of formula (II') can be used for preventing cognitive decline/deficits and/or restoring cognitive functions altered in brain injuries and/or in traumatic brain injuries, and/or in a neuroinflammatory disease, and/or in a neurodegenerative disease. In a further particular embodiment of the invention, the compounds of formulae (I), (I'), (I"), (II), (IIA), (IIB), and (II') according to the invention can be used for preventing and/or treating a disease associated with a seizure. In a further particular embodiment of the invention, the compounds of formulae (I), (I'), (I"), (II), (IIA), (IIB), and (II') according to the invention can be used as anti-epileptic drugs. In a further particular embodiment of the invention, the compounds of formulae (I), (I'), (I"), (II), (IIA), (IIB), and (II') according to the invention can be used for protecting cognitive functions during non-pathological aging. In a further particular embodiment of the invention, the compounds of formulae (I), (I'), (I"), (II), (IIA), (IIB), and (II') according to the invention can be used for enhancing cognitive functions in a healthy subject.

As used herein, the terms "treatment", "treat", and "treating" refer to the amelioration, prophylaxis or reversal of a disease or disorder, such as an inflammatory disease or a cognitive disorder in a subject. In one embodiment, the terms "treatment", "treat", and "treating" may also refer to the inhibition or the delay of the progression of the disease or the disorder in a subject. In another embodiment, these terms refer to the delay in the onset of a disease or disorder in a subject. In some embodiments, the compounds of the invention are administered as a preventive measure. In this context, the terms "treatment" and "treat" may correspond to the terms "prevention" and "prevent" that refer to a reduction of the risk of acquiring a specified disease or a disorder in a subject.

As used herein, the term "enhancing/enhancement of cognitive function" refers to an improvement of a capacity, such as attention, concentration, learning or memory in a healthy subject.

As used herein, a "subject" corresponds to any healthy organism or organism likely to suffer from an inflammatory disease and/or a disease associated with a cognitive disorder and/or a behavioral disorder and/or likely to have been subjected to a brain injury or traumatic brain injuries. In a preferred embodiment, the subject is a mammal, preferably a human.

Without being associated with a particular mechanism of action, the compounds of formula (I) allow to carry/deliver molecules having anti-inflammatory and/or anti-epileptic properties and/or having protective and restorative properties of cognition. For instance, the compounds of formula (I) may carry fatty acids (or their metabolic derivatives), delivering thereby in vivo either the fatty acid, the ethanolamine derivative thereof, or the ethanolamine-phosphonate derivative thereof, or the ethanolamine-phosphate derivative thereof. As an example, when the compounds of formula (I) carry docosahexaenoic acid, they can deliver in vivo either DHA and/or synaptamide and/or synaptamide Phosphonate and/or Phosphorylated synaptamide. As used herein the term "synaptamide" corresponds to "DHA-ethanolamine".

The anti-inflammatory properties of the compounds of the invention make them very interesting in the treatment of neurodegenerative diseases with a significant neuroinflammatory component. Due to their properties, these compounds are also effective in the treatment of various inflammatory diseases other than neurodegenerative diseases.

An object of the invention therefore relates to a compound of formula (I), (I'), (I"), or (II) as defined herein for use as a medicine. A further object of the invention is a pharmaceutical composition comprising at least one compound of the invention of formula (I), (I'), (I") or (II), as defined herein, and an acceptable pharmaceutical excipient. It is also disclosed a pharmaceutical composition comprising at least one compound of the invention of formula (II'), as defined herein, and an acceptable pharmaceutical excipient.

According to a particular embodiment, the pharmaceutical composition of the invention comprising a compound of formula (I), (I'), (I"), or (II) is used for preventing and/or treating an inflammatory disease. Inflammatory diseases include, for instance, inflammatory diseases of the central nervous system (neuroinflammatory diseases), inflammatory diseases of the retina, inflammatory joint diseases, and inflammatory diseases of the digestive system Neuroinflammatory diseases are characterized by inflammation in the central nervous system (CNS), including the brain, the spinal cord, and the retina. The signs and symptoms of neuroinflammatory diseases may vary depending on the affected part of the CNS.

Inflammation of the CNS or the retina can cause focal disorders such as stroke, paresthesia, vision loss, speech disorders, memory loss, decreased mental alertness, and changes in concentration and behavior.

CNS inflammation can also cause psychiatric symptoms such as hallucinations, distortions of thinking, confusion, and mood swings. Depending on the extent and location of inflammation in the CNS, epileptic seizures and headaches can be frequent. Epilepsy, Alzheimer's disease, Parkinson's disease, multiple sclerosis, dementia, and Huntington's disease are non-exhaustive examples of neuroinflammatory diseases.

Inflammatory diseases of the digestive system are characterized by a hyperactivity of the digestive immune system in the wall of part of the digestive tract. Crohn's disease, ulcerative colitis and Bowel syndrome are non-exhaustive examples of inflammatory diseases of the digestive system.

Inflammatory joint diseases are characterized by inflammation in the joints. Arthritis and rheumatoid are non-exhaustive examples of inflammatory joint diseases.

In a further particular embodiment, the pharmaceutical composition of the invention comprising a compound of formula (I), (I'), (I"), (II), or (II') is used to prevent and/or treat a disease associated with a cognitive disorder. A cognitive disorder means a mental disorder that particularly affects memory, attention and flexibility. The causes of cognitive disorders vary between the different types of disorders, but most of them are caused by brain damage.

Alzheimer's disease, Parkinson's disease, Huntington's disease, epilepsy, delirium, dementia and amnesia are non-exhaustive examples of diseases associated with a cognitive disorder.

In a further particular embodiment, the pharmaceutical composition of the invention comprising a compound of formula (I), (I'), (I"), (II), or (II') is used to prevent and/or treat a disease associated with a seizure. A "seizure" may be caused by a paroxysmal alteration of neurologic function caused by the excessive, hypersynchronous discharge of neurons in the brain. An example of a disease associated with a seizure is epilepsy, which is the condition of recurrent, unprovoked seizures, as well as any reversible disorder that triggers (provokes) a brain irritation leading to a seizure, such as an infection, a stroke, a head injury, or a reaction to a drug. In children, a fever can trigger a nonepileptic seizure (also called "febrile seizure").

Certain mental disorders can cause symptoms that resemble seizures, called psychogenic nonepileptic seizures or pseudoseizures.

The invention therefore relates to a pharmaceutical composition comprising a compound of formula (I), (I'), (I"), or (II) as defined herein, for use for preventing and/or treating a disease chosen among an inflammatory disease, particularly an inflammation of the central nervous system or a neuroinflammatory disease, an inflammatory disease of the digestive tract, an inflammatory disease of the retina, an inflammatory joint disease. The invention therefore further relates to a pharmaceutical composition comprising a compound of formula (I), (I'), (I"), (II) or (II') as defined herein for use for preventing and/or treating a disease associated with a cognitive disorder.

The invention also concerns a method for treating a disease chosen among an inflammatory disease, particularly an inflammation of the central nervous system or a neuroinflammatory disease, an inflammatory disease of the digestive tract, an inflammatory joint disease, an inflammatory disease of the retina, or a disease associated with a cognitive disorder, comprising administering of an efficient amount of a compound of formula (I) or (II) or a pharmaceutical composition comprising such compound in a subject in need thereof.

The invention also concerns the use of a compound of formula (I) or (II) for manufacturing a pharmaceutical composition for treating a disease chosen among an inflammatory disease, particularly an inflammation of the central nervous system or a neuroinflammatory disease, an inflammatory disease of the digestive tract, an inflammatory joint disease, an inflammatory disease of the retina, or a disease associated with a cognitive disorder.

In a particular embodiment of the invention, the disease/disorder to be prevented and/or treated by the compounds of formula (I), (I'), (I"), (II), or (II') is chosen from epilepsy, traumatic brain injury, Alzheimer's disease, Parkinson's disease, multiple sclerosis, Crohn's disease, Bowel syndrome, dementia, and Huntington's disease, and preferably epilepsy.

An object of the invention is a pharmaceutical composition as defined herein comprising a compound of formulae (I), (I'), (I"), (II), and (II') for use for preventing and/or treating a disease selected in the group consisting of epilepsy, traumatic brain injury, Alzheimer's disease, Parkinson's disease, Multiple Sclerosis, Crohn's Disease, Bowel's Syndrome, Dementia, and Huntington's Disease. A further object of the invention is a method for treating such diseases comprising administering a pharmaceutical composition as defined herein comprising a compound of formula (I), (I'), (I"), (II), and (II') in a subject in need thereof. A further object of the invention is a use of a compound of formula (I), (I'), (I"), (II), and (II') for manufacturing a pharmaceutical composition for preventing and/or treating such diseases.

As used herein, "epilepsy" includes epilepsy with focal aware seizures, or with focal impaired awareness seizures, or with bilateral tonic clonic seizures, or with absence seizures, or with atypical absence seizures, or with tonic-clonic seizures, or with atonic seizures, or with clonic seizures, or with tonic seizures, or with myoclonic seizures, or with gelastic and dacrystic seizures, or with febrile seizures, or with refractory seizures, and the different epilepsy syndromes, including autosomal dominant nocturnal frontal lobe epilepsy, childhood absence epilepsy, childhood epilepsy with centrotemporal spikes aka benign rolandic epilepsy, Doose syndrome, Dravet syndrome, early myoclonic encephalopathy, epilepsy of infancy with migrating focal seizures, Epilepsy with Eyelid Myoclonia (Jeavons Syndrome), epilepsy with generalized tonic-clonic seizures alone, epilepsy with myoclonic absences, epileptic encephalopathy with continuous spike and wave during sleep, frontal lobe epilepsy, infantile spasms (West's syndrome) and Tuberous Sclerosis Complex, juvenile absence epilepsy, juvenile myoclonic epilepsy, Lafora progressive myoclonus epilepsy, Landau-Kleffner Syndrome, Lennox-Gastaut Syndrome, Ohtahara Syndrome, Panayiotopoulos Syndrome, Progressive myoclonic epilepsies, reflex epilepsies, temporal lobe epilepsy.

A particular object of the invention is a pharmaceutical composition as defined herein comprising a compound of formulae (I), (I'), (I"), (II), and (II') for use for decreasing/reducing the severity and/or the frequency of epileptic seizures. A further particular object of the invention is a method for decreasing/reducing the severity and/or the frequency of epileptic seizures, comprising administering a pharmaceutical composition as defined herein comprising a compound of formula (I), (I'), (I"), (II), and (II') in a subject in need thereof. A further particular object of the invention is a use of a compound of formula (I), (I'), (I"), (II), and (II') for manufacturing a pharmaceutical composition for decreasing/reducing the severity and/or the frequency of epileptic seizures.

In a further particular embodiment, the invention relates to a pharmaceutical composition as defined herein, for use for preventing cognitive decline/deficits and/or restoring cognitive functions altered in brain injuries and/or in traumatic brain injuries, and/or in a neuroinflammatory disease, and/or in a neurodegenerative disease.

A particular embodiment of the invention relates to a method for restoring cognitive functions altered in brain injuries and/or in traumatic brain injuries, and/or in a neuroinflammatory disease, and/or in a neurodegenerative disease, comprising administering of an efficient amount of a compound of formula (I), (I'), (I"), (II), or (II') or a pharmaceutical composition comprising such compound in a subject in need thereof.

A further particular embodiment of the invention relates to a use of a compound of formula (I), (I'), (I"), (II), or (II') for manufacturing a pharmaceutical composition for preventing cognitive decline or restoring cognitive functions altered in brain injuries and/or in traumatic brain injuries, and/or in a neuroinflammatory disease, and/or in a neurodegenerative disease As used herein, "cognitive functions" refers to all mental functions related to knowledge including executive function, learning and memory, attention and processing speed, language, among others.

As used herein brain injuries include injuries of brain resulting from an inside or outside source. A particular brain injury from an outside source is a "traumatic brain injury" that refers to a head injury or craniocerebral trauma including head and brain injuries.

Clinically, there are three main categories of traumatic brain injury: mild (no loss of consciousness or skull fracture), moderate (with initial loss of consciousness exceeding a few minutes or with skull fractures) and severe (with a coma right away without or with associated skull fractures). Amongst the many sequelae of traumatic brain injury, cognitive impairment may be paramount in relation to its contribution to long-term dysfunction.

Neurodegenerative diseases are disabling chronic diseases with slow and discrete evolution, in which the inflammatory component contributes to etiology. Neurodegenerative diseases also result in loss or alteration of cognitive functions. Spinocerebellar ataxia, multisystem atrophy, Alexander's disease, Alpers disease, Alzheimer's disease, Lewy body dementia, Creutzfeld's disease, Huntington's disease, Parkinson's disease, Pick's disease, progressive supranuclear palsy, and amyotrophic lateral sclerosis are non-exhaustive examples of neurodegenerative diseases.

According to a further particular embodiment, the invention relates to a use of a pharmaceutical composition as defined herein, for preventing and/or preserving cognitive functions during aging and/or enhancing cognitive functions in a healthy subject.

A particular embodiment of the invention relates to a method for preserving cognitive functions during aging and/or enhancing cognitive function in a healthy subject, comprising administrating of an efficient amount of a compound of formula (I), (I'), (I"), (II), or (II') or a pharmaceutical composition comprising such compound in said healthy subject. As used herein, the "preserving of cognitive functions" means also the reduction of the risks of the alteration of cognitive functions.

According to the invention, the pharmaceutical composition as defined herein includes a pharmaceutically acceptable support or carrier. A "Pharmaceutically acceptable support" comprises a support containing at least one acceptable pharmaceutical excipient. A "Pharmaceutically acceptable excipient" comprises any excipient allowing to formulate the pharmaceutical composition of the invention in the desired galenic form without inducing adverse effects on the treated subject. A skilled person is able to choose the nature and the proportion of the pharmaceutically acceptable excipients according to the formulation adapted to the intended route of administration.

As used herein an "effective amount" or an "effective dose" determines the amount or the quantity of the compound of the invention or the pharmaceutical composition comprising a compound of the invention, allowing to obtain a therapeutic effect sufficient to treat and/or prevent an inflammatory disease or a disease characterized by a cognitive deficit. It is understood that the administered amount may be adapted by those skilled in the art according to the patient, the pathology, the mode of administration, and the severity of the disease, etc.

For example, an effective amount of a compound of the invention of formula (I), (I'), (I"), (II), or (II') is between 0.01 mg/kg and 100 mg/kg (BW), between 0.01 mg/kg and 50 mg/kg (BW), between 0.01 mg/kg and 10 mg/kg (BW). Particularly, an effective amount of a compound of the invention of formula (I), (I'), (I"), (II), or (II') is 5 mg/kg (BW), 10 mg/kg (BW), or 50 mg/kg (BW). This effective amount may be taken by the patient only once or occasionally such as once a week, twice a week or three times a week, or more frequently such as one or more times a day, for instance two or three times a day. Preferably this amount is daily administered, i.e. once a day, in a subject.

According to a preferred embodiment, the compound of formula (I), (I'), (I"), (II), or (II') of the invention is administered in a subject at an amount or a dose between 0.01 mg/kg and 100 mg/kg (BW), preferably between 0.01 mg/kg and 10 mg/kg (BW), and more preferably about 5 mg/kg (BW) 10 mg/kg (BW), or 50 mg/kg (BW). In a particular aspect, the compounds and the pharmaceutical compositions of the invention can be administered several days a week, such as 4, 5, 6, or 7 days. Preferably, they are administered once a day.

The administration route of the pharmaceutical composition of the invention can be oral or parenteral (including subcutaneous, intramuscular, intraperitoneal, intracerebroventricular, intravenous and/or intradermal). Preferably, the administration route is parenteral, oral or topical. In a context of a parenteral injection, the intravenous injection is preferred.

According to a preferred embodiment, the pharmaceutical composition comprising a compound of formula (I) is to be administered per os.

According to a further preferred embodiment, the pharmaceutical composition comprising a compound of formula (II) or (II') is to be administered by oral route or by parental route. A preferred parental route is an intraperitoneal route.

As described in examples, SSLs corresponding to compounds of formula (I'), present a slow and prolonged intestinal hydrolysis/absorption, while the glycerophospholipids AGPSLs, corresponding to compound of formula (I"), are relatively fast hydrolyzed/absorbed in the intestinal tract. (Digestion of Phospholipids after Secretion of Bile into the Duodenum Changes the Phase Behavior of Bile Components. Woldeamanuel A. Birru. et al., Mol.

Pharmaceutics, 2014, 11, 2825-2834). These pharmacokinetic differences introduce numerous potential advantages and allow a treatment of a patient either in the acute or chronic manner, offering thereby many possibilities of therapeutic interventions according to the clinical case. For a chronic treatment, administration per os of a pharmaceutical composition comprising a compound of formula (I') is preferred. For an acute treatment, an administration per os of a pharmaceutical composition comprising a compound of formula (I") is preferred.

In therapeutic emergencies, such as traumatic brain injury and status epilepticus, the intravenous, intracerebroventricular, or subcutaneous administration of metabolic derivatives of fatty acids as described herein, in particular metabolic derivatives of docosahexaenoic acid like synaptamide, synaptamide phosphate and synaptamide phosphonate can be considered.

Thus, a further object concerns a pharmaceutical composition comprising at least one metabolic derivative of docosahexaenoic acid, in particular synaptamide, synaptamide phosphate and/or synaptamide phosphonate, for use for protecting and/or restoring the cognitive functions altered by a traumatic brain injury and/or a status epilepticus, in which said pharmaceutical composition is administered intravenously.

A further object concerns a method for protecting and/or restoring cognitive functions altered by a traumatic brain injury and/or a status epilepticus in a subject, comprising the intravenous administration of an effective amount or dose of at least one metabolic derivative of docosahexaenoic acid, in particular synaptamide, synaptamide phosphate and/or synaptamide phosphonate or a pharmaceutical composition comprising them in this subject.

Another object concerns the use of at least one metabolic derivative of docosahexaenoic acid, in particular synaptamide, synaptamide phosphate and/or synaptamide phosphonate, for manufacturing a pharmaceutical composition for protecting and/or restoring cognitive functions altered by a traumatic brain injury and/or status epilepticus, in which said pharmaceutical composition is administered intravenously.

According to a preferred embodiment, said at least one of the metabolic derivatives of docosahexaenoic acid, in particular synaptamide, synaptamide phosphate and/or synaptamide phosphonate is intravenously administered in a subject at a dose ranging from 0.01 to 10 mg/kg (BW), preferably from 0.5 to 5 mg/kg (BW), and more preferably at the dose of about 2 mg/kg (BW).

According to another embodiment, the compounds of the invention of formula (I) including compounds of formulae (I') and (I"), and the compounds of the invention of formula (II) including compounds of formula (IIA) and (IIB) as herein defined, can be used as food supplements.

Further aspects and advantages of the present invention are disclosed in the following examples, which should be considered as illustrative and not limiting the scope of the present application.

EXAMPLES

Example a: Synthesis

I.1. Synthesis of SSL-X Compounds (n=0)

1. Bio-Based Approach

The synthesis of SSL-X has been performed using the relative abundance of ceramide aminoethylphosphonate (CAEP) in some marine organisms, especially bivalve mollusks such as the mussel Mytilus galloprovincialis. To do so, total lipids were extracted and purified according to the Folch method (Folch J., Lees M. and Stanley G.H.S.; (1957); A simple method for the isolation and purification of total lipids from animal tissues). J. Biol. Chem. 226, 497-509). The lipids were then saponified. After purification of the unsaponified lipid fraction, CAEP was deacylated either using strong alkaline hydrolysis or acidic hydrolysis. The deacylated CAEP was then purified and quantified. The SSL-X1, SSL-$X_2$, and SSL-X3 were then synthesized by N-acylation. FIG. 1 is illustrating the synthesis procedure.

The detailed procedure for synthesis of SSLs is described thereafter.

1.1. Extraction and Purification of Total Lipids.

Total lipids are extracted and purified according to Folch method. To do so, the tissues are homogenized using a Polytron in a chloroform-methanol (2:1, v/v) mixture (25 mL/g of tissue). Lipid extraction is allowed to proceed for 12 hours at 4° C. The samples are filtrated using ash-free filters and lipids are purified using phase partition as follows: A first wash of the crude lipid extract is performed using a 0.25% aqueous KCl solution (m/v) that is added to the lipid extract at a rate of a quarter of lipid extract volume. After phase separation, the aqueous-methanolic phase is discarded. Initial proportion of chloroform-methanol is restored by adding methanol to the organic lower phase and a second wash is performed using deionized water in the same conditions used for the first wash. The upper phase, containing the non-lipid contaminants is discarded and the chloroformic lower phase is brought to dryness using a rotary evaporator. Traces of water are removed by sequentially adding absolute ethanol and drying again the sample, and placing it in a desiccator overnight. The mass of total lipids is determined and lipids are kept until further use at −30° C. in a volume of benzene-methanol (1:1, v/v).

1.2. Saponification of Total Lipids.

Lipids are subjected to mild alkaline methanolysis in order to remove ester lipids such as triglycerides, sterolesters and glycerophospholipids. At the opposite, sphingolipids (including our molecules of interest) are resistant to saponification.

The latter is performed at room temperature for 1 hour in a mixture of chloroform-methanol (1:1, v/v) containing 0.3 M NaOH. The concentrations of chloroform are then adjusted in order to obtain a chloroform-methanol ratio of (2:1, v/v). The non-saponifiable lipidic fraction is then purified by phase partition after adding deionized water (one quarter of chloroform-methanol volume). The aqueous upper phase is discarded and the chloroformic lower phase is evaporated to dryness. The non-saponifiable lipidic fraction is then dissolved in a volume of benzene-methanol (1:1, v/v).

1.3. Deacylation of Ceramide Aminoethylphosphonate and Purification of its lyso Form.

Deacylation was performed using either a strong alkaline treatment or an acidic treatment. The strong alkaline treatment was performed under agitation using 1.5 M KOH in methanol at 100° C. for 24 hours. The reaction was stopped by addition of conc. HCl.

Acid hydrolysis was performed at 75° C. for 6 hours using conc. HCl-methanol (1:5, v/v). After cooling, two liquid extractions were realized using hexane. The strong alkaline hydrolysis allowed the formation of sphingosylaminoethylphosphonate (SAEP) but some traces of non-hydrolyzed CAEP is still detectable. In order to separate precursor and reaction product we developed a chromatographic procedure in order to purify the sphingosylaminoethylphosphonate. To do so we used the fact that SAEP displays an additional amino group when compared to the CAEP precursor. The separation of compounds was performed using weak-cation exchange LC-WCX columns. The columns were first conditioned by applying successively hexane, 0.5 M acetic acid in methanol, methanol and then hexane. The samples were applied on the columns in chloroform-methanol (9:2.5, v/v). The non-hydrolyzed CAEP was eluted in a first fraction with chloroform-methanol (9:4, v/v) containing 0.1M acetic acid. SAEP was then eluted in a second fraction using methanol containing 1M acetic acid as solvent system.

1.4. Synthesis of SSL-X1, SSL-X2, and SSL-X3 by N-Acylation

The SAEP produced and purified in the previous step (paragraph 1.3) was first quantified. This dosage is based on phosphorus determination, each molecule of SAEP containing one carbon of phosphorus, thus allowing a direct determination of SAEP quantity.

The dosage was realized spectrophotometrically after mineralization of the molecule in a mixture of conc. sulfuric acid-conc. perchloric acid (2:1, v/v) containing 1 g/L of vanadium tetroxide as catalyst. The detection of inorganic phosphorus was performed after reaction with amino naphthalene sulfonic acid.

Once quantified, SAEP was N-acylated with docosahexaenoic acid (DHA). N-acylation was performed in a mixture of dichloromethane-dimethylformamide (3:1, v/v) containing diethylphosphorylcyanide as coupling agent in presence of triethylamine. The reaction was allowed to proceed at room temperature for 90 min under agitation in the dark and in a nitrogen saturated atmosphere. This procedure allowed the reaction without the preliminary derivatization of the carboxylic function of DHA. The conditions of reaction were established so that it proceeds in a stoichiometric ratio voluntarily "degraded" with a ratio of DHA/SAEP lower than 2:1 (mole/mole) at the beginning of reaction. In this approach, the carboxylic group was introduced in a limited quantity, allowing a random N-acylation of one or two of the free amino groups of SAEP. This synthesis procedure allowed the concomitant synthesis of SSL-X1, SSL-X2, and SSL-X3 at the same time in one pot. The different reaction products (SSL-X1, SSL-X2, and SSL-X3) were then separated and purified using aminopropyl (LC-NH2) column preconditioned with hexane. Several fractions were eluted and collected from the column using the following solvent systems. F1 (not showed in FIG. 2): hexane-ethyl acetate (85:15, v/v); F2: diisopropyl ether-acetic acid (9:5, v/v); F3: acetone-methanol (9:1.35, v/v); F4: chloroform-methanol (2:1, v/v); F5: chloroforme-methanol-3.6 M aqueous ammonium acetate (30:60:8, v/v/v). SAEP: control SAEP. The different fractions were evaporated under nitrogen, resuspended in a volume of chloroform-methanol (2:1, v/v) and applied on TLC. The lipids were separated using chloroform-methanol-ethanol-ethyl acetate-0.25% aqueous KCl (10:4:10:3.6, v/v/v/v/v) and revealed by carbonization. The results are illustrated in FIG. 2.

2. Chemical Synthesis

Compounds SSL-X1, $SSL\text{-}X_2$, and $SSL\text{-}X_3$ are synthesized according to the following synthesis procedure:

- An O-acetylation step makes it possible to neutralize the hydroxyl group (s) carried by the sphingoid base of a commercial sphingomyelin which serves here as a basic material for the synthesis of the molecules of interest. This O-acetylation is carried out at room temperature for 18 h in the presence of pyridine and anhydrous acetic acid. N-acetylation phenomena is prevented by the fact that the two amino groups of sphingomyelin are substituted.
- The second step is to hydrolyze O-acetylated sphingomyelin with a non-specific type C phospholipase (*Clostridium perfringens*) to release the O-acetylated ceramide. The O-acetylated ceramide is purified by simple phase partition in chloroform-methanol (1:1, v/v) and addition of deionized water.
- The purified O-acetylated ceramide is then phosphonylated after reaction with monochlorinated 2-phthalimidophosphonic acid. This phosphonylation reaction makes it possible to synthesize O-acetyl-ceramide-(2-phthalimidoethyl)-phosphonate.
- The next step is a hydrazinolysis of O-acetyl-ceramide-(2-phthalimidoethyl)-phosphonate.

This allows N-deacylation of O-acetyl-ceramide-(2-phthalimidoethyl)-phosphonate and concomitant release of the phthaloyl group. The O-acetylated sphingosylphophonoethanolamine thus produced is then purified by filtration, successive crystallizations in 90% ethanol and then diisopropyl ether, followed by treatment with the strong cation exchanger Amberlite IR120 H. The purified O-acetylated sphingosylphophonoethanolamine is then N-acylated (by docosahexaenoic acid for example) following the procedure described in section 1.4 above. The SSL-X1, $SSL\text{-}X_2$, and $SSL\text{-}X_3$ synthesized during this procedure are O-deacetylated by controlled alkaline methanolysis (0.6 N NaOH in methanol for 1 hour at room temperature) and then purified by phase partition and separation on aminopropyl column.

I.2. Synthesis of SSL-Y Compounds (n=1)

SSL-Y1, SSL-Y2 and SSL-Y3 were synthesized following the same process starting from commercial ceramide phosphorylethanolamine (CPEA) as a precursor. The synthesis was carried out following the same procedure as for the synthesis of CEAP. For this, the CPEA was deacylated as described in section 1.3 and the sphingosylphosphorylethanolamine was N-acylated (by docosahexaenoic acid) as described in section 1.4.

I.3. Synthesis of AGPSL-X Compounds (n=0)

The procedure followed for the chemical synthesis of AGPSLs-X is based on the same synthesis procedure as that used for the chemical synthesis of SSL-Xs with the following differences:

Synthesis of AGPSL-X2

- The precursor used for the synthesis of AGPSLs is 1,2-diacylglycerol of commercial origin with esterified in position sn-1 of glycerol preferably a medium chain saturated fatty acid (palmitic acid, stearic acid). The first synthesis step consisted of phosphonylating 1,2-diacylglycerol with monochlorinated phthalimidophosphonic acid. This phosphonylation reaction made it possible to obtain 1,2-diacylglycerol (2-phthalimidoethyl) phosphonate.

The second step consisted in the hydrazinolysis of the latter compound to obtain 1,2-diacylglycerol phosphonoethanolamine. The 1,2-diacylglycerol phosphonoethanolamine was dissolved in chloroform-methanol (2:1, v/v) and was purified by phase partition after addition of deionized water (one quarter of the total volume of chloroform-methanol).

The third step consisted of deacylating the 1,2-diacylglycerol phosphonoethanolamine at the R2 position of the glycerol using a non-specific phospholipase A2 (PLA2 from Apis millifera). The reaction was carried out with stirring in diethyl ether-borate buffer (100 mM, pH 8.9) (1:1, v/v) containing 200 U phospholipase A2 for 40 min at 37° C. At the end of the reaction, the diethyl ether was evaporated under nitrogen and the sample was extracted with chloroform-methanol (2:1, v/v). The lipids were purified by phase partition by adding deionized water at a quarter volume of chloroform-methanol (2:1, v/v).

The 2-lyso, 1-acyl glycerophosphonoethanolamine obtained during the PLA2 hydrolysis was then purified in a fourth step by aminopropyl column solid phase extraction. This allowed to eliminate fatty acids released under the action of PLA2.

The purified 2-lyso, 1-acyl glycerophosphonoethanolamine was assayed (lipid phosphorus assay) and N-acylation with docosahexaenoic acid for example was carried out as described in section 1.4 for the synthesis of SSL-X2 thus allowing the synthesis of AGPSL-X2.

Synthesis of AGPSL-X3

The synthesis of AGPSL-X3 was performed by O-acylating AGPSL-X2 in the presence of 1,3-dicyclohexylcarbodiimide and 4-(dimethylamino) pyridine. AGPSL-X3 was then purified on an aminopropyl column.

Synthesis of AGPSL-X1

The synthesis of AGPSL-X1 was carried out starting from the 1-acyl, 2-lyso glycerophosphonoethanolamine purified during step 4 of the synthesis of AGPSL-X2. 1-Acyl, 2-lyso glycerophosphonoethanolamine was O-acylated in position R2 by the fatty acid of interest (DHA) in the presence of 1,3-dicyclohexylcarbodiimide and 4-(dimethylamino) pyridine) and then purified on aminopropyl column.

I4. Synthesis of AGPSL-Y Compounds (n=1)

Synthesis of AGPSL-Y2

The synthesis of AGPSL-Y was carried out starting from Phosphatidylethanolamine (cephalin) of commercial origin. This phosphatidylethanolamine was deacylated using a non-specific phospholipase A2 (Apis millifera PLA2). The reaction was carried out under stirring condition in diethyl ether-borate buffer (100 mM, pH 8.9) (1:1, v/v) containing 200 U phospholipase A2 for 40 min at 37° C. At the end of the reaction, the diethyl ether was evaporated under nitrogen and the sample was extracted with chloroform-methanol (2:1, v/v). The 1-acyl-2-lyso glycerophosphorylethanolamine obtained was purified by phase partition by adding deionized water at a rate of one quarter of the volume of chloroform-methanol (2:1, v/v) followed by solid phase extraction on LC-NH2 column. The N-acylation with the fatty acid of interest (DHA for example) was carried out in a mixture of dichloromethane-dimethylformamide (3:1, v/v) containing diethylphosphorylcyanide as coupling agent in the presence of triethylamine. This reaction was carried out at ambient temperature for 90 minutes with stirring in the absence of light and under a saturated nitrogen atmosphere. AGPSL-Y2 was then purified by filtration, phase partition and aminopropyl column extraction.

Synthesis of AGPSL-Y3

The purified AGPSL-Y2 was then O-acylated at the R2" position with the fatty acid of interest (DHA) and then purified by solid phase extraction on an aminopropyl column.

Synthesis of AGPSL-Y1

The AGPSL-Y1 was synthesized from commercial phosphatidylethanolamine by 0-deacylation using non-specific phospholipase A2 (Apis millifera PLA2) as described above for the synthesis of AGPSL-Y2. The 1-acyl-2-lyso glycerophosphorylethanolamine obtained was then purified by solid phase extraction and then O-acylated at the R2" position with the fatty acid of interest in order to obtain the AGPSL-Y1 which was finally purified on aminopropyl column.

I.5. Synthesis of the Metabolic Products Arising from the Intestinal Hydrolysis of SSLs and AGPSLs The synthesis approach that has been used is divided into two main steps: hydroxysuccinimidation and transamination. The example below describes the synthesis of synaptamide phosphonate starting from DHA as fatty acid. The protocol for the synthesis of any other N-acyl ethanolamine phosphonate is similar using the corresponding fatty acid.

The hydroxysuccinimidation step of DHA was carried out as follows: DHA (100 mg, 0.3 mmol) and N-hydroxysuccinimide (57.4 mg, 0.5 mmol) were diluted in 10 ml of ethyl acetate. α-Tocopherol (40 μM) was added to prevent potential oxidation of fatty acids. A solution of dicyclohexylcarbodiimide (DCC, 103 mg) in ethyl acetate (1 mL) was added to the previous solution. The reaction mixture, saturated with nitrogen, was left for at least 12 hours at room temperature and protected from light, with stirring. To stop the reaction, the DCC was filtered using an ashless filter and the filtrate crystallized under nitrogen. In order to obtain a better purification, the material obtained was dissolved in ethanol, filtered and recrystallized. The amount of N-hydroxysuccinimide DHA ester was determined by weighing: 126.3 mg. The transamination reaction was carried out as follows: the N-hydroxysuccinimide DHA ester (50 mg) was diluted in tetrahydrofuran (10 mL). This solution was added to an aqueous mixture (10 mL) of phosphorylated ethanolamine (23.5 mg) or ethanolamine phosphonate (21 mg) and sodium bicarbonate (14 mg). The reaction was carried out for at least 16 hours, at room temperature, with stirring, protected from light and under a saturated atmosphere with nitrogen.

Each solution was transferred to a flask and then evaporated with a Rotavapor. After evaporation, the flasks were taken up with 50 mL of $H_2O$ and filtered through filter paper in a new flask. Each flask was again evaporated. The evaporated flasks were taken up with 40 mL of ethanol, filtered again and then taken up with 20 mL of ethanol and filtered one last time. These latter flasks were evaporated with a Rotavapor and weighed in order to quantify the phosphorylated and phosphonated synaptamide masses obtained. The flasks were taken up twice with 5 mL of ethanol and stored at −80° C. The molecules of interest (synaptamide, synaptamide phosphonate and phosphorylated synaptamide) produced were purified by reverse phase liquid chromatography. The molecules thus synthesized were monitored by mass spectrometry (HR-ESI/MS). Synaptamide phosphonate: MS m/z [M+H+]=436.26; Phosphorylated synaptamide: MS m/z [M+H+]=452.25

Example B: Biological Results

Example B-1: Metabolic Fate of SSLs in Digestive Tract

Materials and Methods

Animals

The rats used in our experiments were Sprague Dawley males (Charles River, Saint Germain sur L'Arbresle, France) weighing ~200 g at the time of their reception at the approved animal facility, maintained at a temperature of 21° C. under diurnal conditions (light period from 06:00 to 18:00). The rats were kept in groups of 5 individuals per cage with ad libidum access to water and food. All animal testing procedures were in accordance with the European directive 86/609, transposed into French law by decree 87/848. Every effort has been made to minimize the suffering and stress of the animal and to reduce the number of animals used. The animals were used two weeks after their arrival in the animal facility.

Administration of SSLs to Animals

Studies on the fate of SSLs in the digestive tract have been performed on SSL-X1. For this, an aliquot of SSL-X1 corresponding to 227 g of lipid phosphorus was deposited in a glass tube. The solvents were evaporated under nitrogen. A second evaporation was carried out after addition of absolute ethanol. Then 625 l of a glucose-containing aqueous solution (0.1 g glucose/mL) was added to the tube. The molecule was dissolved in the aqueous solution by gentle sonication (two 30 s sonications at 40 W power). The molecule was administered per os to the animal using a micropipette. Oral administration by gavage was not necessary, the animal spontaneously drinking the solution presented to it.

In order to quantify the potential hydrolysis of SSLs in rats in vivo, we performed two groups of distinct experiments:

We initially administered per os the molecule to 5 rats as described in the previous paragraph. The animals were previously placed in individual cages. The objective of this experiment was to quantify the molecule possibly present in the rat faeces. For this purpose, the faeces were taken at different times following the administration of the molecule. The faeces collected at each time were pooled and the lipids were extracted and analyzed as described in the following paragraphs.

In a second step, we administered to other rats the molecule. Then the rats were sacrificed 5 h, 8h, 24 h and 36 h following the administration of the molecule. Sacrifice was achieved by a lethal (250 mg/Kg) intraperitoneal injection of pentobarbital (Dolethal solution, Vétoquinol, Lure). Immediately after death, the peritoneal cavity was incised so as to clear the viscera.

The entire intestinal tract was removed from the pyloric region till the anus. The set was placed in a plastic gutter to extend the tissue. The latter was then cut every 10 centimeters or so. The cecum was also collected separately. The large intestine was removed and divided into two equal parts. Then the contents of each intestinal section were removed by rinsing the intestinal lumen with an aqueous solution of NaCl 9% o. The contents of each intestinal section were collected in a 125 ml flask for extraction and lipid analysis as described in the following paragraph.

Lipid Analysis of Faeces

Extraction and purification of lipids from faeces were performed as follows:

- Grinding in 50 mL of chloroform—methanol (2:1, v/v) according to the method of Folch. Extraction of the lipids for 24 hours at 4° C.
- Filtration of the homogenate on ashless filter.
- 1st wash of the crude lipid extract by adding an aqueous solution of KCl 0.25% (w/v) corresponding to ¼ of the total volume of chloroform-methanol (2:1, v/v).
- 2nd wash of the lipid extract by adding methanol corresponding to ⅓ of the initial total volume and deionized water corresponding to ¼ of the total volume of chloroform-methanol (2:1, v/v).
- Evaporation of the organic phase using a rotary evaporator.
- Recovery of total lipids in 2 times 4 mL of benzene-methanol (2:1, v/v). The lipid extracts were then processed in order to isolate/purify the SSL-X1 molecule for quantification. Briefly, the lipid extracts were saponified and washed. The saponified extract was then directly deposited on a 10×10 cm thin layer chromatographic plate. Given the amount of lipids extracted by samples, lipid deposition was performed on a strip of 7 cm in length. An aliquot of ceramide aminoethylphosphonate (corresponding to 10 micrograms of purified phosphorus lipid) was also deposited in parallel on the same plate as standard.

The deposited lipids were then separated in diisopropyl ether. This solvent was used to separate all the neutral lipids from the ceramide aminoethylphosphonate. In this system, this molecule remains at the deposit, whereas all of the neutral lipids (sterols, lipid products derived from saponification, bile salts) migrate to the solvent front. After separation, the chromatography plate was dried under hot air flow, and the plate was developed in chloroform-acetone-methanol-acetic acid-deionized water (50:20:10:15:5, v/v/v/v/v). After drying, the plate was revealed using the Dittmer and Lester reagent and the position of the SSL-X1 molecule was identified by the standard deposited in parallel with the sample on the plate before migration. The spot of SSL-X1 was then scraped with a razor blade into a test tube where mineralization of the sample was performed. Then the lipid phosphorus assay was performed.

Results

Quantification of Hydrolysis—Analysis of Faeces Collected in Cages

In order to determine if the SSL-X1 molecule was efficiently hydrolyzed/absorbed in the rat digestive tract, we first administered a specific amount (~227 g Phosphorus/animal) of the molecule to the animals. Then all the faeces present in the cages were collected at different times after the administration at 16, 21, 26, 40 and 50 hours). The quantities of SSL-X1 measured in the faeces at these different times are shown in FIG. 3.

Analysis of Faeces Collected In Situ in the Intestinal Tract

In order to determine the distribution of SSL-X1 in the intestinal tract of the rats, the animals were sacrificed at different times following the administration of the molecule. Then the entire intestinal tract was removed to recover the contents of the intestinal lumen. The recovery of the content was carried out on sections (~10 cm in length) that we realized on the entire tract. SSL-X1 was assayed on each of the lipid extracts made on the contents of each of the intestinal sections taken.

FIG. 4 shows the results obtained in rats which had been sacrificed 5 hours (FIG. 4A), 8 hours (FIG. 4B) and 36 hours (FIG. 4C) after ingestion of the molecule. Ceramide aminoethylphosphonate was detected/measured in all the intestinal sections analyzed. These observations made it possible to show the following points regarding the physiology of lipolysis of SSL-X1. This molecule is able to reach the colon. These observations demonstrate that if the molecule is hydrolyzed/absorbed in the digestive tract, a fraction of the ceramide aminoethylphosphonate is able to reach the large intestine. This suggests that the intestinal hydrolysis of SSL-X1 follows a similar path as that known for sphingomyelin, another sphingophospholipid, although the two molecules differ in their structures by the absence of phosphoric ester linkage in SSL-X1.

Example B-2: Effects of SSLs and their Metabolic Derivatives on the Neuroinflammation B.2.1. Effects of Metabolite Derivatives of SSLs and AGPSLs on the Inflammatory Status Of an Activated Microglia Cell Line of Human Origin.

B.2.1.1. Cell Culture

Immortalized human microglia (IHM; Innoprot, Derio, Spain) were seeded at 13,000 cells/cm$^2$ in T75 flasks coated with type I human collagen (10 µL/mL, Coating Matrix Kit, Innoprot). The medium was formulated for optimal growth of human brain-derived microglia in vitro, and contained 1% pen/strep, 1% of microglia growth supplement and 5% fetal bovine serum (Microglial Cell Medium Kit, Innoprot).

B.2.1.2. Time-Course of Inflammatory Response

IHM were seeded (10,000 cells/cm$^2$) in type 1 collagen-coated 6-well plates. When cell culture was about 80% confluent, IL-1β (R&D Systems) was added to the culture medium at 0.5 ng/mL, 1.5 ng/mL or 3.0 ng/mL. At t=0, each well received 1 mL of medium only (controls) or 1 mL of medium containing the desired concentration of IL-1β. Cells were harvested at t=0h, t=3h, t=8 h and t=24h. Each tested condition was repeated as triplicates.

B.2.1.3. Effects of Synaptamide Phosphonate on the Expression of Inflammatory Markers The effect of synaptamide phosphonate has been tested as illustrated in FIG. 5. IHM cells have been cultured as mentioned in paragraph B.2.1.2, and, when the culture was about 80% confluent, they were incubated with synaptamide phosphonate at either one of the 3 following concentrations (10, 150 or 300 nM), 3 hours before adding IL-1β (3 ng/mL, t=0 h). Cells were then harvested for RNA extraction after 5 hour-incubation with IL-10.

B.2.1.4. Measurements of mRNAs of Interest Using RT-qPCR

1. Extraction of Total RNAs and Purification

Total RNAs were extracted using Tri-Reagent (MRC, Inc.), as recommended by the manufacturer. Contaminant genomic DNA was subsequently removed from the samples by treatment with Turbo DNA-free™ kit (Ambion).

2. Calibrated Reverse Transcription (RT) of mRNAs

The messenger RNAs (mRNAs) contained in 480 ng of purified RNA extracts were reverse-transcribed using PrimeScript® RT Reagent (Ozyme). To normalize the RT step, a synthetic external and non-homologous poly(A) standard RNA (SmRNA; Morales and Bezin, patent WO2004.092414) was added to the RT reaction mix (150,000 copies in each experimental sample).

3. qPCR Amplification of cDNAs of Interest

PCR amplification of targeted cDNAs was performed using the Rotor-Gene Q system (Qiagen) and the QuantiTect SYBR Green PCR Kit (Qiagen). Sequences of the different primer pairs used for PCR amplification are listed in Table 1.

The ScDNA copy number measured after qPCR was used to estimate the RT step yield for each sample, taking into account that the same number of SmRNA copies was initially present in all samples before RT step. This yield made it possible to standardize the values obtained for all the genes of interest measured from the same sample. This normalization method makes it possible to take into account the variations in the efficiency of the RT between the samples, without having recourse to an internal standard, so-called "house-keeping gene", the expression of which is considered apriori invariant.

TABLE 1

| | cDNA | Seq Ref | Forward primer (5'→3') | SEQ ID | Reverse primer (5'→3') | SEQ ID |
|---|---|---|---|---|---|---|
| *Rattus norvegicus* | IL1β | NM_031512 | TGTGATGAAAGACGGCACAC | SEQ ID No: 1 | CTT CTT CTT TGG GTA TTG TTT GG | SEQ ID No: 2 |
| | IL6 | NM_012589 | CCC TTC AGG AAC AGC TAT GAA | SEQ ID No: 3 | ACA ACA TCA GTC CCA AGA AGG | SEQ ID No: 4 |
| | TNFα | NM_012675 | TGA ACT TCG GGG TGA TCG | SEQ ID No: 5 | GGG CTT GTC ACT CG AGT TTT | SEQ ID No: 6 |
| | MCP1 | NM_031530 | CGG CTG GAG AAC TAC AAG AGA | SEQ ID No: 7 | TCT CTT GAG CTT GGT GAC AAA TA | SEQ ID No: 8 |
| | COX2 | NM_017232 | ACC AAC GCT GCC ACA ACT | SEQ ID No: 9 | GGT TGG AAC AGC AAG GAT TT | SEQ ID No: 10 |
| *Homo sapiens* | IL1β | NM_000576 | TAC CTG TCC TGC GTG TTG AA | SEQ ID No: 11 | TCT TTG GGT AAT TTT TGG GAT CT | SEQ ID No: 12 |
| | IL6 | NM_000600 | CAG GAG CCC AGC TAT GAA CT | SEQ ID No: 13 | AGC AGG CAA CAC CAG GAG | SEQ ID No: 14 |

TABLE 1-continued

| cDNA Seq Ref | Forward primer (5'→3') | SEQ ID | Reverse primer (5'→3') | SEQ ID |
|---|---|---|---|---|
| TNFα NM_000594 | CAG CCT CTT CTC CTT CCT GAT | SEQ ID No: 15 | GCC AGA GGG CTG ATT AGA GA | SEQ ID No: 16 |
| MCP1 NM_002982 | AGT CTC TGC CGC CCT TCT | SEQ ID No: 17 | GTG ACT GGG GCA TTG ATT G | SEQ ID No: 18 |

B.2.2. Induction of Neuroinflammation In Vivo by Lipopolysaccharide (LPS) Injection First, we determined the time after which the maximum neuroinflammatory response could be observed in pups after injection of LPS. For this purpose, 21-day-old Sprague Dawley rats (Charles River, St Germain sur l'Arbresle, France) received an intraperitoneal injection of LPS (Sigma, ref 055: B55) at a dose of 1 mg/Kg. This dose corresponds to that usually used in the literature. Then the rats were sacrificed using a lethal dose of pentobarbital (250 mg/Kg, i.p.) 2, 4, 6, 10 and 24 hours after the injection of LPS and perfused transcardially with an ice-cold solution of 0.9% NaCl. The hippocampus (HI) and the neocortex were collected, frozen in liquid nitrogen and stored at −80° C. until analysis. Analysis of the expression level of the key markers of neuroinflammation was performed by RT-qPCR as described above using the primer pairs shown in Table 1. These preliminary experiments had indeed allowed us to determine that the peak of brain inflammation was observed 6 hours after injection of LPS. Subsequently, rats that received any treatment to resolve LPS-induced neuroinflammation were sacrificed 6 hours post-LPS.

All studies aimed at studying gene expression of various inflammatory markers analyze each gene separately, making the conclusions difficult to build regarding the evolution of the inflammatory state, especially when the expression increases for some genes and remains stable or decreases for others. Since qPCR quantifies the number of cDNA copies in a given sample, we circumvented the difficulty mentioned above by developing for each sample a Neuroinflammation Index (NI), which is the sum of all targeted cDNAs quantified by qPCR. However, in the calculation of this NI, we have been careful not to mask the large expression variations of genes expressed at low levels in basal conditions by subtle expression variations of genes expressed at high-to very high levels in basal conditions. To this end, for each rat, the number of copies of each cDNA has been expressed in percent of the averaged number of copies measured in the whole considered population of individuals. Once each cDNA was expressed in percent, an index was calculated by adding the percent of each transcript involved in the composition of the index.

To test the effect of the hydrolysis products of SSLs and AGPSLs, we induced neuroinflammation by injection of LPS to rats as described above. One minute after LPS injection, the animals received by intraperitoneal injection, a single one of the different active principles carried by the SSLs and AGPSLs.

The active compounds (Synaptamide, Synaptamide Phosphonate) were administered at a dose of 2 mg/Kg equivalent Synaptamide. Given the differences in molar masses between the two molecules, the doses of Synaptamide Phosphonate were adjusted so as to obtain a dose, expressed in nMole/Kg, equivalent to that of a dose of Synaptamide administered at 2 mg/Kg. After 6h (optimal induction time of the neuroinflammation index, NI, see above), the animals were sacrificed, the tissues removed and the transcript levels of key markers of neuroinflammation determined by qPCR.

B.2.3. Effects of a Per Os Administration of SSL-X1 on the Neuroinflammatory Response Induced by Status Epilepticus in Rats.

Materials and methods

In these experiments, 21-day-old Sprague Dawley rats (ENVIGO, The NETHERLAND) were subjected to pilocarpine-induced status epilepticus (SE) as described below in details (§ B.3). Three groups of rats were constituted: (i) CTRL-NaCl, i.e. control rats that just received NaCl each time a treatment was given in the other groups of rats; (ii) SE-NaCl, i.e. rats that were subjected to SE and that received NaCl per os instead of SSL-X1; (iii) SE-SSL-X1, i.e. rats that were subjected to SE and that were administered with SSL-X1 vector (100 mg/Kg) per os 1 h after the onset of SE. The vectors were dissolved in 100 L of NaCl. Due to their hydrophobic nature, the preparation was emulsified until complete dissolution of the lipid vector. Twenty-four hours later, rats were sacrificed using a lethal injection of pentobarbital (250 mg/Kg; i.p.) and brain tissues, i.e. the hippocampus (HI) and the ventral limbic region (VLR, which includes the amygdala, the piriform and the insular agranular cortices) were collected and processed as mentioned above (§ B.2.2). Analysis of the expression level of the key markers of neuroinflammation was performed by RT-qPCR as described above using the primer pairs shown in Table 1. The time at which rats were sacrificed was chosen based on our preliminary experiments that allowed us to determine that the peak of brain inflammation was observed 7-24 hours after the onset of SE.

Results

Effect of synaptamide phosphonate on inflammatory markers expressed by activated microglial cell line.

The results show a dramatic reduction of IL-1β-mediated cytokine and chemokine gene induction in immortalized human microglia, when cells were pre-treated with 150 nM and 300 nM synaptamide phosphonate (FIG. 6).

Effect of synaptamide and synaptamide phosphonate, two metabolite derivatives of SSLs and AGPSLs on the neuroinflammatory response induced in vivo by lipopolysaccharides (LPS) injection.

The results show that synaptamide and synaptamide phosphonate partially prevent the LPS-mediated induction of transcripts encoding neuroinflammatory markers, when administered at the dose of 2 mg/Kg. It is noteworthy that synaptamide and synaptamide phosphonate reduced by ~50% and ~70% the Neuroinflammatory Index measured both in the hippocampus and the neocortex, respectively (FIG. 7).

Effects of per os administration of SSL-X1 on the neuroinflammatory response to status epilepticus in rats.

The results presented in FIG. 8 show that transcripts encoding MCP1, IL6 and cyclooxygenase-2 (COX-2) are strongly increased 24 h after pilocarpine-induced status epilepticus (SE) in rats, both in the hippocampus and the ventral limbic region. Per os administration of SSL-X1 at the dose of 100 mg/Kg, 1 h after the onset of SE, partially prevented this strong induction of key markers of the neuroinflammatory response to SE.

B.2.4. Effects of Metabolite Derivatives of SSLs and AGPSLs on the Levels of IL-6 mRNA In an Activated Macrophage Cell Line of Rat Origin.

B.2.4.1. Cell Culture, Treatments and RT-qPCR

NR8383 cells were seeded at 53,000 cells/$cm^2$ in T75 flasks, the medium consisted in Ham's F12K medium completed with 1% pen/strep, and 15% fetal bovine serum. When they reached confluence, they were treated with LPS (Sigma, ref 055: B55) at the concentration of 100 ng/mL, and, within less than 2 min after, with one of the following condition: DECA-EA-Pn at 10, 100, 500 or 1,000 nM, or EPA-EA-Pn at 10, 100, 500 or 1,000 ng/mL. Cells were harvested 5 hours later, and the level of IL-6 mRNA was measured by RT-qPCR as in B.2.1.4, with primers listed in table 1.

B.2.4.2. Results

In prior studies, we determined that the apparent peak of IL6-mRNA level in NR8383 cells occurred 5 hours after LPS treatment (100 ng/mL). We thus tested the effect of DECA-EA-Pn and EPA-EA-Pn on IL-6 mRNA level 5 hours after LPS treatment (FIG. 21). The results show that the induction of IL-6 mRNA levels was significantly reduced by DECA-EA-Pn and EPA-EA-PN.

B.2.5. Effects of SYN and SYN-Pn on the Resolution of Inflammation Following Pilocarpine-induced Status Epilepticus (Pilo-SE) in rats.

B.2.5.1. Methods

Male Sprague-Dawley rats (Envigo, The Netherlands) were subjected to Pilo-SE at 42 days of age (185 g). SE was triggered by pilocarpine hydrochlorate (350 mg/kg, i.p.), 30 min after the administration of scopolamine methylnitrate (1 mg/kg, s.c.), used to reduce peripheral side effects of pilocarpine. After 2 h of continuous SE, rats were administered with diazepam (10 mg/kg, i.p.) to stop SE, and then immediately treated with SYN (2 mg/kg, i.p.), SYN-Pn (2 mg/kg, i.p.) in 300 μL of NaCl. Non-treated rats subjected to Pilo-SE were injected with 300 μL of NaCl (i.p.) instead of SYN or SYN-Pn. All rats received a second administration of diazepam (5 mg/kg, s.c.), 1 h after the first one, and sacrificed 9 h post-SE. The brains were collected, the hippocampus microdissected on ice, the RNA extracted and RT-qPCR performed as described above using the primer pairs shown in Table 1. The time at which rats were sacrificed was chosen based on our preliminary experiments that allowed us to determine that the peak of brain inflammation was observed 7-12 hours after the onset of SE.

B.2.5.2. Results

Both SYN and SYN-Pn at 2 mg/kg reduced the induction of IL13 in response to Pilo-SE. SYN-Pn had a significant effect on TNFα-mRNA induction. When integrating variations of both TL10 and TNFα within an index, as explained above, SYN-Pn had an improved effect in reducing the peak of the inflammatory response following Pilo-SE (FIG. 22).

Example B-3: Effects of SSL/AGPSL Metabolic Derivatives on Cognition

I.1. Material and Methods

Animals

In this experiment we used male Sprague-Dawley rats (ENVIGO, Netherlands). Pups were received at 14 day-old (postnatal day 14 (P14)) with their foster mother, and were maintained in groups of 10 in plastic cages (405 mm×255 mm ×197 mm) with free access to food and water. All animal procedures are in accordance with the guidelines of the Animal Care and Use Committee of the University Claude Bernard Lyon 1.

Pilocarpine-Induced Status Epilepticus (Pilo-SE)

All injected solutions were prepared in sterile saline (0.9% w/v). At weaning (postnatal day 20 (P20)), Sprague-Dawley male rat pups were first injected i.p. with lithium chloride (127 mg/Kg; Sigma-Aldrich), to decrease the dose of pilocarpine needed to trigger Status Epilepticus (SE). Scopolamine methylnitrate (1 mg/Kg; Sigma-Aldrich) was injected s.c. 18 h later, to alleviate peripheral cholinergic adverse side effects. Pilocarpine hydrochloride (25 mg/Kg; Sigma-Aldrich) was injected i.p. 30 min later, to induce SE. After 30 min of continuous behavioral SE, diazepam (Valium®, Roche) was injected i.p. at 10 mg/Kg, to promote survival and initiate cessation of behavioral seizures, that completely stopped after a second s.c. injection of diazepam, given 90 min later at the dose of 5 mg/Kg. The rats were placed on a heated pad, under continuous observation, until they recovered from sedation.

Following recovery, the rats were returned to the nursing mother until P23. Control rats only received saline injections. All rats were then housed in groups of 10 and weighed daily, during the 5 following days, to control for food intake, and then twice weekly until the end of experiment (three weeks post SE). The rats which did not increase in body weight on the second day following SE, were sacrificed with a lethal dose of dolethal (250 mg/Kg; Vétoquinol, France).

Morris Water Maze (MWM) Test

Spatial learning ability was measured at 5 weeks post-SE by the Morris water maze (MWM). The training apparatus was a circular white pool (120 cm in diameter) containing water at 24° C. which was rendered opaque by addition of black gouache. A platform (10 cm in diameter) was submerged 1 cm under the water surface. The pool was divided into 4 virtual quadrants: North, East, South, and West. A platform was hidden within the northern quadrant. Four sessions were performed (three trials per session per day were carried out). On the first trial, rats were placed on the platform for 60 sec. Rats were allowed to search for the platform for 90 sec. If the rat did not find the platform within 90 sec, they were gently guided to it. All rats were allowed to remain on the platform for 15 sec.

Electrophysiology

Acute slice preparation and whole cell recordings

At P28-38, Sprague-Dawley rats were anesthetized with isoflurane, the forebrain was removed and placed in ice cold standard artificial cerebrospinal fluid (ACSF), consisting of (in mM): 124 NaCl, 5 KCl, 1.25 Na2HPO4, 2 MgSO4, 2 $CaCl_2$), 26 $NaHCO_3$, supplemented with 10 D-glucose, and bubbled with 95% 02 and 5% CO2. Hippocampal transverse slices were cut into 350 μm thick sections, using a vibratome (Leica VT1000S), and incubated in ACSF at room temperature for at least 1 h, before the transfer to the recording chamber. The ACSF used for perfusion was supplemented with picrotoxin (100 μM; Sigma-Aldrich), to block GABA-A receptors and therefore to facilitate the induction of NMDA receptors-dependent Long-Term Potentiation (LTP). CA1 pyramidal cells were visualized with a Zeiss Axioskop 2, equipped with a X40 objective, using infrared video microscopy and differential interference contrast optics. Whole-cell recordings from pyramidal neurons in the CA1 layer were obtained with patch electrodes, which were filled with a solution containing (in mM): 120 potassium gluconate, 20 KCl, 0.2 EGTA, 2 MgCl2, 10 HEPES, 4 Na2ATP, 0.3 Tris-GTP and 14 mM phosphocreatine (pH 7.3, adjusted with KOH). Drugs were applied in the bath of the hippocampal slices. Electrode resistances ranged from 3-5 MΩ. Series resistance was continually monitored, and experiments were discarded if it changed by >20%.

Capillary glass pipettes filled with ACSF and connected to an Iso-Flex stimulus isolation unit (A.M.P.I.) were placed in stratum *radiatum*, to evoke excitatory postsynaptic potentials (EPSPs) in CA1 pyramidal neurons. Cells were held at −70 mV to record EPSPs, and the stimulation strength was set to evoke EPSPs between 5-8 mV. LTP was induced by the theta burst pairing (TBP) protocol, which consisted of EPSPs paired with single back-propagating action potentials (b-APs), timed so that the b-AP (~15 ms delay) occurred at the peak of the EPSPs, as measured in the soma. A single burst contained five pairs delivered at 100 Hz and ten bursts were delivered at 5 Hz per sweep. Three sweeps were delivered at 10 s intervals for a total of 30 bursts (150 b-AP-EPSP pairs). The b-APs were elicited by direct somatic current injection (1 ms, 1-2 nA). This induction protocol was always applied within 20 min of achieving whole-cell configuration, to avoid “wash-out” of LTP.

Electrophysiological Data Acquisition and Analysis

EPSPs were recorded in whole-cell current clamp (Multiclamp 700B, Molecular Devices), filtered at 5 kHz, and digitized at 10 kHz (Digidata 1440A, Molecular Devices). Data were acquired and analyzed, using pClamp 10 software (Molecular Devices). To generate LTP summary time-course graphs, individual experiments were normalized to the baseline and three consecutive responses were averaged to generate 1-minute bins. The binned time courses of all experiments within a group were then averaged to generate the final graphs. The magnitude of LTP was calculated, based on the normalized EPSP amplitudes 36-40 min after the end of the TBP protocol.

Drugs

N-Docosahexaenoylethanolamine (synaptamide, Cayman Chemical, France), Synaptamide phosphonate, Synaptamide phosphate, docosahexaenoic (DHA), eicosapentaenoic acid ethanolamine phosphonate (EPA-EA-Pn), decanoic acid ethanolamine phosphonate (DECA-EA-Pn and SSLX2 are dissolved in saline (NaCl 0.9%). For in vivo experimentations, drugs were administered i.p or per os 1 h after cessation of SE, then each day during 6 days then once every other day for 2 weeks. Control groups received saline only. For ex vivo experimentations, molecules were added in the perfusion bath.

Statistical Analysis

The statistical analyses were performed using SigmaPlot software version 12. The paired Student’s t-tests were used to determine significance of data in the same pathway. The Mann-Whitney U test was used to determine significance between groups of data. For MWM test, data were analyzed by two-way repeated measures ANOVA followed by Fisher LSD post hoc tests to compare differences between groups at several time points.

Results are expressed as mean±SEM. Values of $p<0.05$ were considered statistically significant.

I.2. Results

Although a wide range of neuropsychological deficits may follow status epilepticus (SE), cognitive impairment is a major common problem reported by people with epilepsy, and memory deficits are frequently reported, especially in patients with Temporal Lobe Epilepsy (TLE), as well as in animal models. Because LTP, a form of synaptic plasticity that is believed to reflect processes of learning and memory formation in hippocampus, is significantly abolished in hippocampal neurons in both humans with epilepsy and animal models of epilepsy, the impairment of LTP has been considered important cellular mechanism underlying learning deficits in epilepsy. Therefore, the pilocarpine-induced experimental TLE model was used to examine the effect of synaptamide, synaptamide phosphate and synaptamide phosphonate on hippocampal LTP.

Synaptamide Rescues Hippocampal LTP Deficit Following Pilocarpine-Induced Status Epilepticus.

Hippocampal LTP, the activity-dependent change in synaptic strength, has been proposed as a cellular mechanism underlying learning and memory. Our recent studies revealed that hippocampal LTP is altered following pilocarpine-induced status epilepticus (Pilo-SE). In this study, we confirm these results in acute hippocampal slices prepared 1-2 weeks post pilocarpine-induced SE (Pilo-SE) by using whole-cell recordings from CA1 pyramidal neurons. While control neurons in slices prepared from control healthy animals exhibited robust LTP (FIG. 9A; 162.3±5.8% of baseline 36-40 min after induction, $p<0.001$), LTP was significantly inhibited in slices prepared from rats subjected to Pilo-SE (FIG. 9A; 109.6±6.1%; t=45-50 min; p=0.13). The difference in LTP amplitude between the two groups of rats is highly significant ($p<0.001$).

We then investigated whether synaptamide perfusion could reverse Pilo-SE-induced LTP deficit. We showed that synaptamide bath application (100 nM) significantly enhanced LTP induction (FIG. 9B; 166.8±12.2%, t=45-50 min, $p<0.001$) compared to the Pilo-SE slices perfused with ACSF only ($p<0.001$). Likewise, application of synaptamide at 400 nM in the bath of slices prepared from rats subjected to Pilo-SE, substantially increased LTP induction (164.2±20.5%; t=45-50 min; p=0.014) compared to the Pilo-SE slices perfused with ACSF only (FIG. 9C; p=0.008). Interestingly, LTP magnitude measured in Pilo-SE slices perfused with synaptamide 100 nM or 400 nM were similar to that of control healthy rats (FIG. 9B-C, $p>0.05$).

We next examined the in vivo effect of synaptamide. We therefore investigated whether daily synaptamide-treatment (2 mg/Kg; i.p) from day 0 (1 h post-SE) until day 7 post-SE can protect LTP induction in rats subjected to Pilo-SE. Control rats received saline instead of synaptamide. We found that rats injected with synaptamide exhibited a significant induction of LTP in hippocampal CA1 neurons (FIG. 9D; 189.7±11.4%, t=45-50 min; $p<0.001$) compared to their counterparts injected with saline ($p<0.001$). These findings reveal that impairment of hippocampal LTP during epileptogenesis can be rescued or prevented by synaptamide-treatment.

We next investigated whether intraperitoneal administration of 5 and 10 mg/Kg of synaptamide can protect LTP induction in rats subjected to Pilo-SE. Likewise, we demonstrated that LTP induction was significantly enhanced (151.54±7.15%, t=45-50 min; $p<0.001$) in slices prepared from rats subjected to Pilo-SE and injected with 5 mg/kg of synaptamide compared to rats subjected to Pilo-SE and injected with saline (FIG. 9E; $p<0.01$). In addition, we revealed that treatment of rats subjected to Pilo-SE with 10 mg/kg of synaptamide, substantially increased LTP induction (195.2±8%; t=45-50 min; $p<0.001$) compared to the Pilo-SE rats injected with saline (FIG. 9E; $p<0.001$).

Synaptamide Phosphate Rescues Hippocampal LTP Deficit Following Pilocarpine-Induced Status Epilepticus.

The inventors have synthesized a synaptamide related compound, synaptamide phosphate, that is more hydrosoluble than synaptamide. To date, synaptamide phosphate has never been characterized and its bioactivity has never been investigated. Therefore, we tested the in vitro and in vivo effects of synaptamide phosphate on hippocampus synaptic plasticity, when given after Pilo-SE, with a protocol similar to that used above for synaptamide. We found that, like synaptamide, application of synaptamide phosphate (100 nM) in the bath of slices prepared from rats subjected to Pilo-SE, significantly enhanced LTP induction (144.5±9.39%; t=45-50 min; p=0.002) compared to the Pilo-SE slices perfused with ACSF only (FIG. 10A, p=0.007). Likewise, LTP induction was also reversed in slices prepared from animals subjected to Pilo-SE and perfused with synaptamide phosphate at 400 nM (150.4±15.4%, t=45-50 min; p=0.01) when compared to the Pilo-SE slices perfused with ACSF only (FIG. 10B, P=0.046).

We next assessed LTP magnitude in slices prepared from rats subjected to Pilo-SE and injected with synaptamide phosphate (5 mg/Kg; i.p). We found that LTP induction was significantly enhanced in these animals (162.3±10.8%, t=45-50 min; p<0.001) compared to rats subjected to Pilo-SE and injected with saline (FIG. 10C, p<0.001). In contrast, there were no significant differences in amplitude of LTP monitored in slices obtained from synaptamide phosphate-treated rats and that of healthy control animals (p=0.494) indicating the ability of synaptamide phosphate, as synaptamide, to restore and to reverse LTP following Pilo-SE.

We next assessed LTP magnitude in slices prepared from rats subjected to Pilo-SE and injected (i.p.) with 2 mg/kg synaptamide phosphate. We revealed that synaptamide phosphate-treatment with 2 mg/kg markedly enhanced LTP induction (FIG. 10D, 168.9±7.1%; t=45-50 min; P<0.001) compared to the Pilo-SE rats injected with saline (p<0.001). These findings reveal that impairment of hippocampal LTP during epileptogenesis can be rescued or prevented by synaptamide phosphate-treatment.

Synaptamide Phosphonate Rescues Hippocampal LTP Deficit Following Pilocarpine-Induced Status Epilepticus.

The inventors have also synthesized a non-hydrolyzable synaptamide derivative, synaptamide phosphonate. Like, synaptamide phosphate, synaptamide phosphonate has never been characterized and its bioactivity has also never been investigated. Therefore, we explored the in vitro and in vivo effects of synaptamide phosphonate on hippocampus LTP induction in rats subjected to Pilo-SE. We found that while LTP was blocked in slices prepared from rats subjected to Pilo-SE, neurons in the same slices perfused with synaptamide phosphonate (100 nM) exhibited robust LTP (FIG. 11A, 132.2 5.01%; t=36-40 min; p<0.001). The LTP magnitude was significantly higher (159.9 10.7%, t=45-50 min; P<0.001) when slices prepared from rats subjected to Pilo-SE were perfused with 400 nM synaptamide phosphonate (FIG. 11B).

In addition, we revealed that synaptamide phosphonate-treatment (5 mg/Kg; i.p) markedly enhanced LTP induction (FIG. 11C, 162.4±11.9%; t=45-50 min; P<0.001) compared to the Pilo-SE rats injected with saline (p<0.001). LTP magnitude measured in Pilo-SE rats was similar to that of control healthy rats (p=0.726). Altogether, our data reveal that impairment of hippocampal LTP during epileptogenesis can be prevented and rescued by synaptamide phosphonate treatment.

We next explored LTP magnitude in slices prepared from rats subjected to Pilo-SE and injected (i.p) with 2 or 10 mg/kg synaptamide phosphonate. We demonstrate that rats injected with 2 mg/kg of synaptamide phosphonate exhibited a significant induction of LTP in hippocampal CA1 neurons (FIG. 11D; 183.07±9.02%, t=45-50 min; p<0.001) compared to their counterparts injected with saline (p<0.001). In addition, we found that LTP induction was significantly enhanced (162.78±12.23%, t=45-50 min; p<0.001) in slices prepared from rats injected with 10 mg/kg of synaptamide phosphonate compared to rats subjected to Pilo-SE and injected with saline (FIG. 11D, p<0.001).

We finally investigated whether oral administration of synaptamide phosphonate at 10, 30 and 100 mg/kg can also protect LTP induction in rats subjected to Pilo-SE. We reveal that LTP induction remained impaired in slices prepared from rats subjected to SE and treated with synaptamide phosphonate at 10 mg/kg (FIG. 11E, 110.7 4.7%; t=45-50 min; p=0.041). Indeed, the LTP amplitude of this group is highly different compared to that recorded in hippocampal slices of healthy rats (p<0.001) but similar to that of rats subjected to Pilo-SE and received saline (p=0.79). However, we revealed that treatment with 30 mg/kg of synaptamide phosphonate markedly enhanced LTP induction (FIG. 11E, 146.16±10%; t=45-50 min; P<0.001) compared to the Pilo-SE rats received saline (p=0.007). We also found that rats received synaptamide phosphonate at 100 mg/kg exhibited a significant induction of LTP in hippocampal CA1 neurons (FIG. 11E; 162.6±9.2%, t=45-50 min; p<0.001) compared to their counterparts injected with saline (p<0.001). These findings reveal for the first time that oral administration of synaptamide phosphonate dose dependently prevent hippocampal LTP impairment following SE.

Overall, this is the first demonstration of the protective role of synaptamide, synaptamide phosphonate and synaptamide phosphate against cognitive deficits (LTP impairment) associated with epilepsy.

Synaptamide and Synaptamide Phosphonate Improve Hippocampal LTP Induction in Healthy Rats.

Our next goal was to examine whether synaptamide or synaptamide phosphonate-treatment could improve hippocampal LTP induction in healthy rats. We thus first explored the magnitude of LTP in slices prepared from healthy rats injected with synaptamide. We found that rats injected with synaptamide (2 mg/Kg; i.p) exhibited a significant induction of LTP in hippocampal CA1 neurons (FIG. 12A; 211.9±15.14%; t=45-50 min; p<0.001) compared to their counterparts injected with saline (p<0.01). In addition, we showed that synaptamide phosphonate treatment substantially increased LTP induction (212.11±12.9%; t =45-50 min; p<0.001) in healthy rats, compared to counterparts injected with saline (p<0.001).

Overall, this is also the first demonstration of the beneficial role of synaptamide and synaptamide phosphonate in improving cognitive functions in healthy subjects by modulating hippocampal LTP.

Synaptamide and Synaptamide Phosphonate-Treatment Prevents Impairment of Learning Deficits in Epileptic Rats.

In these experiments we examined whether protection of LTP induction by synaptamide and synaptamide phosphonate-treatment in the early stages post-SE also protected spatial learning after the onset of epilepsy (5 weeks post-SE). As indicated in FIG. 15, all four groups demonstrated improvement in water maze performance during the 4 days of testing with decreases in latency to the platform from day 1 to day 4. Control healthy rats performed substantially better than epileptic rats (FIG. 15A, p<0.001). Treatment with synaptamide during the first week post-SE significantly increased spatial learning acquisition in rats that developed epilepsy after SE (FIG. 15B, p<0.01). This effect was characterized by an increased latency to find the platform at trial Day 2 and 4 in synaptamide-treated rats, compared with epileptic animals injected with saline. In addition, treatment with synaptamide phosphonate increased average latency to find the platform that was only observed at trial day 2 and 4 compared to those injected with saline (FIG. 15C, p<0.05). Thus, these data revealed that treatment with synaptamide or synaptamide phosphonate in the early stages post-SE prevents learning deficits after the onset of epilepsy.

Synaptamide Phosphonate Facilitates the Recovery of Weight Loss in Rats after Status Epilepticus.

Rats were subjected to pilocarpine-induced status epilepticus at day 0) and were administered (10 mg/Kg, i.p) Synaptamide phosphonate (SynPn) every day for 7 days. The weight of animals was daily measured. Results are described in FIG. 20. Results are expressed as the percentage of weight of animals (10-15 animals/group) at day 0. Statistical differences between Controls/SE+NaCl (*: p<0.05, ***: p<0.001) and between SE+NaCl/SE+SynPn (#: p<0.05).

Oral Administration of Docosahexaenoic Acid does not Prevent Impairment of Hippocampal LTP Following Status Epilepticus.

Synaptamide is an endogenous metabolite of DHA. Synaptamide phosphonate, however, is a non-hydrolyzable synaptamide derivative. In this experiment we investigated whether oral administration of docosahexaenoic acid (DHA) at a dose equivalent to 100 mg/kg of Synaptamide phosphonate can, like synaptamide phosphonate, protect LTP induction in rats subjected to Pilo-SE. We found the rats that received DHA exhibited a slight induction of LTP in hippocampal CA1 neurons (FIG. 16; 129.5±10.2%, t=45-50 min; p=0.011). However, the potentiation of EPSPs amplitude in slices from these animals was not statistically significant compared to that of rats subjected to Pilo-SE and received saline (p=0.214). These finding demonstrated that unlike synaptamide phosphonate, oral administration of DHA at 100 mg/kg was not able to rescue hippocampal LTP deficits following Pilo-SE. These data also revealed that synaptamide phosphonate is more effective (stunning effect) than DHA at enhancing LTP induction in rat subjected to SE.

Altogether these data suggest that synaptamide and its related compounds offer new possibilities for the treatment of cognitive impairment related to neurological and/or neurodegenerative diseases, in particular epilepsy.

Oral Administration of SSLX2 Prevents Impairment of Hippocampal LTP Following Status Epilepticus In order to determine the benefit of carrying Synaptamide Phosphonate delivered by SSLX2 lipidic vector, oral administration effects of Synaptamide phosphonate on LTP was compared to SSLX2 delivering the same amount of the active ingredient. We previously demonstrated that oral administration of synaptamide phosphonate dose dependently prevent hippocampal LTP impairment following SE. We next investigated whether oral administration of SSLX2 (administered at a dose equivalent to 10 and 30 mg/kg of Synaptamide phosphonate) can also protect LTP induction in rats subjected to Pilo-SE. We demonstrated that rats receiving SSLX2 at 10 mg/kg exhibited a slight induction of LTP in hippocampal CA1 neurons (FIG. 17A-B; 135.6±9.9%, t=45-50 min; p=0.003). However, the potentiation of EPSPs amplitude in slices from these animals was not statistically different from that of rats subjected to Pilo-SE and received saline (p=0.07) or that recorded in hippocampal slices of healthy animals (p=0.07). Moreover, the amount of this LTP is greater than that induced in slices from rats injected with the same dose (10 mg/kg) of synaptamide phosphonate, but is not statistically different (FIG. 17B; P=0.128). Strikingly, the LTP magnitude was significantly higher (172.9±6.5%, t=45-50 min; P<0.001) when slices prepared from rats subjected to Pilo-SE received 30 mg/kg of SSLX2 (FIGS. 17A and C). Indeed, the magnitude of this LTP was statistically significant compared to that recorded in slices from Pilo-SE rats receiving either saline solution (FIG. 17C; P<0.001) or synaptamide phosphonate at the equivalent dose (FIG. 17C; P=0.46). These finding demonstrated that, like synaptamide phosphonate, oral administration of SSLX2 dose dependently prevent hippocampal LTP impairment following SE. These data also revealed that when synaptamide phosphonate is delivered in the SSLX2 form, its effects on the LTP induction in rat subjected to SE are potentiated (stunning effect) when compared to synaptamide phosphonate alone.

Both Eicosapentaenoic Acid Ethanolamine Phosphonate and Decanoic Acid Ethanolamine Phosphonate Prevents Hippocampal LTP Impairment Following SE SSLX2 vectors can deliver synaptamide phosphonate containing DHA. It can also deliver other potential Synaptamide phosphonate-like active ingredients according to the identity of the fatty acid that is bound at $R_3$ position. We thus tested the potential effects of Synaptamide phosphonate-like compounds containing a short/medium fatty acid chain (decanoic acid (C10)) or other long chain PUFA (eicosapentaenoic acid (C20:5 w3)) instead of DHA (present in the Synaptamide phosphonate) on hippocampal LTP induction. To these ends, the inventors have synthesized a decanoic acid ethanolamine phosphonate (DECA-EA-Pn) and EPA ethanolamine phosphonate (EPA-EA-Pn) according to the protocol disclosed at Section 1.5. of Example A. To date, these molecules have never been characterized and its bioactivity have never been investigated. Therefore, we examined the in vivo (i.p.) effects of both DECA-EA-Pn and EPA-EA-Pn on hippocampal LTP, when given after Pilo-SE, with a protocol similar to that used above for synaptamide phosphonate. We revealed that LTP induction was enhanced (130.3±7%, t=45-50 min; p<0.001) in slices prepared from rats injected with DECA-EA-Pn (5 mg/kg) compared to rats subjected to Pilo-SE and injected with saline (FIG. 18, p=0.038). Moreover, we also demonstrated that LTP induction was significantly enhanced (154.4±12.1%, t=45-50 min; p<0.001) in slices prepared from rats subjected to Pilo-SE and injected with 5 mg/kg of EPA-EA-Pn compared to rats subjected to Pilo-SE and injected with saline (FIG. 18, p=0.006). Overall, these findings revealed that, like synaptamide phosphonate, treatments with decanoic acid ethanolamine phosphonate or EPA ethanolamine phosphonate, which can be delivered by the SSLX2 vector are also able to prevent impairment of hippocampal LTP in rat subjected to Pilo-SE.

Example B-4: Effects of Synaptamide Phosphonate (SYN-PN) on Epileptic Seizures Kindling model is a model of chronic epilepsy currently used by Anti-Seizure Drug (ASD) discovery programs (Loscher et al., 2011, Seizure 20, 359-368).

1. Material and Methods

All animal procedures were in compliance with the guidelines of the European Union (directive 2010-63), regulating animal experimentation, and have been approved by the ethical committee of the Claude Bernard Lyon 1 University. Male Sprague-Dawley rats (Envigo, France) were used in these experiments. They were housed in a temperature-controlled room (23±1° C.) under diurnal lighting conditions (lights on from 6 a.m to 6 p.m). Rats arrived 15 days prior to the beginning of the experiments. They were maintained in groups of 2 in 800 cm2 plastic cages comprising minimal environmental enrichment (nesting cardboard material, wooden gnowing sticks), and had free access to food and water.

For surgical implantation of kindling electrodes, rats weighing 220-240g were anesthetized using isoflurane (5% induction; 2% maintenance) and treated with the analgesic drug buprenorphine (0.050 mg/kg, i.m.). Their heads were positioned in a stereotaxic apparatus with the incisor bar set at −3.3 mm. Burr holes were drilled for the placement of three stainless steel jewelers' screws in the left parietal, right frontal and occipital bones, and over the site of implantation of the electrode used for amygdala kindling. This stimulation and recording electrode consisted of a teflon-isolated bipolar stainless-steel electrode aimed at the right basolateral amygdala (stereotaxic coordinates relative to Bregma: anterior-posterior, −2.8 mm; lateral, +4.8 mm; dorso-ventral, −8.5 mm). The screws placed above the parietal cortex and the frontal cortex served as recording electrodes, and the placed above the cerebellum served as grounding. Bipolar, recording and grounding electrodes were connected to a plug anchored to the skull with dental acrylic cement.

Electrical stimulation via the kindling electrode was initiated after a recovery period of 1 week after surgery, and was performed at the same time of the day (between 9:00 and 11:00 A.M. and then between 4:00 and 6:00 P.M.) to avoid intraday variance between animals. Constant current stimulations (500 μA, biphasic square-wave pulses, 50 pulses/s for 2 s) were delivered twice daily until at least 5 fully kindled seizures (secondarily generalized stage 5 seizures) were elicited. Seizure severity was classified behaviorally according to Racine's scale: stage 1, immobility, slight facial clonus (eye closure, twitching of vibrissae, sniffing); stage 2, head nodding associated with more severe facial clonus; stage 3, clonus of one forelimb; stage 4, rearing, often accompanied by bilateral forelimb clonus; stage 5, tonic-clonic seizure accompanied by loss of balance and falling.

To evaluate the effect of SYN-PN on seizure severity, SYN-PN was prepared in saline and injected intraperitoneally at 5, 10 or 50 mg/kg, 45 min prior to electrical stimulation in fully kindled rats. Briefly, the day after the last stage 5 seizure, on day 1, the rats received a first dose of SYN-PN (5 mg/kg) and were stimulated 45 minutes later. At D2 and D5, they were stimulated without SYN-PN injection to evaluate the residual effect of the 5 mg/kg dose. On D6, they received a second dose of SYN-PN (10 mg/kg) and were stimulated 45 minutes later. They were then simulated at D7 and D8 to evaluate the residual effect of the 10 mg/kg dose. On D9, rats received a third dose of SYN-PN (50 mg/kg) and were stimulated 45 minutes later. They were then simulated at D10 and D11 to evaluate the residual effect of the 50 mg/kg dose. Finally, they received 1) a daily dose of SYN-PN at 5 mg/kg from D12 to D15 and were stimulated at D16; 2) a daily dose of SYN-PN at 10 mg/kg from D19 to D22 and were stimulated at D23; and 3) a daily dose of SYN-PN at 20 mg/kg from D26 to D29 and were stimulated at D30. The treatments were then stopped. However, to assess the persistence of the effects of this series of treatments, rats continued to be stimulated at 7, 15, 42 and 56 days after the last treatment at 20 mg/kg.

2. Results

Before day DO, all rats included (n=15) developed at least 5 consecutive stage 5 seizures. When looking at the total rat population (FIG. 13A), they developed a stage 4 (n=1) or stage 5 (n=14) seizure at DO.

At D1, all rats received SYN-PN at 5 mg/kg 45 min before being stimulated, and the mean seizure severity decreased by 19.0 7.9%. Interestingly, the average decrease in seizure severity was maintained at −23.1±8.1% at D2 and then reached significance (p=0.019). This transient effect was lost at D5. The next day, at D6, the rats received a higher dose of SYN-PN (10 mg/kg), and the severity of the seizure triggered 45 minutes later was not significantly different from that at DO. However, a delayed effect was also observed at this dose: the next day and the day after, the decrease became significant (p<0.001) compared to DO, reaching at the most −39.4±11.1%. The increase in the SYN-PN dose to 50 mg/kg at D9 reinforced the decrease in seizure severity at D10, reaching −54.4±9.4% compared to DO (p<0.001), but was not significant compared to D8. Finally, stopping stimuli from D12 to D14, while maintaining the lowest daily dose of SYN-PN tested (5 mg/kg), was followed on D16 by keeping seizure severity at its lowest level (−42.0±9.2% compared to D0; p<0.001).

Figure 13A:
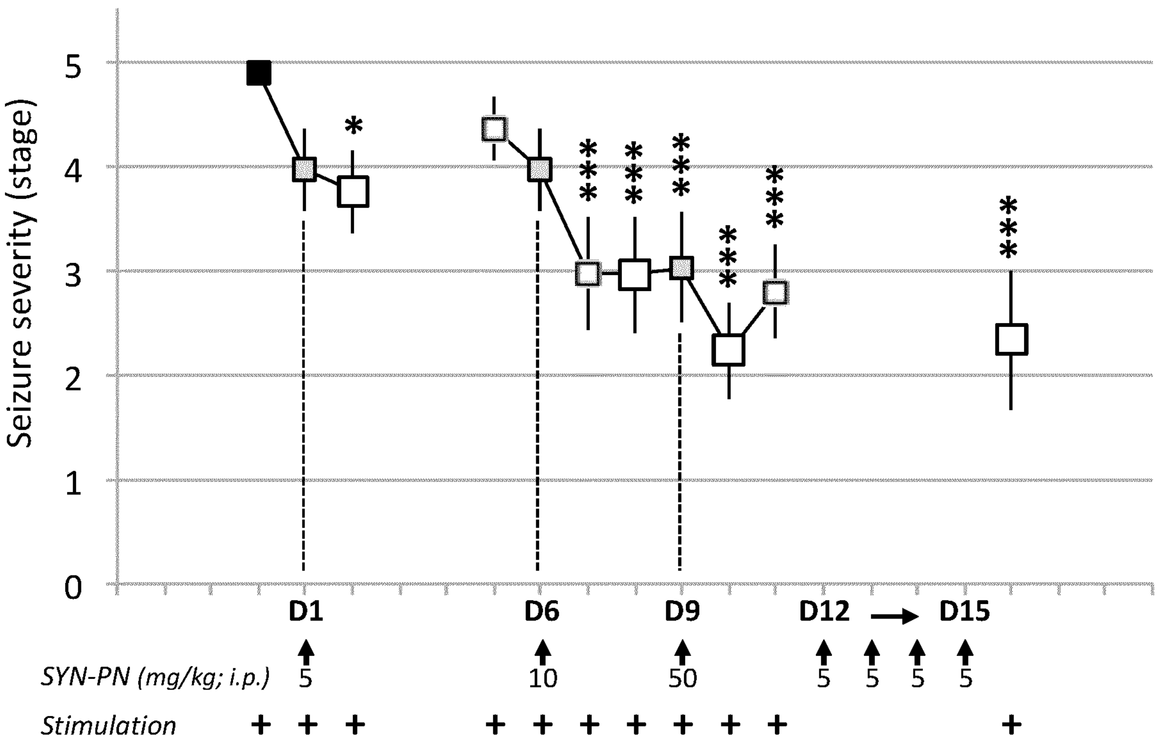
Figure 13B:
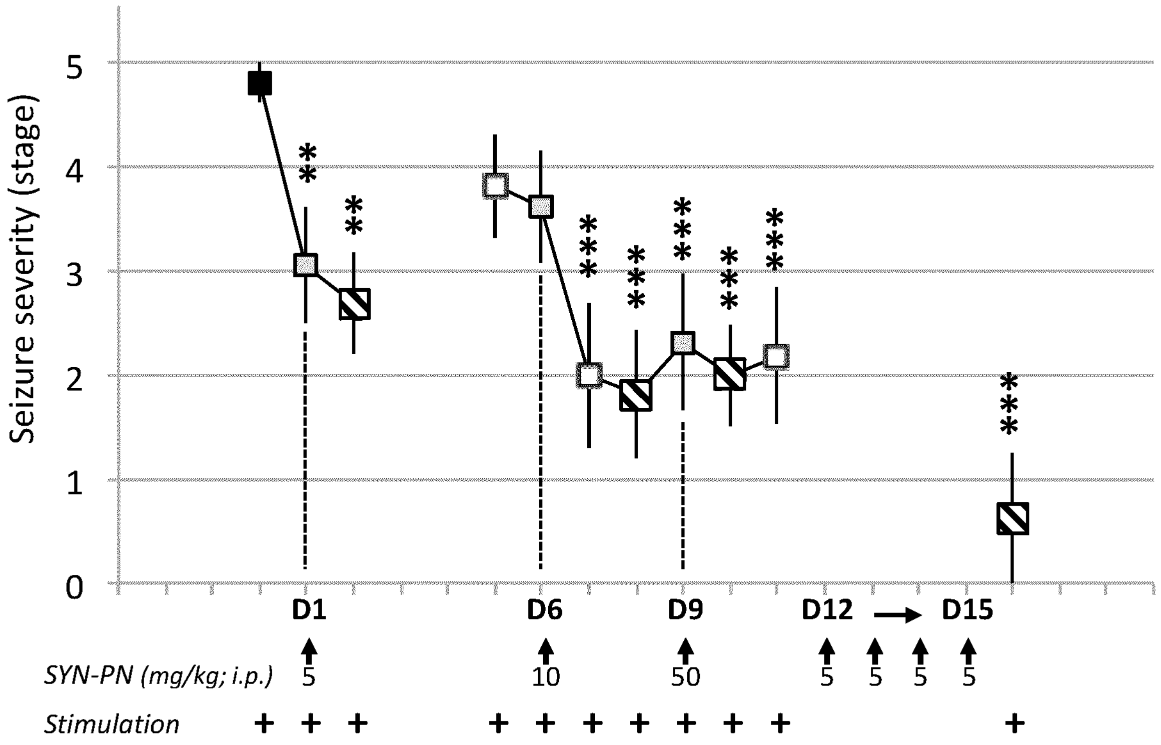
Figure 13C:
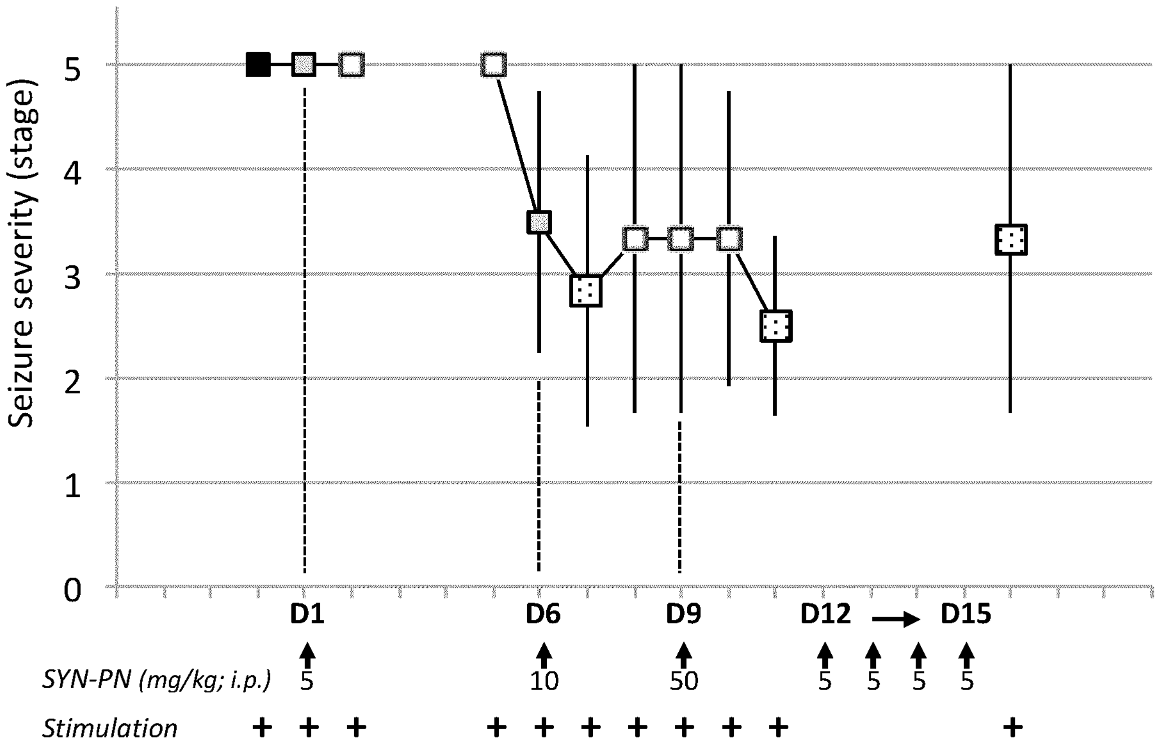
Figure 13D:
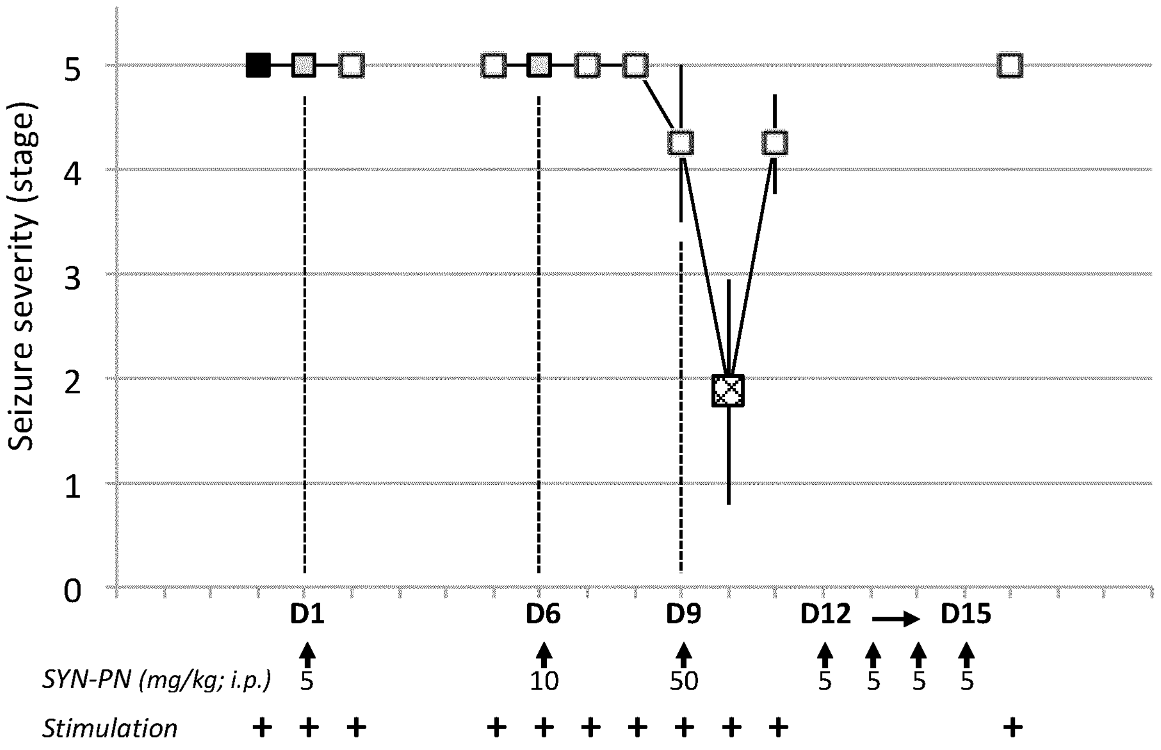

Individual examination of the effect of SYN-PN administration revealed 3 groups of rats: those responding to 5 mg/kg (8/15; FIG. 13B), 10 mg/kg (3/15; FIG. 13C) or 50 mg/kg (4/15; FIG. 13D).

For rats responding to the 5 mg/kg dose (FIG. 13B), the reduction in seizure severity was observed on the same day of administration (−36.4±11.7% compared to D0; p<0.001); however, the greatest reduction was observed 2 days after the 10 mg/kg dose (−62.3±12.7% compared to D0; p<0.001). Remarkably, stopping stimuli from D12 to D14, while maintaining a daily dose of 5 mg/kg SYN-PN, was followed on D16 by an even greater reduction in seizure severity (−87.0±13.0% compared to D0; p<0.001), with 7/8 rats remaining at stage 0 and 1/8 rat returning to stage 5.

For rats responding to the 10 mg/kg dose (FIG. 13C), the intensity of the decrease was more variable, resulting in the observed effect not significantly different from DO. However, the severity reduction was maintained even at D16 after reducing the SYN-PN dose to 5 mg/kg for 4 days.

For rats responding to the 50 mg/kg dose (FIG. 13D), the intensity of the decrease was also too variable to observe a significant effect compared to DO. However, seizure reduction was only transient and lost at D16 after reducing the SYN-PN dose to 5 mg/kg for 4 days.

In all cases, it was observed that the maximum effect on seizure severity was delayed 24 to 48 hours after administration of SYN-PN at any dose. When this maximum effect is compared in the three groups of rats following each of the doses tested, decreased severity produced by the smallest of the doses is not amplified by higher doses (FIG. 14).

After testing the effect of a daily dose of 5 mg/kg for 4 consecutive days (D12 to D15) (FIG. 13), the effect of a dose of 10 mg/kg and then 20 mg/kg was tested using the same administration protocol. Finally, when treatment was stopped, we examined whether the protective effect on seizure absence or on seizure severity was maintained, and if so, whether it was a sustained, long-lasting effect or not. FIG. 19 shows for each of the 3 groups of rats the effect observed at the last dose of 50 mg/kg (black bar), then the effect observed after 4 daily doses of 5 mg/kg, then after 4 daily doses of 10 mg/kg and after 4 daily doses of 20 mg/kg (hatched bars), and finally the severity of the seizures after treatment had been stopped for 7, 15, 42 and 56 days (dotted bars). Directly below the x-axis are also listed the numbers of rats that were free of seizures at the indicated session.

For the group of rats which responded, from the first administration, to the dose of 5 mg/kg, increasing the daily dose from 5 to 10, then to 20 mg/kg did not change the average severity of seizures.

However, it was intriguing to note that a larger number of rats were free from seizures at the dose of 5 mg/kg (7/8) compared to the dose of 10 mg/kg (4/8). This more modest effect at 10 mg/kg could likely be explained by the fact that 4/8 rats were still under the protective effect of the dose of 50 mg/kg when the daily dose of 5 mg/kg was tested. Indeed, at high doses (20 mg/kg), it was noted in the group of rats responding to 50 mg/kg that the protective effect against seizures could last up to 15 days after stopping treatment (FIG. 19).

This remarkable absence of seizures was observed in a subpopulation of rats in the 3 groups of animals. But the even more remarkable result is the absence of seizures in a significant proportion of rats 15 days after stopping treatment (7/15 rats).

SYN-PN thus appears as a disease-modifying drug in a substantial population of rats, making them free of seizures, even after almost two months of stopping treatment.

The invention claimed is:

1. A compound of formula (IIA):

$$R_5—NH—CH_2—CH(R_7)—PO_3^{2-} \quad \text{(IIA),}$$

wherein $R_5$ is docosahexaenoyl group and $R_7$ is hydrogen, and having the structure

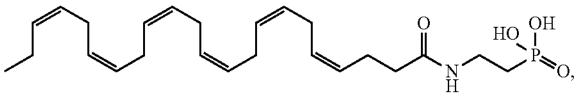 [SMILES: CC/C=C\C/C=C\C/C=C\C/C=C\C/C=C\C/C=C\CCC(=O)NCCP(=O)(O)O]

and hydrates, or pharmacologically acceptable salts thereof.

2. The compound or hydrate, or pharmacologically acceptable salt of the compound according to claim 1, which is the compound.

3. A pharmaceutical composition comprising the compound according to claim 1, or hydrate, or pharmacologically acceptable salt thereof, and a pharmaceutical acceptable excipient.

* * * * *

SEQUENCE LISTING

<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: IL1 beta Forward

<400> SEQUENCE: 1
tgtgatgaaa gacggcacac 20

<210> SEQ ID NO 2
<211> LENGTH: 23
<212> TYPE: DNA
<213> ORGANISM: artificial
<220> FEATURE:
<223> OTHER INFORMATION: IL1beta Reverse

<400> SEQUENCE: 2
cttcttcttt gggtattgtt tgg 23

<210> SEQ ID NO 3
<211> LENGTH: 21
<212> TYPE: DNA
<213> ORGANISM: Artificial Sequence
<220> FEATURE:
<223> OTHER INFORMATION: IL6 Forward

<400> SEQUENCE: 3
cccttcagga acagctatga a 21

<210> SEQ ID NO 4
<211> LENGTH: 21
<212> TYPE: DNA
<213> ORGANISM: Artificial Sequence
<220> FEATURE:
<223> OTHER INFORMATION: IL6 Reverse

<400> SEQUENCE: 4
acaacatcag tcccaagaag g 21

<210> SEQ ID NO 5
<211> LENGTH: 18
<212> TYPE: DNA
<213> ORGANISM: Artificial Sequence
<220> FEATURE:
<223> OTHER INFORMATION: TNF alpha Forward

<400> SEQUENCE: 5
tgaacttcgg ggtgatcg 18

<210> SEQ ID NO 6
<211> LENGTH: 20
<212> TYPE: DNA

-continued

<213> ORGANISM: Artificial Sequence
<220> FEATURE:
<223> OTHER INFORMATION: TNF alpha Reverse

<400> SEQUENCE: 6
gggcttgtca ctcgagtttt 20

<210> SEQ ID NO 7
<211> LENGTH: 21
<212> TYPE: DNA
<213> ORGANISM: Artificial Sequence
<220> FEATURE:
<223> OTHER INFORMATION: MCP1 Forward

<400> SEQUENCE: 7
cggctggaga actacaagag a 21

<210> SEQ ID NO 8
<211> LENGTH: 23
<212> TYPE: DNA
<213> ORGANISM: Artificial Sequence
<220> FEATURE:
<223> OTHER INFORMATION: MCP1 Reverse

<400> SEQUENCE: 8
tctcttgagc ttggtgacaa ata 23

<210> SEQ ID NO 9
<211> LENGTH: 18
<212> TYPE: DNA
<213> ORGANISM: Artificial Sequence
<220> FEATURE:
<223> OTHER INFORMATION: COX2 Forward

<400> SEQUENCE: 9
accaacgctg ccacaact 18

<210> SEQ ID NO 10
<211> LENGTH: 20
<212> TYPE: DNA
<213> ORGANISM: Artificial Sequence
<220> FEATURE:
<223> OTHER INFORMATION: COX2 Reverse

<400> SEQUENCE: 10
ggttggaaca gcaaggattt 20

<210> SEQ ID NO 11
<211> LENGTH: 20
<212> TYPE: DNA
<213> ORGANISM: Artificial Sequence
<220> FEATURE:
<223> OTHER INFORMATION: IL1 beta Forward

<400> SEQUENCE: 11
tacctgtcct gcgtgttgaa 20

<210> SEQ ID NO 12
<211> LENGTH: 23
<212> TYPE: DNA
<213> ORGANISM: Artificial Sequence
<220> FEATURE:
<223> OTHER INFORMATION: IL1 beta Reverse

<400> SEQUENCE: 12
tctttgggta atttttggga tct 23

-continued

<210> SEQ ID NO 13
<211> LENGTH: 20
<212> TYPE: DNA
<213> ORGANISM: Artificial Sequence
<220> FEATURE:
<223> OTHER INFORMATION: IL6 Forward

<400> SEQUENCE: 13
caggagccca gctatgaact 20

<210> SEQ ID NO 14
<211> LENGTH: 18
<212> TYPE: DNA
<213> ORGANISM: Artificial Sequence
<220> FEATURE:
<223> OTHER INFORMATION: IL6 Reverse

<400> SEQUENCE: 14
agcaggcaac accaggag 18

<210> SEQ ID NO 15
<211> LENGTH: 21
<212> TYPE: DNA
<213> ORGANISM: Artificial Sequence
<220> FEATURE:
<223> OTHER INFORMATION: TNF alpha Forward

<400> SEQUENCE: 15
cagcctcttc tccttcctga t 21

<210> SEQ ID NO 16
<211> LENGTH: 20
<212> TYPE: DNA
<213> ORGANISM: Artificial Sequence
<220> FEATURE:
<223> OTHER INFORMATION: TNF alpha Reverse

<400> SEQUENCE: 16
gccagagggc tgattagaga 20

<210> SEQ ID NO 17
<211> LENGTH: 18
<212> TYPE: DNA
<213> ORGANISM: Artificial Sequence
<220> FEATURE:
<223> OTHER INFORMATION: MCP1 Forward

<400> SEQUENCE: 17
agtctctgcc gcccttct 18

<210> SEQ ID NO 18
<211> LENGTH: 19
<212> TYPE: DNA
<213> ORGANISM: Artificial Sequence
<220> FEATURE:
<223> OTHER INFORMATION: MCP1 Reverse

<400> SEQUENCE: 18
gtgactgggg cattgattg 19